US010087231B2

(12) United States Patent
Palli et al.

(10) Patent No.: US 10,087,231 B2
(45) Date of Patent: Oct. 2, 2018

(54) SUBSTITUTION MUTANT RECEPTORS AND THEIR USE IN AN ECDYSONE RECEPTOR-BASED INDUCIBLE GENE EXPRESSION SYSTEM

(71) Applicant: Intrexon Corporation, Blacksburg, VA (US)

(72) Inventors: Subba Reddy Palli, Lexington, KY (US); Marianna Zinovievna Kapitskaya, Paris (FR)

(73) Assignee: Intrexon Corporation, Blacksburg, VA (US)

( * ) Notice: Subject to any disclaimer, the term of this patent is extended or adjusted under 35 U.S.C. 154(b) by 212 days.

(21) Appl. No.: 14/972,901

(22) Filed: Dec. 17, 2015

(65) Prior Publication Data

US 2017/0015728 A1 Jan. 19, 2017

Related U.S. Application Data

(62) Division of application No. 10/468,192, filed as application No. PCT/US02/05708 on Feb. 20, 2002, now Pat. No. 9,249,207.

(60) Provisional application No. 60/269,799, filed on Feb. 20, 2001, provisional application No. 60/313,908, filed on Aug. 21, 2001.

(51) Int. Cl.

| | |
|---|---|
| ***G01N 33/53*** | (2006.01) |
| ***C07K 14/705*** | (2006.01) |
| ***C07K 14/72*** | (2006.01) |
| ***C12N 15/63*** | (2006.01) |

(52) U.S. Cl.

CPC ...... *C07K 14/70567* (2013.01); *C07K 14/721* (2013.01); *C12N 15/63* (2013.01)

(58) Field of Classification Search

None

See application file for complete search history.

(56) References Cited

U.S. PATENT DOCUMENTS

| | | | |
|---|---|---|---|
| 4,631,211 | A | 12/1986 | Houghten |
| 4,859,609 | A | 8/1989 | Dull et al. |
| 4,954,655 | A | 9/1990 | Kelly |
| 4,981,784 | A | 1/1991 | Evans et al. |
| 4,985,461 | A | 1/1991 | Hsu et al. |
| 5,010,175 | A | 4/1991 | Rutter et al. |
| 5,071,773 | A | 12/1991 | Evans |
| 5,117,057 | A | 5/1992 | Hsu et al. |
| 5,171,671 | A | 12/1992 | Evans et al. |
| 5,225,443 | A | 7/1993 | Murphy et al. |
| 5,283,173 | A | 2/1994 | Fields et al. |
| 5,378,726 | A | 1/1995 | Yanagi et al. |
| 5,424,333 | A | 6/1995 | Wing |
| 5,429,952 | A | 7/1995 | Garner et al. |
| 5,459,127 | A | 10/1995 | Felgner et al. |
| 5,514,578 | A | 5/1996 | Hogness et al. |
| 5,530,028 | A | 6/1996 | Lidert et al. |
| 5,599,904 | A | 2/1997 | Evans et al. |
| 5,641,652 | A | 6/1997 | Oro et al. |
| 5,668,175 | A | 9/1997 | Evans et al. |
| 5,688,691 | A | 11/1997 | Oro et al. |
| 5,710,004 | A | 1/1998 | Evans et al. |
| 5,723,329 | A | 3/1998 | Mangelsdorf et al. |
| 5,880,333 | A | 3/1999 | Goff et al. |
| 5,919,667 | A | 7/1999 | Gage et al. |
| 5,939,442 | A | 8/1999 | Evans et al. |
| 5,989,863 | A | 11/1999 | Tang et al. |
| 6,013,836 | A | 1/2000 | Hsu et al. |
| 6,025,483 | A | 2/2000 | Yanosky |
| 6,096,787 | A | 8/2000 | Evans et al. |
| 6,117,639 | A | 9/2000 | Germann et al. |
| 6,147,282 | A | 11/2000 | Goff et al. |
| 6,245,531 | B1 | 6/2001 | Hogness et al. |
| 6,265,173 | B1 | 7/2001 | Evans et al. |
| 6,281,330 | B1 | 8/2001 | Evans et al. |
| 6,300,488 | B1 | 10/2001 | Gage et al. |
| 6,326,166 | B1 | 12/2001 | Pomerantz et al. |
| 6,333,318 | B1 | 12/2001 | Evans et al. |
| 6,379,945 | B1 | 4/2002 | Jepson et al. |
| 6,410,245 | B1 | 6/2002 | Northrop et al. |
| 6,458,926 | B1 | 10/2002 | Evans et al. |
| 6,504,082 | B1 | 1/2003 | Albertsen |
| 6,635,429 | B1 | 10/2003 | Leid et al. |
| 6,723,531 | B2 | 4/2004 | Evans et al. |
| 6,756,491 | B2 | 6/2004 | Evans et al. |
| 6,875,569 | B2 | 4/2005 | Gage et al. |
| 6,939,711 | B2 | 9/2005 | Goff et al. |
| 7,038,022 | B1 | 5/2006 | Evans et al. |
| 7,045,315 | B2 | 5/2006 | Evans et al. |
| 7,057,015 | B1 | 6/2006 | Gage et al. |
| 7,091,039 | B2 | 8/2006 | Palli et al. |
| 7,119,077 | B1 | 10/2006 | Evans et al. |

(Continued)

FOREIGN PATENT DOCUMENTS

| | | | |
|---|---|---|---|
| CN | 1313276 | | 9/2001 |
| EP | 234994 | A1 | 1/1987 |
| EP | 461809 | A1 | 6/1991 |
| EP | 798378 | B1 | 3/1997 |
| EP | 965644 | A2 | 6/1999 |

(Continued)

OTHER PUBLICATIONS

Egea P F; Rochel N; Birck C; Vachette P; Timmins P A; Moras D.: "Effects of ligand binding on the association properties and conformation in solution of retinoic acid receptors RXR and RAR", Journal of Molecular Biology, London, GB—ISSN 0022-2836, vol. 307, Nr. 2, pp. 557-576, XP004466038.

(Continued)

*Primary Examiner* — Michael Pak

(74) *Attorney, Agent, or Firm* — Sterne, Kessler, Goldstein & Fox P.L.L.C.

(57) ABSTRACT

This invention relates to the field of biotechnology or genetic engineering. Specifically, this invention relates to the field of gene expression. More specifically, this invention relates to novel nuclear receptors comprising a substitution mutation and their use in a nuclear receptor-based inducible gene expression system and methods of modulating the expression of a gene within a host cell using this inducible gene expression system.

3 Claims, 2 Drawing Sheets

Specification includes a Sequence Listing.

(56) References Cited

U.S. PATENT DOCUMENTS

| | | | |
|---|---|---|---|
| 7,183,061 | B2 | 2/2007 | Jepson et al. |
| 7,531,326 | B2 | 5/2009 | Kapitskaya et al. |
| 9,249,207 | B2 | 2/2016 | Palli et al. |
| 2002/0037514 | A1 | 3/2002 | Klein et al. |
| 2002/0110861 | A1 | 8/2002 | Dhadialla et al. |
| 2002/0119521 | A1 | 8/2002 | Palli et al. |
| 2004/0033600 | A1 | 2/2004 | Palli et al. |
| 2004/0096942 | A1 | 5/2004 | Palli et al. |
| 2004/0197861 | A1 | 10/2004 | Palli et al. |
| 2004/0235097 | A1 | 11/2004 | Zhang et al. |
| 2005/0266457 | A1 | 12/2005 | Palli et al. |
| 2006/0100416 | A1 | 5/2006 | Palli et al. |
| 2007/0161086 | A1 | 7/2007 | Palli et al. |
| 2007/0300313 | A1 | 12/2007 | Palli et al. |
| 2008/0115237 | A1 | 5/2008 | Palli et al. |
| 2008/0145935 | A1 | 6/2008 | Palli et al. |
| 2008/0176280 | A1 | 7/2008 | Kapitskaya et al. |
| 2008/0216184 | A1 | 9/2008 | Palli et al. |
| 2008/0235816 | A1 | 9/2008 | Dhadialla et al. |
| 2008/0263687 | A1 | 10/2008 | Kapitskaya et al. |
| 2008/0301825 | A1 | 12/2008 | Palli et al. |

FOREIGN PATENT DOCUMENTS

| | | | |
|---|---|---|---|
| EP | 965 644 | A2 | 12/1999 |
| EP | 1266015 | B1 | 3/2001 |
| WO | WO1989012690 | A1 | 6/1989 |
| WO | WO1992000252 | A1 | 1/1992 |
| WO | WO1994028028 | A1 | 5/1994 |
| WO | WO1995018863 | A1 | 1/1995 |
| WO | WO1995021931 | A1 | 1/1995 |
| WO | WO1996025508 | A1 | 2/1996 |
| WO | 96037609 | A1 | 5/1996 |
| WO | WO1996017823 | A1 | 6/1996 |
| WO | 9627673 | A1 | 9/1996 |
| WO | 97035985 | A1 | 3/1997 |
| WO | 9738117 | A1 | 10/1997 |
| WO | 98033162 | A2 | 1/1998 |
| WO | 1990010510 | A3 | 8/1998 |
| WO | 9902683 | A1 | 1/1999 |
| WO | WO1999036520 | A1 | 1/1999 |
| WO | 9910510 | A2 | 3/1999 |
| WO | 99051777 | A2 | 4/1999 |
| WO | 99051777 | A3 | 4/1999 |
| WO | 99027365 | A1 | 6/1999 |
| WO | 9936520 | A1 | 7/1999 |
| WO | 9958155 | A1 | 11/1999 |
| WO | 0071743 | | 11/2000 |
| WO | WO 01/02436 | A1 | 1/2001 |
| WO | 0136447 | | 3/2001 |
| WO | WO2001070816 | A2 | 3/2001 |
| WO | 0162780 | | 8/2001 |
| WO | WO2002066612 | A2 | 2/2002 |
| WO | WO2002066613 | A2 | 2/2002 |
| WO | WO2002066614 | A2 | 2/2002 |
| WO | WO2002066615 | A2 | 2/2002 |
| WO | WO2002029075 | A2 | 4/2002 |
| WO | 03105849 | A1 | 6/2003 |
| WO | WO2003105849 | A1 | 6/2003 |
| WO | WO2004005478 | A2 | 1/2004 |
| WO | WO2004072254 | A2 | 2/2004 |
| WO | WO2004078924 | A2 | 2/2004 |
| WO | WO2005017126 | A2 | 4/2005 |
| WO | WO2005108617 | A2 | 5/2005 |
| WO | WO2006083253 | A1 | 8/2006 |

OTHER PUBLICATIONS

Shea C; Hough D; Xiao J; Tzertzinis G; Maina C V.: "An rxr/usp homolog from the parasitic nematode, Dirofilaria immitis", Gene: An International Journal on Genes and Genomes, Elsevier, Amsterdam, NL—ISSN 0378-1119, vol. 324, pp. 171-182, XP004482485.

Bonneton F; et al.: "Rapid Divergence of the Ecdysone Receptor in Diptera and Lepidoptera Suggests Coevolution Between ECR and USP-RXR", Molecular Biology and Evolution, The University of Chicago Press, US—ISSN 0737-4038, vol. 20, Nr. 4, pp. 541-553, XP008028857.

Hayward D C; et al: "The structure of the USP/RXR of Xenos pecki indicates that Strepsiptera are not closely related to Diptera", Development, Genes and Evolution, Berlin, DE—ISSN 0949-944X, vol. 215, Nr. 4, pp. 213-219, XP002403944.

Moradpour D; Englert C; Blum H E: "Independent Regulation of Two Separate Gene Activities in a Continuous Human Cell Line", Biological Chemistry—ISSN 1431-6730, vol. 8/9, Nr. 379, pp. 1189-1191, XP001070604.

Martinez A; et al: "Creation of Ecdysone Receptor Chimeras in Plants for Controlled Regulation of Gene Expression", Molecular and General Genetics, Springer Verlag, Berlin, DE—ISSN 0026-8925 vol. 261, Nr. 3, pp. 546-552, XP001069830.

Holt JR et al, "Functional expression of exogenous proteins in mammalian sensory hair cells infected with adenoviral vectors." J Neurophysiol. 1999, 81:1881-1888.

Glass CK et al. "Nuclear Receptor Coactivators," Curr Opin Cell Biol. 1997, 9:222-232.

Filmus J et al."Synergistic induction of promoters containing metal- and glucocorticoid-responsive elements."Nucleic Acids Res, Jun. 11, 1992; 20(11): 2755-2760.

Fields S et al. "A novel genetic system to detect protein-protein interactions." Nature 1989, 340:245-246.

Doyle DF et al."Engineering orthogonal ligand-receptor pairs from near drugs." J Am Chem Soc. Nov. 21, 2001;123(46):11367-71.

Carlson GR et al. "The chemical and biological properties of methoxyfenozide, a new insecticidal ecdysteroid agonist." Pest Manag Sci. Feb. 2001; 57(2):115-9.

Cao S et al. "N'-tert-Butyl-N'-aroyl-N-(alkoxycarbonylmethyl)-N-aroylhydrazines, a novel nonsteroidal ecdysone agonist: syntheses, insecticidal activity, conformational, and crystal structure analysis." Canadian Journal of Chemistry, Mar. 2001 , 79(3):272-278.

Belshaw PJ et al. "Rational Design of Orthogonal Receptor-Ligand Combinations." Angewandte Chemie. International edition in English (Angew. Chem., Int. ed. Engl.) 1995, vol. 34, No. 19, pp. 2129-2132.

Belshaw PJ et al."Controlling Protein Association and Subcellular Localization with a Synthetic Ligand that Induces Heterodimerization of Proteins." Proc Natl Acad Sci. 1996, 93:4604-7.

Andrianov VG et al. "4-Aminofurazan-3-hydroximic halides." Chemistry of Heterocyclic Compounds 1992, 28(5):581-585.

Andrianov VG et al. "4-Amino-β2-1,2,4-oxadiazolines." Chemistry of Heterocyclic Compounds 1991, 22(2):216-218.

Brennan JD. "Preparation and Entrapment of Fluorescently Labeled Proteins for the Development of Reagentless Optical Biosensors." Journal of Fluorescence, Dec. 1999, 9(4): 295-312.

Hoppe UC et al. "Adenovirus-mediated Inducible Gene Expression in Vivo by Hybrid Ecdysone Receptor." Mol Therapy 2000 1(2):159-164.

Horwitz KB et al. "Nuclear receptor coactivators and corepressors." Mol Endocrinol. Oct. 1996;10(10):1167-77.

Kim JS et al."Design of TATA box-binding protein/zinc finger fusions for targeted regulation of gene expression." Proc Natl Acad Sci U S A. Apr. 15, 1997;94(8):3616-20.

Kirken RA et al. "Two discrete regions of interleukin-2 (IL2) receptor beta independently mediate IL2 activation of a PD98059/rapamycin/wortmannin-insensitive Stat5a/b serine kinase." J Biol Chem. Jun. 13, 1997;272(24):15459-65.

Nakagawa Y et al. "Quantitative structure-activity studies of insect growth regulators: XIX. Effects of substituents on the aromatic moiety of dibenzoylhydrazines on larvicidal activity against the beet armyworm Spodoptera exigua." Pest Manag Sci. Feb. 2002;58(2):131-8.

O'Brien RN et al. "Structural and functional analysis of the human phosphoenolpyruvate carboxykinase gene promoter." Biochim Biophys Acta. Dec. 27, 1995;1264(3):284-8.

Peet DJ et al."Engineering novel specificities for ligand-activated transcription in the nuclear hormone receptor RXR." Chem Biol. Jan. 1998;5(1):13-21.

(56) References Cited

OTHER PUBLICATIONS

Pierce AC et al."Computational Binding Studies of Orthogonal Cyclosporin-Cyclophilin Pairs." Angewandte Chemie. International edition in English (Angew. Chem., Int. ed. Engl.) 1997, vol. 36, No. 13-14, pp. 1466-1469.
Spencer DM et al. "Controlling signal transduction with synthetic ligands." Science. Nov. 12, 1993;262(5136):1019-24.
Trisyono A et al. "Effect of Nonsteroidal ecdysone agonists, methoxyfenozide and tebufenozide, on the European Corn Borer (Lepidoptera: Pyralidae)." J Economic Entomology 1997, 90:1486-1492.
Wurm FM et al. "Inducible overproduction of the mouse c-myc protein in mammalian cells." Proc Natl Acad Sci U S A. 1986, 83(15):5414-8.
Wipf P, et al. "Combinatorial synthesis and biological evaluation of library of small-molecule Ser/Thr-protein phosphatase inhibitors." Bioorg Med Chem. 1997, 5(1):165-77.
Wing KD et al. "RH 5849, a Nonsteroidal Ecdysone Agonist: Effects on Larval Lepidoptera." Science. 1988, 241(4864):470-472.
Zhang X et al."Study on synthesis and bioactivity of new diacylhydrazine IGR JS118." Nongyao 2003, 42:18-20.
Antoniewski C et al., The ecdysone response enhancer of the Fbp1 gene of Drosophila melanogaster is a direct target for the EcR/USP nuclear receptor, Mol Cell Biol, (1994), 14:4465-74.
Ashburner M et al., Temporal control of puffing activity in polytene chromosomes, Cold Spring Harb Symp Quant Biol, (1974), 38:655-62.
Cherbas L et al., Identification of ecdysone response elements by analysis of the Drosophila Eip28/29 gene, Genes Dev, (1991), 5:120-31.
Cho WL et al., Mosquito ecdysteroid receptor: analysis of the cDNA and expression during vitellogenesis, Insect Biochem Mol Biol, (1995), 25:19-27.
Chung AC et al., Cloning of crustacean ecdysteroid receptor and retinoid-X receptor gene homologs and elevation of retinoid-X receptor mRNA by retinoic acid, Mol Cell Endocrinol, (1998), 139:209-27.
D'Avino PP et al., The moulting hormone ecdysone is able to recognize target elements composed of direct repeats, Mol Cell Endocrinol, (1995), 113:1-9.
Dhadialla TS et al., New insecticides with ecdysteroidal and juvenile hormone activity, Annu Rev Entomol, (1998), 43:545-69.
Evans RM, The steroid and thyroid hormone receptor superfamily, Science, (1988), 240:889-95.
Fujiwara H et al., Cloning of an ecdysone receptor homolog from Manduca sexta and the developmental profile of its mRNA in wings, Insect Biochem Mol Biol, (1995), 25:845-56.
Godowski PJ et al., Signal transduction and transcriptional regulation by glucocorticoid receptor-LexA fusion proteins, Science, (1988), 241:812-6.
Guo X et al., Isolation of a functional ecdysteroid receptor homologue from the ixodid tick Amblyomma americanum (L.), Insect Biochem Mol Biol, (1997), 27:945-62.
Hannan GN et al., Cloning and characterization of LcEcR: a functional ecdysone receptor from the sheep blowfly Lucilia cuprina, Insect Biochem Mol Biol, (1997), 27:479-88.
Heberlein U et al., Characterization of Drosophila transcription factors that activate the tandem promoters of the alcohol dehydrogenase gene, Cell, (1985), 41:965-77.
Imhof MO et al., Cloning of a Chironomus tentans cDNA encoding a protein (cEcRH) homologous to the Drosophila melanogaster ecdysteroid receptor (dEcR), Insect Biochem Mol Biol, (1993), 23:115-24.
Kothapalli R et al., Cloning and developmental expression of the ecdysone receptor gene from the spruce budworm, Choristoneura fumiferana, Dev Genet, (1995), 17:319-30.
Licitra EJ et al., A three-hybrid system for detecting small ligand-protein receptor interactions, Proc Nati Acad Sci U S A, (1996), 93:12817-21.
Martinez A et al., Transcriptional activation of the cloned Heliothis virescens (Lepidoptera) ecdysone receptor (HvEcR) by muristeroneA, Insect Biochem Mol Biol, (1999), 29:915-30.
Morrison DA et al., Isolation of transformation-deficient Streptococcus pneumoniae mutants defective in control of competence, using insertion-duplication mutagenesis with the erythromycin resistance determinant of pAM beta 1, J Bacteriol, (1984), 159:870-6.
Mouillet JF et al., Cloning of two putative ecdysteroid receptor isoforms from Tenebrio molitor and their developmental expression in the epidermis during metamorphosis, Eur J Biochem, (1997), 248:856-63.
Neuberger MS et al., Recombinant antibodies possessing novel effector functions, Nature, (1984), 312:604-8.
Riddiford LM et al., Ecdysone receptors and their biological actions, Vitam Horm, (2000), 60:1-73.
Saleh DS et al., Cloning and characterization of an ecdysone receptor cDNA from Locusta migratoria, Mol Cell Endocrinol, (1998), 143:91-9.
Srini C. Perera MSPJKARTSDSRP, An analysis of ecdysone receptor domains required for heterodimerization with ultraspiracle, Archives of Insect Biochemistry and Physiology, (1999), 41:61-70.
Suhr ST et al., High level transactivation by a modified Bombyx ecdysone receptor in mammalian cells without exogenous retinoid X receptor, Proc Natl Acad Sci U S A, (1998), 95:7999-8004.
Swevers L et al., The silkmoth homolog of the Drosophila ecdysone receptor (B1 isoform): cloning and analysis of expression during follicular cell differentiation, Insect Biochem Mol Biol, (1995), 25:857-66.
Verras M et al., Cloning and characterization of CcEcR. An ecdysone receptor homolog from the mediterranean fruit fly ceratitis capitata, Eur J Biochem, (1999), 265:798-808.
Wilson JM et al., Hepatocyte-directed gene transfer in vivo leads to transient improvement of hypercholesterolemia in low density lipoprotein receptor-deficient rabbits, J Biol Chem, (1992), 267:963-7.
Yao TP et al., Drosophila ultraspiracle modulates ecdysone receptor function via heterodimer formation, Cell, (1992), 71:63-72.
Yao TP et al., Functional ecdysone receptor is the product of EcR and Ultraspiracle genes, Nature, (1993), 366:476-9.
Christopherson KS et al., Ecdysteroid-dependent regulation of genes in mammalian cells by a Drosophila ecdysone receptor and chimeric transactivators, Proc Natl Acad Sci U S A, (1992), 89:6314-8.
Kakizawa T et al., Ligand-dependent heterodimerization of thyroid hormone receptor and retinoid X receptor, J Biol Chem, (1997), 272:23799-804.
Koelle MR et al., The Drosophila EcR gene encodes an ecdysone receptor, a new member of the steroid receptor superfamily, Cell, (1991), 67:59-77.
Leid M et al., Purification, cloning, and RXR identity of the HeLa cell factor with which RAR or TR heterodimerizes to bind target sequences efficiently, Cell, (1992), 66:377-95.
Leonhardt SA et al., Agonist and antagonists induce homodimerization and mixed ligand heterodimerization of human progesterone receptors in vivo by a mammalian two-hybrid assay, Mol Endocrinol, (1998), 12:1914-30.
Metzger D et al., The human oestrogen receptor functions in yeast, Nature, (1988), 334:31-6.
No D et al., Ecdysone-inducible gene expression in mammalian cells and transgenic mice, Proc Natl Acad Sci U S A, (1996), 93:3346-51.
Perera SC et al., Studies on two ecdysone receptor isoforms of the spruce budworm, Choristoneura fumiferana, Mol Cell Endocrinol, (1999), 152:73-84.
Office Action dated Jun. 13, 2005 in U.S. Appl. No. 09/965,703, inventors Palli, et al., filed Sep. 26, 2001.
Office Action dated Nov. 24, 2004 in U.S. Appl. No. 09/965,703, inventors Palli, et al., filed Sep. 26, 2001.
Office Action dated May 14, 2004 in U.S. Appl. No. 09/965,703, inventors Palli, et al., filed Sep. 26, 2001.
Office Action dated Sep. 19, 2007 in U.S. Appl. No. 10/468,193, inventors Palli, et al., filed Dec. 17, 2003.
Office Action dated Dec. 9, 2008 in U.S. Appl. No. 09/965,697, inventors Dhadialla, et al., filed Sep. 27, 2001.

(56) References Cited

OTHER PUBLICATIONS

Office Action dated May 28, 2008 in U.S. Appl. No. 09/965,697, inventors Dhadialla, et al., filed Sep. 27, 2001.
Office Action dated Aug. 9, 2007 in U.S. Appl. No. 09/965,697, inventors Dhadialla, et al., filed Sep. 27, 2001.
Office Action dated Nov. 13, 2006 in U.S. Appl. No. 09/965,697, inventors Dhadialla, et al., filed Sep. 27, 2001.
Office Action dated Apr. 18, 2006 in U.S. Appl. No. 09/965,697, inventors Dhadialla, et al., filed Sep. 27, 2001.
Office Action dated Jul. 12, 2005 in U.S. Appl. No. 09/965,697, inventors Dhadialla, et al., filed Sep. 27, 2001.
Office Action dated Aug. 21, 2008 in U.S. Appl. No. 11/677,968, inventors Palli, et al., filed Feb. 22, 2007.
Office Action dated Mar. 13, 2008 in U.S. Appl. No. 10/468,199, inventors Kapitskaya, et al., filed Dec. 17, 2003.
Office Action dated Jun. 11, 2007 in U.S. Appl. No. 10/468,199, inventors Kapitskaya, et al., filed Dec. 17, 2003.
Office Action dated Oct. 26, 2006 in U.S. Appl. No. 10/468,199, inventors Kapitskaya, et al., filed Dec. 17, 2003.
Office action dated Aug. 22, 2006 in U.S. Appl. No. 10/239,134, inventors Palli et al., filed Sep. 19, 2002.
Office Action dated Feb. 20, 2009 in U.S. Appl. No. 11/677,968, inventors Palli et al., filed Feb. 22, 2007.
Office Action dated Feb. 25, 2009 in U.S. Appl. No. 11/841,325, inventors Dhadialla et al., filed Aug. 20, 2007.
Office Action dated Feb. 24, 2009 in U.S. Appl. No. 11/841,495, inventors Palli et al., filed Aug. 20, 2007.
Office Action dated Apr. 2, 2009 in U.S. Appl. No. 11/841,529, inventors Palli et al., filed Aug. 20, 2007.
Non-Provisional U.S. Appl. No. 09/965,697, inventors Dhadialla, et al., filed Sep. 27, 2001, published as US 2002/0110861 A1 (Aug. 2002).
Non-Provisional U.S. Appl. No. 10/468,200, inventors Palli, et al., filed Aug. 15, 2003.
Non-Provisional U.S. Appl. No. 11/841,631, inventors Palli, et al., filed Aug. 20, 2007.
Non-Provisional U.S. Appl. No. 10/468,193, inventors Palli, et al., filed Dec. 17, 2003, published as US 2006/0100416 A1 (May 2006).
Non-Provisional U.S. Appl. No. 10/468,199, inventors Kapitskaya, et al., filed Dec. 17, 2003, published as US 2004/0096942 A1 (May 2004).
Non-Provisional U.S. Appl. No. 11/841,529, inventors Palli, et al., filed Aug. 20, 2007, published as US 2007/0300313 A1 (Dec. 2007).
Non-Provisional U.S. Appl. No. 11/841,464, inventors Palli, et al., filed Aug. 20, 2007, published as US 2008/0145935 A1 (Jun. 2008).
Non-Provisional U.S. Appl. No. 11/841,495, inventors Palli, et al., filed Aug. 20, 2007, published as 2008/0115237 A1 (May 2008).
Non-Provisional U.S. Appl. No. 11/841,597, inventors Kapitskaya, et al., filed Aug. 20, 2007, published as US 2008/0176280 A1 (Jul. 2008).
Non-Provisional U.S. Appl. No. 11/841,631, inventors Palli, et al., filed Aug. 20, 2007, published as US 2008/0216184 A1 (Sep. 2008).
Non-Provisional U.S. Appl. No. 11/841,644, inventors Palli, et al., filed Aug. 20, 2007, published as US 2008/0301825 A1 (Dec. 2008).
Non-Provisional U.S. Appl. No. 11/841,325, inventors Dhadialla, et al., filed Aug. 20, 2007, published as US 2008/0235816 A1 (Sep. 2008).
Non-Provisional U.S. Appl. No. 11/841,648, inventors Kapitskava, et al., filed Aug. 24, 2007, published as US 2008/0263687 A1 (Oct. 2008).
Non-Provisional U.S. Appl. No. 11/677,968, inventors Palli, et al., filed Feb. 22, 2007, published as US 2007/0161086 A1 (Jul. 2007).
Non-Provisional U.S. Appl. No. 11/841,464, inventors Palli, et al., filed Aug. 20, 2007.
Hayward, D.C., et al., "The sequence of *Locust* RXR, homologous to *Drosophila* Ultraspiracle, and its evolutionary implications," *Development Genes and Evolution* 209: 564-571, Springer Berlin/ Heidelberg (1999).
Helmreich E.J.M., "The Biochemistry of Cell Signalling," p. 192, Oxford University Press (2001).
Hofmann, A. et al., "Rapid retroviral delivery of tetracycline-inducible genes in a single autoregulatory cassette," *Proc. Natl. Acad. Sci. USA* 93: 5185-5190, National Academy of Sciences (1996).
Perera, S.C. et al., "An Analysis of Ecdysone Receptor Domains Required for Heterodimerization With Ultraspiracle," *Archives of Insect Biochemistry and Physiology* 41: 61-70, Wiley-Liss, Inc. (1999).
Shimizu, B-i. et al., "Molting hormonal and larvicidal activities of aliphatic acyl analogs of dibenzoylhydrazine insecticides," *Steroids* 62:638-642, Elsevier Science Inc. (1997).
Talbot, W.S., et al., "Drosophila Tissues with Different Metamorphic Responses to Ecdysone Express Different Ecdysone Receptor Isoforms," *Cell* 73:1323-1337, Cell Press (1993).
UniProtKB/Swiss-Protein Database, Accession No. P49880, "Ecdysone receptor," 2 pages (1996).
UniProtKB/Swiss-Protein Database, Accession No. P49883, "Ecdysone receptor," 2 pages (1996).
Examiner's SCORE Search Results for U.S. Appl. No. 11/118,855, inventors Palli et al., filed Apr. 28, 2005, 27 pages (conducted on Aug. 14, 2007).
Examiner's SCORE Search Results for U.S. Appl. No. 11/118,855, inventors Palli et al., filed Apr. 28, 2005, 17 pages (conducted on Aug. 14, 2007).
Tease et al., "Analysis of Exchanges in Differentially Stained Meiotic Chromosomes of *Locusta migratoria* After BrdU-Substitution and FPG Staining," *Chromosoma*(*Berl.*); 69: 163-178; (1978).
Sucov, H.M., et al., "RXRα mutant mice establish a genetic basis for vitamin A signaling in heart morphogenesis," *Genes & Development* 8:1007-1018, Cold Spring Harbor Laboratory Press, united States (1994).

SUBSTITUTION MUTANT RECEPTORS AND THEIR USE IN AN ECDYSONE RECEPTOR-BASED INDUCIBLE GENE EXPRESSION SYSTEM

CROSS-REFERENCE TO RELATED APPLICATIONS

This application is a divisional of U.S. application Ser. No. 10/468,192, filed Dec. 12, 2011, which is a U.S. National Phase of PCT Application No. PCT/US2002/005708, filed Feb. 20, 2002, which claims the U.S. Provisional Application No. 60/269,799, filed Feb. 20, 2001 and U.S. Provisional Application Ser. No. 60/313,908, filed Aug. 21, 2001 each of which is incorporated herein by reference.

REFERENCE TO SEQUENCE LISTING SUBMITTED ELECTRONICALLY VIA EFS-WEB

This application includes a "2584_018000M_SL.txt," 44,535 bytes, created on Sep. 23, 2016, and submitted electronically via EFS-Web, which is hereby incorporated by reference in its entirety.

FIELD OF THE INVENTION

This invention relates to the field of biotechnology or genetic engineering. Specifically, this invention relates to the field of gene expression. More specifically, this invention relates to novel nuclear receptors comprising a substitution mutation and their use in a nuclear receptor-based inducible gene expression system and methods of modulating the expression of a gene within a host cell using this inducible gone expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PH1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83: 5414-5418; Arnheiter et al., 1990, Cell 62: 51-61; Filmus et al., 1992 Nucleic Acids Research 20: 27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, *Science* 262: 1019-24; Belshaw et al., 1996, *Proc Natl Acad Sci USA* 93: 4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limit its use for various mammalian gene switch applications.

Higher eukaryotic transcription activation system such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998, Anna. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530,028). Both analogs have exceptional safety profiles to other organisms.

The insect ecdysone receptor (BR) heterodimerizes with Ultraspiracle (USP), the insect homologue of the mammalian RXR, and binds ecdysteroid and ecdysone receptor response elements and activate transcription of ecdysone responsive genes (Riddifod et al., 2000). The EcR/USP/ligand complexes play important roles during insect development and reproduction. The EcR is a member of the steroid hormone receptor superfamily and has five modular domains, A/B (transactivation), C (DNA binding, heterodimerization)), D (Hinge, heterodimerization), E (ligand binding, heterodimerization and transactivation and F (transactivation) domains. Some of these domains such as A/B, C and E retain their function when they are fused to other proteins.

Tightly regulated inducible gene expression systems or "gene switched" are useful for various applications such as gene therapy, large scale production of proteins in cells, cell based high throughput screening assays, functional genomics and regulation of traits in transgenic plants and animals.

The first version of EcR-based gene switch used *Drosophila melanogaster* EcR (DmEcR) and *Mus musculus* RXR (MmRXR) and showed that these receptors in the presence of steroid, poasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. Nos. 5,880,333 and 6,265,173 B1).

For most applications that rely on modulating gene expression, these EcR-based systems are undesirable. Therefore, a need exists in the art for improved systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. Improved systems that are simple, compact, and dependent on ligands that are relatively inexpensive, readily available, and of low toxicity to the host would prove useful for regulating biological systems.

Recently, Applicants have shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gem expression modulation system compared to the systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide high activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

Applicants have recently made the surprising discovery that an invertebrate RXR can function similar to or better than a vertebrate RXR in an ecdysone receptor-based inducible gee expression system (see U.S. application 60/294,814, incorporated herein by reference in its entirety).

RXR is a member of the nuclear receptor superfamily and classified into subfamily 2, Group B (referred to herein as "Group B nuclear receptors"). The members of each group share 40-60% amino acid identity in the E (ligand binding) domain (Laudet et al., A Unified Nomenclature System for the Nuclear Receptor Subfamily, 1999; Cell 97:161-163). In addition to the retinoid X receptor, other members of this nuclear receptor subfamily 2, Group B include: H-2 region II binding protein (H-2RIIBP), nuclear receptor co-regulator-1 (RCoR-1), ultraspiracle (USP), 2C1 nuclear receptor, and chorion factor 1 (CF-1).

In an effort to provide improved nuclear receptor ligand binding domains, Applicants have now identified amino acid residues within Group B nuclear receptors that affect the ligand sensitivity and magnitude of induction in a nuclear receptor-based inducible gene expression system. Applicants describe herein the construction of Group B nuclear receptors that comprise substitution mutations (referred to herein as "substitution mutants") at these critical residues and the demonstration that these substitution mutant nuclear receptors are useful in methods of modulating gene expression. As presented herein, Applicants' novel substitution mutant nuclear receptors and their use in a nuclear receptor-based inducible gene expression system provide an improved inducible gene expression system in both prokaryotic and eukaryotic host cells in which ligand sensitivity and magnitude of transactivation may be selected as desired, depending upon the application.

DETAILED DESCRIPTION OF THE INVENTION

Figure 1:
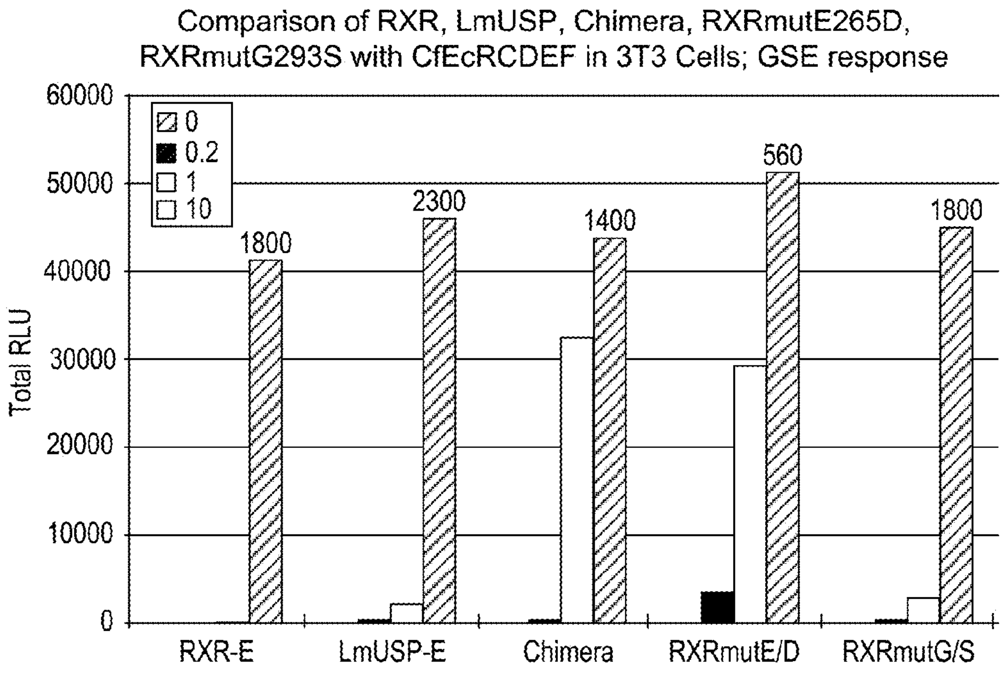
FIG. 1: Reporter gene transactivation of VP16/MmRXRα-EF, VP16/LmUSP-EF, or VP16/MmRXRα-EF mutants E265D (RXRmutE/D) or G293S (RXRmutG/S) transfected into NIH3T3 cells along with GAL4/CfEcR-DEP and pFRLuc. The cells were grown in the presence of 0, 0.2, 1 and 10 μM GS™-E for 48 hours and the reporter activity was assayed. The numbers on the top of the bars show the maximum fold induction.

Applicants have developed a novel nuclear receptor-based inducible gene expression system comprising a Group B nuclear receptor ligand binding domain comprising a substitution mutation. Applicants have shown that the effect of such a substitution mutation may increase ligand binding activity or ligand sensitivity and may be steroid or non-steroid specific. Thus, Applicants' invention provides a Group B nuclear receptor-based inducible gene expression system useful for modulating expression of a gene of interest in a host cell. Applicants' novel inducible gene expression system and its use in methods of modulating gene expression in a host cell overcome the limitations of currently available inducible expression systems and provide the skilled artisan with an effective means to control gene expression.

The present invention is useful for applications such as gene therapy, large scale production of proteins and antibodies, cell-based high throughput screening assays, orthogonal ligand screening assays, functional genomics, proteomics, metabolomics, and regulation of traits in transgenic organisms, where control of gene expression levels is desirable. An advantage of Applicants' invention is that it provides a means to regulate gene expression and to tailor expression levels to suit the user's requirements.

Definitions

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The tram "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" Includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organism, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS 0.25% milk, and no formamide; or 30% formamide, 5×SSC, 0.5% SDS). Moderate stringency hybridization conditions correspond to a higher $T_m$ e.g., 40% formamide, with 5× or 6×SCC. High stringency hybridization conditions correspond to the highest $T_m$ e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min) then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et. al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius far the hybridization step. In a more preferred embodiment, the hybridization conditions comprise 2×SSPE and 63 degrees Celsius for both the hybridization and washing steps.

In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridism to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" Is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' and of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tall" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficacy of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivative: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous nit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids hi vitro. Synthetic cationic lipids designed to limit the difficulties and dangers encountered with liposome-mediated transfection can be used to prepare liposomes for in vivo transfection of a gene encoding a marker (Felgner et al., 1987. Proc. Natl. Acad. Sci. U.S.A. 84:7413; Mackey, et al., 1988. Proc. Natl. Acad. Sci. U.S.A. 85:8027-8031; and Ulmer et al., 1993. Science 259:1745-1748). The use of cationic lipids may promote encapsulation of negatively charged nucleic acids, and also promote fusion with negatively charged cell membranes (Felgner and Ringold, 1989. Science 337:387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vi has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992. Hum. Gene Ther. 3:147-154; and Wu and Wu, 1987. J. Biol. Cheat 262: 4429-4432).

The term “transfection” means the uptake of exogenous or heterologous RNA or DNA by a cell. A cell has been “transfected” by exogenous or heterologous RNA or DNA when such RNA or DNA has been introduced inside the cell. A cell has been “transformed” by exogenous or heterologous RNA or DNA when the transfected RNA or DNA effects a phenotypic change. The transforming RNA or DNA can be integrated (covalently linked) into chromosomal DNA making up the genome of the cell.

“Transformation” refers to the transfer of a nucleic acid fragment into the genome of a host organism, resulting in genetically stable inheritance. Host organisms containing the transformed nucleic acid fragments are referred to as “transgenic” or “recombinant” or “transformed” organisms.

The term “genetic region” will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term “selectable marker” means an identifying factor, usually an antibiotic or chemical resistance gene, that is able to be selected for based upon the marker gene’s effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term “reporter gene” means a nucleic acid encoding an identifying factor that is able to be identified based upon the reporter gene’s effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), f-glucuronidase (Gus), and the like. Selectable marker genes may also be considered reporter genes.

“Promoter” refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that came a gene to be expressed in most cell types at most times are commonly referred to as “constitutive promoters”. Promoters that cause a gene to be expressed in a specific cell type are commonly referred to as “cell-specific promoters” or “tissue-specific promoters”. Promoters that cause a gene to be expressed at a specific stage of development or cell differentiation are commonly referred to as “developmentally-specific promoters” or “cell differentiation-specific promoters”. Promoters that are induced and cause a gene to be expressed following exposure or treatment of the cell with an agent, biological molecule, chemical, ligand, light, or the like that induces the promoter are commonly referred to as “inducible promoters” or “regulatable promoters”. It is further recognized that since in most cases the exact boundaries of regulatory sequences have not been completely defined, DNA fragments of different lengths may have identical promoter activity.

A “promoter sequence” is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (see Chebas L., et al., (1991), *Genes Dev.* 5, 120-131); AGGTCAN$_{(n)}$AGGTCA, where N$_{(n)}$ can be one or more spacer nucleotides (see D'Avino P P., et. al., (1995), *Mol. Cell. Endocrinol.* 113, 1-9); and GGGTTGAATGAATT (see Antoniewski C., et. al., (1994). Mol. Cell. Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, $LP_L$, $LP_R$, T7, tac, and trc promoters (useful for expression *Escherichia coli*); light regulated-, seed specific-, pollen specific-, ovary specific-, pathogenesis or disease related-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, an elongation factor 1 alpha (EF1) promoter, a phosphoglycerate kinase (PGK) promoter, a ubiquitin (Ubc) promoter, an albumin promo, the regulatory sequences of the mouse metallothionine-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immuoglobulin gene control region active in lymphoid cells, mouse mammary tumor virus control region active in testicular, breast, lymphoid and mast cells; albumin gene, Apo AI and Apo AII control regions active in liver, alpha-fetoprotein gone control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions am a different species, regulatory regions from a different gene, hybrid regulatory sequences, and regulatory sequences which do not occur in nature, but which are designed by one having ordinary skill in the art.

"RNA transcript" refers to the product resulting from RNA polymeras catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to a the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

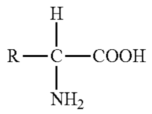

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" Is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one (1) wild-type or naturally occurring amino acid with a different amino acid relative to the wild-type or naturally occurring polypeptide. A substitution mutant polypeptide may comprise only one (1) wild-type or naturally occurring amino acid substitution and may be referred to as a "point mutant" or a "single point mutant" polypeptide. Alternatively, a substitution mutant polypeptide may comprise a substitution of two (2) or more wild-type or naturally occurring amino acids with 2 or more amino acids relative to the wild-type or naturally occurring polypeptide. According to the invention, a Group B nuclear receptor ligand binding domain polypeptide comprising a substitution mutation comprises a substitution of at least one (1) wild-type or naturally occurring amino acid with a different amino acid relative to the wild-type or naturally occurring Group B nuclear receptor ligand binding domain polypeptide.

Wherein the substitution mutant polypeptide comprises a substitution of two (2) or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wildtype amino acids (a substitution+insertion mutation).

Substitution mutants may be described using an abbreviated nomenclature system to indicate the amino acid residue and number replaced within the reference polypeptide sequence and the now substituted amino acid residue. For example, a substitution mutant in which the twentieth (20) amino acid residue of a polypeptide is substituted may be abbreviated as "x20z", wherein "x" is the amino acid to be replaced, "20" is the amino acid residue position or number within the polypeptide, and "s" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710), use of TAB linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principle and Applications for DNA Amplification*, H. Erlich, ed., Stockton Press, Chapter 6, pp. 61-70).

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pro- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immuoglobulin superfamily) and homologous proteins from different species (e.g., myosin light chain, etc.) (Reeck et al., 1987, Cell 50:667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino aid sequences of proteins that may or may not share a common evolutionary origin (see Reeck et al., 1987, Cell 50:667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported heroin. Even more preferred are nucleic acid fragments that are at least 95% identical to the DNA sequence of the nucleic acid fragments reported herein.

Two amino acid sequences are "substantially homologous" or "substantially similar" when greater then about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as detained by the match between string of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part* 1 (Griffin, A. M., and Griffin, H. G., eds.) Humana Press, New Jersey (1994); *Sequence Analysis in Molecular Biology* (von Heinje, G., ed) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS* 5:151-153) with the default parameters (GAP PENALTY-10, GAP LENGTH PENALTY-10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism. More preferably, the change is at least 5-fold greater. Even more preferably, the change is at least 10-fold greater. Still more preferably, the change is at least 100 fold greater. Even still more preferably, the change is at least 500-fold greater. Ideally, modulation of each of the given systems by its respective ligand at a chosen concentration results in a measurable change in the magnitude of expression of the gone of that system and no measurable change in expression of all other systems operable in the cell, tissue, or organisms. In such cases the multiple inducible gene regulation system is said to be "fully orthogonal". The present invention is useful to search for orthogonal ligands and orthogonal receptor-based gene expression systems such as those described in U.S. application 60/237,446, which is incorporated herein by reference in its entirety.

Gene Expression Modulation System of the Invention

Thus, Applicants have identified herein amino acid residues that affect the ligand sensitivity and magnitude of induction in a Group B-based inducible gene expression system. Applicants describe herein the construction of Group B nuclear receptors that comprise substitution mutations (referred to herein as "substitution mutants") at those critical residues and the demonstration that these substitution mutant nuclear receptors are useful in methods of modulating gene expression. As presented herein, Applicants' novel substitution mutant nuclear receptors and their use in a nuclear receptor-based inducible gene expression system provides an improved inducible gene expression system in both prokaryotic and eukaryotic host cells in which ligand sensitivity and magnitude of transactivation may be selected as desired, depending upon the application.

Thus, the present invention relates to novel substitution mutant Group B nuclear receptor polynucleotides and polypeptides, a nuclear receptor-based inducible gene expression system comprising such mutated Group B nuclear receptor polynucleotides and polypeptides, and methods of modulating the expression of a gene within a host cell using such a nuclear receptor-based inducible gene expression system.

In particular, the present invention relates to a gene expression modulation system comprising at least one gene expression cassette that is capable of being expressed in a host cell comprising a polynucleotide that encodes a polypeptide comprising a Group B nuclear receptor ligand binding domain comprising a substitution mutation. Preferably, the Group B nuclear receptor ligand binding domain comprising a substitution mutation is from a retinoid X receptor α, retinoid X receptor β, retinoid X receptor γ, H-2 region II binding protein (H-2RIIBP), Nuclear Receptor co-regulator-1 (RCoR-1), ultraspiracle protein, 2C1 nuclear receptor, and chorion factor 1 (CF-1). More preferably, the Group B nuclear receptor ligand binding domain comprising a substitution mutation is from a vertebrate retinoid X receptor α, vertebrate retinoid X receptor β, vertebrate retinoid X receptor γ, or an invertebrate retinoid X receptor.

In a specific embodiment, the gene expression modulation system comprises a) a first gene expression cassette comprising a polynucleotide that encodes a first polypeptide comprising a transactivation domain, a DNA-binding domain that recognizes a response element associated with a gene whose expression is to be modulated; and a Group B nuclear receptor ligand binding domain comprising a substitution mutation, and b) a second gene expression cassette comprising a polynucleotide that encodes a second polypeptide comprising a nuclear receptor ligand binding domain. The gene expression modulation system may further comprise a third gene expression cassette comprising: i) a response element recognized by the DNA-binding domain of the first polypeptide; ii) a promoter that is activated by the transactivation domain of the first polypeptide; and iii) a gene whose expression is to be modulated.

In a preferred embodiment, the second polypeptide comprises a Group H nuclear receptor ligand binding domain selected from the group consisting of an ecdysone receptor (EcR), a ubiquitous receptor (UR), an orphan receptor 1 (OR-1), an NER-1, a receptor-interacting protein 15 (RIP-15), a liver X receptor β (LXRβ), a steroid hormone receptor-like protein (RLD-1), a liver X receptor (LXR), a liver X receptor (LXRα), a farnesoid X receptor (FXR), a receptor-interacting protein 14 (RIP-14), and a farnesol receptor (HRR-1) ligand binding domains.

In another specific embodiment, the gene expression modulation system comprises a first gene expression cassette comprising a polynucleotide that encodes a first polypeptide comprising a DNA-binding domain that recognizes a response element associated with a gone whose expression is to be modulated and a first nuclear receptor ligand binding domain, and a second gene expression cassette comprising a polynucleotide that encodes a second polypeptide comprising a transactivation domain and a second nuclear receptor ligand binding domain, wherein one of the nuclear receptor ligand binding domains is a Group B nuclear receptor ligand binding domain comprising a substitution mutation. In a preferred embodiment, the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. The gene expression modulation system may further comprise a third gene expression cassette comprising i) a response element recognized by the DNA-binding domain of the first polypeptide of the first gene expression cassette; ii) a promoter that is activated by the transactivation domain of the second polypeptide of the second gene expression cassette; and iii) a gene whose expression is to be modulated.

In a preferred embodiment, when only one nuclear receptor ligand binding domain is a Group B ligand binding domain comprising a substitution mutation, the other nuclear receptor ligand binding domain may be from any other nuclear receptor that forms a dimer with the Group B ligand binding domain comprising the substitution mutation. In a specific embodiment, the Group B nuclear receptor ligand binding domain comprising a substitution mutation is a retinoid X receptor ligand binding domain comprising a substitution mutation, and the other nuclear receptor ligand binding domain ("partner") is from a Group H nuclear receptor. In a preferred embodiment, the Group H nuclear receptor ligand binding domain is selected from the group consisting of an ecdysone receptor (EcR), s ubiquitous receptor (UR), an orphan receptor 1 (OR-1), an NER-1, a receptor-interacting protein 15 (RIP-15), a liver X receptor β (LXRβ), a steroid hormone receptor-like protein (RLD-1), a liver X receptor (LXR), a liver X receptor (LXRα), a farnesoid X receptor (FXR), a receptor-interacting protein 14 (RIP-14), and a farnesol receptor (HRR-1) ligand binding domains.

The ecdysone receptor (EcR) ligand binding domain (LBD) may be from an invertebrate EcR, preferably selected from the class of Arthropod EcR. Preferably, the EcR is selected from the group consisting of a Lepidopteran EcR, a Dipteran EcR, an Orthopteran EcR, a Homopteran EcR and a Hemipteran EcR. More preferably, the EcR ligand binding domain for use in the present invention is from a spruce budworm *Choristoneura fumiferana* ER ("CfEcR"), a beetle *Tenebrio molitor* EcR ("TmEcR"), a *Manduca sexia* EcR ("MsEcR"), a *Heliothies virescens* EcR ("HvEcR"), a midge *Chironomus tentans* EcR ("CtEcR"), a silk moth *Bombyx mori* EcR ("BmEcR"), a squinting bush brown *Bicyclus anynana* EcR ("BanEcR"), a buckeye *Junonia coenia* EcR ("JcEcR"), a fruit fly *Drosophila melanogaster* EcR ("DmEcR"), a mosquito *Aedes aegypti* EcR ("AaEcR"), a blowfly *Lucilia capitata* ("LcEcR"), a blowfly *Lucilia cuprina* EcR ("LucEcR"), a blowfly *Calliphora vicinia* EcR ("CvEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Celuca pugilator* EcR ("CpEcR"), a whitefly *Bamecia argentifoli* EcR ("BaEcR", SEQ ID NO: 74), a leafhopper *Nephotetix cincticeps* EcR ("NcEcR", SEQ ID NO: 75) or an ixodid tick *Amblyomma americanum* EcR ("AmaEcR"). More preferably, the LBD is from a CfEcR, a DmEcR, or an AmaEcR.

The "partner" nuclear receptor ligand binding domain may further comprise a truncation mutation, a deletion mutation, a second substitution mutation, or another modification.

In a specific embodiment, the LBD is from a truncated EcR polypeptide. The EcR polypeptide truncation results in a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. Preferably, the EcR polypeptide truncation results in a deletion of at least a partial polypeptide domain. More preferably, the EcR polypeptide truncation results in a deletion of at least an entire polypeptide domain. In a specific embodiment, the EcR polypeptide truncation results in a deletion of at least an A/B-domain, a C-domain, a D-domain, an F-domain, an A/B/C-domains, an A/B/1/2-C-domains, an A/B/C/D-domains, an A/B/C/D/F-domains, an A/B/F-domains, an A/B/C/F-domains, a partial E domain, or a partial F domain. A combination of several complete and/or partial domain deletions may also be performed.

In a specific embodiment, the gene whose expression is to be modulated is a homologous gene with respect to the host cell. In another specific embodiment, the gone whose expression is to be modulated is a heterologous gene with respect to the host cell.

The ligands for use in the present invention as described below, when combined with the ligand binding domain of the nuclear receptor(s), which in turn are bound to the response element linked to a gone, provide the means for external temporal regulation of expression of the gene. The binding mechanism or the order in which the various components of this invention bind to each other, that is, for example, ligand to ligand binding domain, DNA-biding domain to response element, transactivation domain to promoter, etc., is not critical.

In a specific example, binding of the ligand to the ligand binding domain of a Group B nuclear receptor and optionally, its nuclear receptor ligand binding domain partner enables expression or suppression of the gene. This mechanism does not exclude the potential for ligand binding to the Group B nuclear receptor (GBNR) or its partner, and the resulting formation of active homodimer complexes (e.g. GBNR+GBNR or partner+partner). Preferably, one or more of the receptor domains is varied producing a hybrid gene switch. Typically, one or more of the three domains, a DNA binding domain (DBD), a ligand binding domain (LBD), and a transactivation domain (AD), may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowsk, et al. (1988) Nature, 335:563-564) or LexA protein from *Escherichia coli* (see Brent and Ptashne (1985), Cell, 43:729-736), or synthetic response elements specific for targeted interactions with proteins designed, modified, and selected for such specific interactions (see, for example, Kim, et al. (1997), *Proc. Natl. Acad. Sci. USA*, 94: 3616-3620) to accommodate hybrid receptors. Another advantage of the two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cell) or specific to certain developmental stages of the organism.

The retinoid X receptor is a member of the nuclear receptor superfamily and classified into subfamily 2, Group B (referred to herein as "Group B nuclear receptors"). The members of each group share 40-60% amino acid identity in the B (ligand binding) domain (Laudet et al., A Unified Nomenclature System for the Nuclear Receptor Subfamily, 1999; Cell 97: 161-163). In addition to the retinoid X receptor, other members of this nuclear receptor subfamily 2, Group B include: H-2 region II binding protein (H-2RIIBP) Nuclear Receptor co-regulator-1 (RCoR-1), ultraspiracle protein (USP), 2C1 nuclear receptor, and chorion factor 1 (CF-1).

Applicants previously demonstrated that a vertebrate RXR in partnership with an ecdysone receptor-based gene expression system provides an inducible gene expression system in yeast and mammalian cells that is characterized by increased ligand sensitivity and magnitude of transactivation (see pending application PCT/US01/09050). Recently, Applicants have shown that an invertebrate RXR can function as well as or better than a vertebrate RXR in an ecdysone receptor-based gene expression system by increasing gene transactivation and ligand sensitivity of the gene expression system (see application U.S. 60/294,814).

As described herein, Applicants have now identified critical amino acid residues within the ligand binding domain of RXRs that affect transactivation and ligand sensitivity of a nuclear receptor-based expression system. In Examples 2-4 infra, Applicants have identified amino acids from invertebrate retinoid X receptors (see Examples 2 and 3) and invertebrate ultraspiracle proteins (see Example 4) ligand binding domains that differ from amino acids of vertebrate RXRs. Applicants made substitution mutants within vertebrate RXR ligand binding domains by replacing the wild type vertebrate RXR amino acid with that of an invertebrate RXR or USP at their analogous position and tested these substitution mutants for their ability to transactivate gee expression in a nuclear receptor-based inducible gene expression system. As presented in the Examples herein, Applicants have now identified several novel retinoid X receptor ligand binding domain substitution mutants that exhibit unexpected and surprising levels of transactivation activity and/or ligand sensitivity.

Given the close relatedness of retinoid X receptor to other Group B nuclear receptors. Applicants' identified retinoid X receptor binding domain substitution mutations are also expected to work when introduced into the analogous position of the ligand binding domains of other Group B nuclear receptor to modify ligand binding or ligand sensitivity in a Group B nuclear receptor-based gene expression system. Applicants' novel substitution mutated Group B nuclear receptor ligand binding domain polynucleotides and polypeptides are useful in a nuclear receptor-based inducible gene modulation system for various applications including gene therapy, expression of proteins of interest in host cells, production of transgenic organisms, and cell-based assays.

In particular, Applicants describe herein a novel gone expression modulation system comprising a Group B nuclear receptor ligand binding domain comprising a substitution mutation. This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides. Applicants have demonstrated for the first time that a substitution mutated nuclear receptor can be used as a component of a nuclear receptor-based inducible gene expression system to modify ligand binding activity and/or ligand specificity in both prokaryotic and eukaryotic cells. As discussed herein, Applicants' findings are both unexpected and surprising.

Preferably the Group B nuclear receptor-based gene expression modulation system of the present invention may be either heterodimeric and homodimeric. In a preferred embodiment, the Group B nuclear receptor ligand binding domain heterodimerizes with an ecdysone receptor ligand binding domain to form a function EcR complex. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476479; Yao, et al., (1992) Cell 71, 63-72). However, the complex may also be a homodimer as detailed below. The functional ecdysteroid receptor complex may also include additional protein(s) such as immunophilins. Additional members of the steroid receptor family of protein, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well a the promiscuous coactivator C response element B binding protein, CBP/p300 (for review see lass et al., Curt. Opin. Cell Biol. 9: 222-232, 1997). Also, protein cofactors generally known as corepressors (also known as repressors, silencers, or silencing mediators) may be required to effectively inhibit transcriptinal activation in the absence of ligand. These corepressors may interact with the unliganded ecdysone receptor to silence the activity at the response element. Current evidence suggests that the binding of ligand changes the conformation of the receptor, which results in release of the corepressors and recruitment of the above described coactivators, thereby abolishing their silencing activity. Examples of compressors include N-CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, *Science* 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motif, the P-box and the D-box, which confer specificity for ecdysone response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD. DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. Applicants have previously shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050).

Gene Expression Cassettes of the Invention

The novel nuclear receptor-based inducible gene expression system of the invention comprises at least one gene expression cassette that is capable of being expressed in a bot cell, wherein the gene expression cassette comprises a polynucleotide that encodes a polypeptide comprising a Group B nuclear receptor ligand binding domain comprising a substitution mutation. Thus. Applicants' invention also provides novel gene expression cassettes for use in the gene expression system of the invention.

In a specific embodiment, the gene expression cassette that is capable of being expressed in a host cell comprises a polynucleotide that encodes a polypeptide selected from the group consisting of a) a polypeptide comprising a transactivation domain, a DNA-binding domain, and a Group B nuclear receptor ligand binding domain comprising a substitution mutation; b) a polypeptide comprising a DNA-binding domain and a Group B nuclear receptor ligand binding domain comprising a substitution mutation; and c) a polypeptide comprising a transactivation domain and a Group B nuclear receptor ligand binding domain comprising a substitution mutation.

In another specific embodiment, the present invention provides a gene expression cassette that is capable of being expressed in a host cell, wherein the gene expression cassette comprises a polynucleotide that encodes a hybrid polypeptide selected from the group consisting of a) a hybrid polypeptide comprising a transactivation domain, a DNA-binding domain, and a Group B nuclear receptor ligand binding domain comprising a substitution mutation; b) a hybrid polypeptide comprising a DNA-binding domain and a Group B nuclear receptor ligand binding domain comprising a substitution mutation; and c) a hybrid polypeptide comprising a transactivation domain and a Group B nuclear receptor ligand birding domain comprising a substitution mutation. A hybrid polypeptide according to the invention comprises at least two polypeptide fragments, wherein each polypeptide fragment is from a different source, i.e., a different nuclear receptor, a different species, etc. The hybrid polypeptide according to the invention may comprise at least two polypeptide domains, wherein each polypeptide domain is from a different source.

In a specific embodiment, the Group B nuclear receptor ligand binding domain comprising a substitution mutation is from an retinoid X receptor α (RXRα), retinoid X receptor β (RXRβ), retinoid X receptor γ (RXRγ), H-2 region II binding protein (H-2RIIBP), nuclear receptor co-regulator-1 (RCoR-1), ultraspiracle protein (USP), 2C1 nuclear receptor, or chorion factor 1 (CF-1). In a preferred embodiment, the Group B nuclear receptor ligand binding domain is from a vertebrate retinoid X receptor α, vertebrate retinoid X receptor β, vertebrate retinoid X receptor γ, or an invertebrate retinoid X receptor.

Thus, the present invention also provides a gene expression cassette comprising a polynucleotide that encodes a polypeptide selected from the group consisting of a) a polypeptide comprising a transactivation domain, a DNA-binding domain, and a retinoid X receptor ligand binding domain comprising a substitution mutation; b) a polypeptide comprising a DNA-binding domain and a retinoid X receptor ligand binding domain comprising a substitution mutation; and c) a polypeptide comprising a transactivation domain and a retinoid X receptor ligand binding domain comprising a substitution mutation. Preferably, the gene expression cassette comprises a polynucleotide that encodes a hybrid polypeptide selected from the group consisting of a) a hybrid polypeptide comprising a transactivation domain, a DNA-binding domain, and a retinoid X receptor ligand binding domain comprising a substitution mutation; b) a hybrid polypeptide comprising a DNA-binding domain and a retinoid X receptor ligand binding domain comprising a substitution mutation; and c) a hybrid polypeptide comprising a transactivation domain and a retinoid X receptor ligand binding domain comprising a substitution mutation; wherein the encoded hybrid polypeptide comprises at least two polypeptide fragments, wherein each polypeptide fragment is from a different source.

The retinoid X receptor (RXR) ligand binding domain (LBD) may be from an invertebrate or vertebrate RXR. Preferably, the RXR ligand binding domain for use in the present invention is from a human *Homo sapiens* (HsRXR), a mouse *Mus musculus* (MmRXR), a rat *Rattus norvegicus* (RnRXR), a chicken *Gallus gallus* (GgRXR), a domestic pig *Sus scrofa domestica* (SsRXR), a frog *Xenopus laevis* (Xl-RXR), a zebra fish *Danto rerio* (DrRXR), a beetle *Tenebrio molitor* RXR homolog ("TmRXR"), a locust *Locusta migratoria* USP/RXR homolog (referred to as either "LmUSP" or "LmRXR"), an aphid *Myzus persicae* RXR homolog ("MpRXR"), a honeybee *Apis mellifera* RXR homolog ("AmRXR"), a fiddler crab *Celuca pugilator* RXR homolog ("CpRXR"), an ixodid tick *Amblyomma americium* RXR homolog 1 ("AmaRXR1"), an ixodid tick *Amblyomma americium* RXR homolog 2 ("AmaRXR2"), a tunicate *Polyandrocarpa misakiensis* (PmRXR), or a jellyfish *Tripedolia cystophora* RXR (TcRXR). More preferably, the LBD is from a MmRXR or a HsRXR.

In a specific embodiment, the Group B nuclear receptor ligand binding domain is encoded by a polynucleotide comprising a codon mutation that results in a substitution of an amino acid residue, wherein the amino acid residue is at a position equivalent or analogous to an amino acid residue selected from the group consisting of a) 401 or 429 of SEQ ID NO: 1, b) 401 and 429 of SEQ ID NO: 1, c) 337, 344, 355, 385, 431, 442, 462, 470, 472, 473, 495, 500, 511, 516, or 528 of SEQ ID NO: 2, d) 321, 322, and 323 of SEQ ID NO: 2, e) 450, 451, and 452 of SEQ ID NO: 2, f) 455, 456, 457, and 458 of SEQ ID NO: 2, g) 470, 472, and 473 of SEQ ID NO: 2, h) 475, 476, 477, 478, and 479 of SEQ ID NO: 2, and i) 481, 482, and 483 of SEQ ID NO: 2. In a preferred embodiment, the (Group B nuclear receptor ligand binding domain is from a retinoid X receptor.

In another specific embodiment, the Group B nuclear receptor ligand binding domain is encoded by a polynucleotide comprising a codon mutation that results in a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an aspartic acid residue at a position equivalent or analogous to amino acid residue 401 of SEQ ID NO: 1, and a serine residue at a position equivalent to or analogous to amino acid of amino acid residue 429 of SEQ ID NO: 1, d) a serine residue at a position equivalent or analogous to amino acid residues 337, 495, 500, or 528 of SEQ ID NO: 2, e) an asparagine residue at a position equivalent or analogous to amino acid residue 344 of SEQ ID NO: 2, f) an arginine residue at a position equivalent to or analogous to amino acid of amino acid residues 355 or 511 of SEQ ID NO: 2, g) an alanine residue at a position equivalent or analogous to amino acid residues 385 or 470 of SEQ ID NO: 2, h) a leucine residue at a position equivalent or analogous to amino acid residue 431 or 462 of SEQ ID NO: 2, i) a lysine residue at a position equivalent to or analogous to amino acid of amino acid residue 442 of SEQ ID NO: 2, j) an aspartic acid residue at a position equivalent or analogous to amino acid residue 472 of SEQ ID NO: 2, k) a glutamic acid at a position equivalent to or analogous to amino acid of amino acid residue 473 of SEQ ID NO: 2, l) a valine residue at a position equivalent to or analogous to amino acid of amino acid residue 516 of SEQ ID NO: 2, m) a leucine residue at a position equivalent to or analogous to amino acid of amino acid residue 321 of SEQ ID) NO: 2, an arginine residue at a position equivalent to or analogous to amino acid of amino acid residue 322 of SEQ ID NO: 2, and a valine residue at a position equivalent to or analogous to amino acid of amino acid residue 323 of SEQ ID NO: 2, n) a glutaric acid residue at a position equivalent to or analogous to amino acid of amino acid residue 450 of SEQ ID NO: 2, a valine residue at a position equivalent to or analogues to amino acid of amino acid residue 451 of SEQ ID NO: 2, and an arginine residue at a position equivalent to or analogous to amino acid of amino acid residue 452 of SEQ ID NO: 2, o) a lysine residue at a position equivalent to or analogous to amino acid of amino acid residue 455 of SEQ ID NO: 2, a serine residue at a position equivalent to or analogous to amino acid of amino acid residue 456 of SEQ ID NO: 2, an alanine residue at a position equivalent to or analogous to amino acid of amino acid residue 457 of SEQ ID NO: 2, and a glutamine residue at a position equivalent to or analogous to amino acid of amino acid residue 458 of SEQ ID NO: 2, p) an alanine residue at a position equivalent to or analogous to amino acid of amino acid residue 470 of SEQ ID NO: 2, an aspartic acid residue at a position equivalent to or analogous to amino acid of amino acid residue 472 of SEQ ID NO: 2, and a tyrosine residue at a position equivalent to or analogous to amino acid of amino acid residue 473 of SEQ ID NO: 2, q) a threonine residue at a position equivalent to or analogous to amino acid of amino acid residues 475, 477, and 478 of SEQ ID NO: 2, an arginine residue at a position equivalent to or analogous to amino acid of amino acid residue 476 of SEQ ID NO: 2, and a histidine residue at a position equivalent to or analogous to amino acid of amino acid residue 479 of SEQ ID NO: 2, or r) an aspartic acid residue at a position equivalent to or analogous to amino acid of amino acid residue 481 of SEQ ID NO: 2, a glutamic acid residue at a position equivalent to or analogous to amino acid of amino acid residue 482 of SEQ ID NO: 2, and a proline residue at a position equivalent to or analogous to amino acid of amino acid residue 483 of SEQ ID NO: 2. In a preferred embodiment, the Group B nuclear receptor ligand binding domain is from a retinoid X receptor.

In another specific embodiment, the Group B nuclear receptor ligand binding domain comprising a substitution mutation is a retinoid X receptor ligand binding domain comprising a substitution mutation encoded by a polynucleotide comprising a codon mutation or codon mutations that results in a substitution mutation selected from the group consisting of a) E401D or G429S of SEQ ID NO: 1, b) E401D and G429S of SEQ ID NO: 1, c) T337S, D344N, K355R, S385A, M431L, R442K, V462L, S470A, E471D, T473E, A495S, E500S, K511R, T516V, or A528S of SEQ ID NO: 2, d) G321L, P322R, and G323V of SEQ ID NO: 2, e) D450E, A451V, and K452R of SEQ ID NO: 2, f) S455K, N456S, P457A, and S458Q of SEQ ID NO 2, g) S470A, E472D, and T473Y of SEQ ID NO: 2, h) C475T, K476R, Q477T, K478T, and Y479H of SEQ ID NO: 2, and i) B481D, Q482E, and Q483P of SEQ ID NO: 2.

In another specific embodiment, the Group B nuclear receptor ligand binding domain comprises a substitution mutation at a position equivalent or analogous to amino acid residue a) 401 or 429 of SEQ ID NO: 1, b) 401 and 429 of SEQ ID NO: 1, c) 337, 344, 355, 385, 431, 442, 462, 470, 472, 473, 495, 500, 511, 516, or 528 of SEQ ID NO: 2, d) 321, 322, and 323 of SEQ ID NO: 2, e) 450, 451, and 452 of SEQ ID NO: 2, f) 455, 456, 457, and 458 of SEQ ID NO: 2, g) 470, 472, and 473 of SEQ ID NO: 2, h) 475, 476, 477, 478, and 479 of SEQ ID NO: 2, and i) 481, 482, and 483 of SEQ ID NO: 2. In a preferred embodiment, the Group B nuclear receptor ligand binding domain is from a retinoid X receptor.

Preferably, the Group B nuclear receptor ligand binding domain comprises a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an aspartic acid residue at a position equivalent or analogous to amino acid residue 401 of SEQ ID NO: 1, and a serine residue at a position equivalent to or analogous to amino acid of amino acid residue 429 of SEQ ID NO: 1, d) a serine residue at a position equivalent or analogous to amino acid residues 337, 495, 500, or 528 of SEQ ID NO: 2, e) an asparagine residue at a position equivalent or analogous to amino acid residue 344 of SEQ ID NO: 2, f) an arginine residue at a position equivalent to or analogous to amino acid of amino acid residues 355 or 511 of SEQ ID NO: 2, g) an alanine residue at a position equivalent or analogous to amino acid residues 385 or 470 of SEQ ID NO: 2, h) a leucine residue at a position equivalent or analogous to amino acid residue 431 or 462 of SEQ ID NO: 2, i) a lysine residue at a position equivalent to or analogous to amino acid of amino acid residue 442 of SEQ ID NO: 2, j) an aspartic acid residue at a position equivalent or analogous to amino acid residue 472 of SEQ ID NO: 2, k) a glutamic aid at a position equivalent to or analogous to amino acid of amino acid residue 473 of SEQ ID NO: 2, l) a valine residue at a position equivalent to or analogous to amino acid of amino acid residue 516 of SEQ ID NO: 2, m) a leucine residue at a position equivalent to or analogous to amino acid of amino acid residue 321 of SEQ ID NO: 2, an arginine residue at a position equivalent to or analogous to amino acid of amino acid residue 322 of SEQ ID NO: 2, and a valine residue at a position equivalent to or analogous to amino acid of amino acid residue 323 of SEQ ID NO: 2, a) a glutamic acid residue at a position equivalent to or analogous to amino acid of amino acid residue 450 of SEQ ID NO: 2, a valine residue at a position equivalent to or analogous to amino acid of amino acid residue 451 of SEQ ID NO: 2, and an arginine residue at a position equivalent to or analogous to amino acid of amino acid residue 452 of SEQ ID NO: 2, o) a lysine residue at a position equivalent to or analogous to amino acid of amino acid residue 455 of SEQ ID NO: 2, a serine residue at a position equivalent to or analogous to amino acid of amino acid residue 456 of SEQ ID NO: 2, an alanine residue at a position equivalent to or analogous to amino acid of amino acid residue 457 of SEQ ID NO: 2, and a glutamine residue at a position equivalent to or analogous to amino acid of amino acid residue 458 of SEQ ID NO: 2, p) an alanine residue at a position equivalent to or analogous to amino acid of amino acid residue 470 of SEQ ID NO: 2, an aspartic acid residue at a position equivalent to or analogous to amino acid of amino acid residue 472 of SEQ ID NO: 2, and a tyrosine residue at a position equivalent to or analogous to amino acid of amino acid residue 473 of SEQ ID NO: 2, q) a threonine residue at a position equivalent to or analogous to amino acid of amino acid residues 475, 477, and 478 of SEQ ID NO: 2, an arginine residue at a position equivalent to or analogous to amino acid of amino acid residue 476 of SEQ ID NO: 2, and a histidine residue at a position equivalent to or analogous to amino acid of amino acid residue 479 of SEQ ID NO: 2, or r) an aspartic acid residue at a position equivalent to or analogous to amino acid of amino acid residue 481 of SEQ ID NO: 2, a glutamic acid residue at a position equivalent to or analogous to amino acid of amino acid residue 482 of SEQ ID NO: 2, and a proline residue at a position equivalent to or analogous to amino acid of amino acid residue 483 of SEQ ID NO: 2. In a preferred embodiment, the Group B nuclear receptor ligand binding domain is from a retinoid X receptor.

In another specific embodiment, the Group B nuclear receptor ligand binding domain comprising a substitution mutation is a retinoid X receptor ligand binding domain comprising a substitution mutation, wherein the substitution mutation is selected from the group consisting of a) E401D or G429S of SEQ ID NO: 1, b) E401D and G429S of SEQ ID NO: 1, c) T337S, D344N, K355R, S385A, M431L, R442K, V462L, S470A, E471D, T473B, A495S, E500S, K511R, T516V, or A528S of SEQ ID NO: 2, d) G321L, P322R, and G323V of SEQ ID NO: 2, e) D450B, A451V, and K452R of SEQ ID NO: 2, f) S455K, N456S, P457A, and S458Q of SEQ ID NO: 2, g) S470A, E472D, and T473Y of SEQ ID NO: 2, h) C475T, K476R, Q477T, K478T, and Y479H of SEQ ID NO: 2, and i) B481D, Q482E, and Q483P of SEQ ID NO: 2.

The DNA binding domain (DBD) can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a Group B nuclear receptor member DBD, a steroid/thyroid hormone nuclear receptor superfamily member DBD, a bacterial LacZ DBD, or a DBD. More preferably, the DBD is an ecdysone receptor (EcR) DBD [SEQ ID NO: 3 (polynucleotide) or SEQ ID NO: 4 (polypeptide)], a GAL4 DBD [SEQ ID NO: 5 (polynucleotide) or SEQ ID NO: 6 (polypeptide)], or a LexA DBD [(SEQ ID NO: 7 (polynucleotide) or SEQ ID NO: 8 (polypeptide)].

The transactivation domain (abbreviated “AD” or “TA”) may be any Group B nuclear receptor member AD, steroid/thyroid hormone nuclear receptor AD, synthetic or chimeric AD, polyglutamine AD, basic or acidic amino acid AD, a VP16 AD, a GAL4 AD, an NP-κB AD, a BP64 AD, a B42 acidic activation domain (B42AD), a P65 activation domain (P65AD), or an analog, combination, or modification thereof.

In a specific embodiment, the AD is a synthetic or chimeric AD, or is obtained from an ecdysone receptor, a glucocorticoid receptor, VP16, GAL4, NF-kB, or B42 acidic activation domain AD. Preferably, the AD is an EcR AD [SEQ ID NO: 9 (polynucleotide) or SEQ ID NO: 10 (polypeptide)] a VP16 AD [SEQ ID NO: 1 (polynucleotide) or SEQ ID NO: 12 (polypeptide)], a B42 AD [SEQ ID NO: 13 (polynucleotide) or SEQ ID NO: 14 (polypeptide)], or a p65 AD [SEQ ID NO: 15 (polynucleotide) or SEQ ID NO: 16 (polypeptide)].

In a specific embodiment, the gene expression cassette encodes a hybrid polypeptide comprising a) a DNA-binding domain encoded by a polynucleotide comprising a nucleic acid sequence of SEQ ID NO: 3, SEQ ID NO: 5, or SEQ ID NO: 7; a transactivation domain encoded by a polynucleotide comprising a nucleic acid sequence of SEQ ID NO: 9, SEQ ID NO: 11, SEQ ID NO: 13, or SEQ ID NO: 15; and a Group B nuclear receptor ligand binding domain comprising a substitution mutation encoded by a polynucleotide according to the invention; b) a DNA-binding domain encoded by a polynucleotide comprising a nucleic acid sequence of SEQ ID NO: 3, SEQ ID NO: 5, or SEQ ID NO: 7, and a Group B nuclear receptor ligand binding domain comprising a substitution mutation encoded by a polynucleotide according to the invention, or c) a transactivation domain encoded by a polynucleotide comprising a nucleic acid sequence of SEQ ID NO: 9, SEQ ID NO: 11, SEQ ID NO: 13, or SEQ ID NO: 15; and a Group B nuclear receptor ligand binding domain comprising a substitution mutation encoded by a polynucleotide according to the invention. Preferably, the Group B nuclear receptor ligand binding domain comprising a substitution mutation is an ecdysone receptor ligand binding domain comprising a substitution mutation encoded by a polynucleotide according to the invention.

In another specific embodiment, the gene expression cassette encodes a hybrid polypeptide comprising a) a DNA-binding domain comprising an amino acid sequence of SEQ ID NO: 4, SEQ ID NO: 6, or SEQ ID NO: 8; a transactivation domain comprising an amino acid sequence of SEQ ID NO: 10, SEQ ID NO: 12, SEQ ID NO: 14, or SEQ ID NO: 16; and a Group B nuclear receptor ligand binding domain comprising a substitution mutation according to the invention; b) a DNA-binding domain comprising an amino acid sequence acid sequence of SEQ ID NO: 4, SEQ ID NO: 6, or SEQ ID NO: 8; and a group B nuclear receptor ligand binding domain comprising a substitution mutation according to the invention, or c) a transactivation domain comprising an amino acid sequence of SEQ ID NO: 10, SEQ ID NO: 12. SEQ ID NO: 14, or SEQ ID NO: 16; and a Group B nuclear receptor ligand binding domain comprising a substitution mutation according to the invention. Preferably, the Group B nuclear receptor ligand binding domain comprising a substitution mutation is an ecdysone receptor ligand binding domain comprising a substitution mutation according to the invention.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4RE"), LexA, a Group B nuclear receptor RE, a steroid/thyroid hormone nuclear receptor RE, or a synthetic RE that recognizes a synthetic DNA binding domain. Preferably, the RE is an ecdysone RE (EcRE) comprising a polynucleotide sequence of SEQ ID NO: 17, a GAL4RE comprising a polynucleotide sequence of SEQ ID NO: 18, or a LexA RE (operon, "op") comprising a polynucleotide sequence of SEQ ID NO: 19 ("2XLexAopRR").

A steroid/thyroid hormone nuclear receptor DNA binding domain, activation domain or response element according to the invention may be obtained from a steroid/thyroid hormone nuclear receptor selected from the group consisting of thyroid hormone receptor α (TRα), thyroid receptor 1 (c-erbA-1), thyroid hormone receptor β (TRβ), retinoic acid receptor α (RARα), retinoic acid receptor β (RARβ, HAP), retinoic acid receptor γ (RARγ), retinoic acid receptor gamma-like (RARD), peroxisome proliferator-activated receptor α (PPARα), peroxisome proliferator-activated receptor β (PPARβ), peroxisome proliferator-activated receptor δ (PPARδ, NUC-1), peroxisome proliferator-activator related receptor (FFAR), peroxisome proliferator-activated receptor γ (PPARγ), orphan receptor encoded by non-encoding strand of thyroid hormone receptor α (REVERBα), v-erb A related receptor (EAR-1), v-erb related receptor (EAR-1A), γ), orphan receptor encoded by non-encoding strand of thyroid hormone receptor β (REVERBβ), v-erb related receptor (EAR-1β), orphan nuclear receptor BD73 (BD73), rev-erbA-related receptor (RVR), zinc finger protein 126 (HZF2), ecdysone-inducible protein E75 (E75), ecdysone-inducible protein E78 (E78), *Drosophila* receptor 78 (DR-78), retinoid-related orphan receptor α (RORα), retinoid Z receptor α (RZRα), retinoid related orphan receptor β (RORβ), retinoid Z receptor β (RZRβ), retinoid-related orphan receptor γ (RORγ), retinoid Z receptor γ (RZRγ), retinoid-related orphan receptor (TOR), hormone receptor 3 (HR-3), *Drosophila* hormone receptor 3 (DHR-3), *manduca* hormone receptor (MHR-3), *Galleria* hormone receptor 3 (GHR-3), *C. elegans* nuclear receptor 3 (CNR-3), *Choristoneura* hormone receptor 3 (CHR-3), *C. elegans* nuclear receptor 14 (CNR-14), ecdysone receptor (ECR), ubiquitous receptor (UR), orphan nuclear receptor (OR-1), NER-1, receptor-interacting protein 15 (RIP-15), liver X receptor β (LXRβ), steroid hormone receptor like protein (RLD-1), liver X receptor (LXR), liver X receptor α (LXRα), farnesoid X receptor (FXR), receptor-interacting protein 14 (RIP-14) HRR-1, vitamin D receptor (VDR), orphan nuclear receptor (ONR-1), pregnane X receptor (PXR), steroid and xenobiotic receptor (SXR), benzoate X receptor (BXR), nuclear receptor (MB-67), constitutive androstane receptor 1 (CAR-1), constitutive androstane receptor α (CARα), constitutive androstane receptor 2 (CAR-2) constitutive androstane receptor β (CARβ), *Drosophila* hormone receptor 96 (DHR-96), nuclear hormone receptor 1 (NHR-1), hepatocyte nuclear factor 4 (HNF-4), hepatocyte nuclear factor 4G (HNF-4G) hepatocyte nuclear factor 4B (HNF-4B), hepatocyte nuclear factor 4D (HNF-4D, DHNP-4), retinoid X receptor α (RXRα), retinoid X receptor β (RXRβ), H-2 region II binding protein (H-2RIIBP), nuclear receptor co-regulator-1 (RCoR-1), retinoid X receptor γ (RXRγ), Ultraspiracle (USP), 2C1 nuclear receptor, chorion factor 1 (CF-1), testicular receptor 2 (TR2), testicular receptor 2-11 (TR2-11), testicular receptor 4 (TR4), TAK-1, *Drosophila* hormone receptor (DHR78), Tailless (TLL), tailless homolog (TLX), XTLL, chicken ovalbumin upstream promoter transcription factor I (COUP-TFI), chicken ovalbumin upstream promoter transcription factor A (COUP-TPA), EAR-3, SVP-44, chicken ovalbumin upstream promoter transcription factor II (COUP-TFII), chicken ovalbumin upstream promoter transcription factor B (COUP-TFB), ARP-1, SVP-40, SVP, chicken ovalbumin upstream promoter transcription factor III (COUP-TFIII), chicken ovalbumin upstream promoter transcription factor G (COUP-TFG), SVP-46, EAR-2, estrogen receptor α (ERα), estrogen receptor β (ERβ), estrogen related receptor 1 (ERR1), estrogen related receptor α (ERRα) estrogen related receptor 2 (ERR2), estrogen related receptor β (ERRβ), glucocorticoid receptor (GR), mineralocorticoid receptor (MR), progesterone receptor (PR), androgen receptor (AR), nerve growth factor induced gene B (NGFI-B), nuclear receptor similar to Nur-77 (TRS), N10, Orphan receptor (NUR-77), Human early response gene (NAK-1), Nurr related factor (NURR-1), a human immediate-early response gene (NOT), regenerating liver nuclear receptor 1 (RNR-1), hematopoietic zinc finger 3 (HZF-3), Nur related protein-1 (TINOR), Nuclear orphan receptor 1 (NOR-1), NOR1 related receptor (MINOR), *Drosophila* hormone receptor 38 (DHR-38), *C. elegans* nuclear receptor 8 (CNR-8), C48D5, steroidogenic factor 1 (SF1), endozepine-like peptide (ELP), fushi tarazu factor 1 (FTZ-F1), adrenal 4 binding protein (AD4BP), liver receptor homolog (LRH-1), Ftz-F1-related orphan receptor A (xFFrA), Ftz-F1-related orphan receptor B (xFFrB), nuclear receptor related to LRH-1 (FFLR), nuclear receptor related to LRH-1 (PHR), fetoprotein transcription factor (FTF), germ cell nuclear factor (GCNFM), retinoid receptor-related testis-associated receptor (RTR), knirps (KNI), knirps related (KNRL), Embryonic gonad (EGON), *Drosophila* gene for ligand dependent nuclear receptor (EAGLE), nuclear receptor similar to trithorax (ODR7), Trithorax, dosage sensitive sex reversal adrenal hypoplasia congenita critical region chromosome X gene (DAX-1), adrenal hypoplasia congenita and hypogonadotropic hypogonadism (AHCH), and short heterodimer partner (SHP).

Thus, the present invention also provides a gene expression cassette comprising: i) a response element comprising a domain recognized by a polypeptide comprising a DNA binding domain; ii) a promoter that is activated by a polypeptide comprising a transactivation domain; and iii) a gene whose expression is to be modulated.

Genes of Interest for use in Applicants' gene expression cassettes may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for use in Applicants' ene expression cassettes include, but are not limited to: genes encoding therapeutically desirable polypeptides or products that nay be used to treat a condition, a disease, a disorder, a dysfunction, a genetic defect, such as monoclonal antibodies, enzymes, proteases, cytokines, interferons, insulin, erythropoietin, clotting factors, other blood factors or components, viral vectors for gene therapy, virus for vaccines, targets for drug discovery, functional genomics, and proteomics analyses and applications, and the like.

For purposes of this invention, nuclear receptors and Group B nuclear receptors also include synthetic and chimeric nuclear receptors and Group B nuclear receptors and their homologs.

Polynucleotide of the Invention

The novel nuclear receptor-based inducible gene expression system of the invention comprises at least one gee expression cassette comprising a polynucleotide that encodes a Group B nuclear receptor ligand binding domain comprising a substitution mutation. These gene expression cassettes, the polynucleotides they comprise, and the polypeptides they encode are useful as components of a nuclear receptor-based gene expression system to modulate the expression of a gene within a host cell. Thus, the present invention also provides an isolated polynucleotide that encodes a Group B nuclear receptor ligand binding domain comprising a substitution mutation.

In a specific embodiment, the Group B nuclear receptor ligand binding domain is encoded by a polynucleotide comprising a codon mutation that results in a substitution of an amino acid residue, wherein the amino acid residue is at a position equivalent or analogous to an amino acid residue selected from the group consisting of a) 401 or 429 of SEQ ID NO: 1, b) 401 and 429 of SEQ ID NO: 1, c) 337, 344, 355, 385, 431, 442, 462, 470, 472, 473, 495, 500, 511, 516, or 528 of SEQ ID NO: 2, d) 321, 322, and 323 of SEQ ID NO: 2, e) 450, 451, and 452 of SEQ ID NO: 2, f) 455, 456, 457, and 458 of SEQ ID NO: 2, g) 470, 472, and 473 of SEQ ID NO: 2, h) 475, 476, 477, 478, and 479 of SEQ ID NO: 2, and i) 481, 482, and 483 of SEQ ID NO: 2. In a preferred embodiment, the Group B nuclear receptor ligand binding domain is from a retinoid X receptor.

In another specific embodiment, the Group B nuclear receptor ligand binding domain is encoded by a polynucleotide comprising a codon mutation that results in a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an aspartic acid residue at a position equivalent or analogous to amino acid residue 401 of SEQ ID NO: 1, and a serine residue at a position equivalent to or analogous to amino acid of amino acid residue 429 of SEQ ID NO: 1, d) a serine residue at a position equivalent or analogous to amino acid residues 337, 495, 500, or 528 of SEQ ID NO: 2, e) an asparagine residue at a position equivalent or analogous to amino acid residue 344 of SEQ ID NO: 2, f) an arginine residue at a position equivalent to or analogous to amino acid of amino acid residues 355 or 511 of SEQ ID NO: 2, g) an alanine residue at a position equivalent or analogous to amino acid residues 385 or 470 of SEQ ID NO: 2, h) a leucine residue at a position equivalent or analogous to amino acid residue 431 or 462 of SEQ ID NO: 2, i) a lysine residue at a position equivalent to or analogous to amino acid residue 442 of SEQ ID NO: 2, j) an aspartic acid residue at a position equivalent or analogous to amino acid residue 472 of SEQ ID NO: 2, k) a glutamic acid at a position equivalent to or analogous to amino acid residue 473 of SEQ ID NO: 2, l) a valine residue at a position equivalent to or analogous to amino acid residue 516 of SEQ ID NO: 2, m) a leucine residue at a position equivalent to or analogous to amino acid residue 321 of SEQ ID NO: 2, an arginine residue at a position equivalent to or analogous to amino acid residue 322 of SEQ ID NO: 2, and a valine residue at a position equivalent to or analogous to amino acid residue 323 of SEQ ID NO: 2, n) a glutamic acid residue at a position equivalent to or analogous to amino acid residue 450 of SEQ ID NO: 2, a valine residue at a position equivalent to or analogous to amino acid residue 451 of SEQ ID NO: 2, and an arginine residue at a position equivalent to or analogous to amino acid residue 452 of SEQ ID NO: 2, o) a lysine residue at a position equivalent to or analogous to amino acid residue 455 of SEQ ID NO: 2, a serine residue at a position equivalent to or analogous to amino acid residue 456 of SEQ ID NO: 2, an alanine residue at a position equivalent to or analogous to amino acid residue 457 of SEQ ID NO: 2, and a glutamine residue at a position equivalent to or analogous to amino acid residue 458 of SEQ ID NO: 2, p) an alanine residue at a position equivalent to or analogous to amino acid residue 470 of SEQ ID NO: 2, a aspartic acid residue at a position equivalent to or analogous to amino acid residue 472 of SEQ ID NO: 2, and a tyrosine residue at a position equivalent to or analogous to amino acid residue 473 of SEQ ID NO: 2, q) a threonine residue at a position equivalent to or analogous to amino acid residues 475, 477, and 478 of SEQ ID NO: 2, an arginine residue at a position equivalent to or analogous to amino acid residue 476 of SEQ ID NO: 2, and a histidine residue at a position equivalent to or analogous to amino acid residue 479 of SEQ ID NO: 2, or r) an aspartic acid residue at a position equivalent to or analogous to amino acid residue 481 of SEQ ID NO: 2, a glutamic acid residue at a position equivalent to or analogous to amino acid of amino acid residue 482 of SEQ ID NO: 2, and a proline residue at a position equivalent to or analogous to amino acid residue 483 of SEQ ID NO: 2. In a preferred embodiment, the Group B nuclear receptor ligand binding domain is from a retinoid X receptor.

In another specific embodiment, the Group B nuclear receptor ligand binding domain comprising a substitution mutation is a retinoid X receptor ligand binding domain comprising a substitution mutation encoded by a polynucleotide comprising a codon mutation or codon mutations that results in a substitution mutation selected from the group consisting of a) E401D or G429S of SEQ ID NO: 1, b) E401D and G429S of SEQ ID NO: 1, c) T337S, D344N, K355R, S385A, M431L, R442K, V462L, S470A, B471D, T473E, A495S, E500S, K511R, T516V, or A528S of SEQ ID NO: 2, d) G321L, P322R, and G323V of SEQ ID NO: 2, e) D450E, A451V, and K452R of SEQ ID NO: 2, t) S455K, N456S, P457A, and S458Q of SEQ ID NO: 2, g) S470A, E472D, and T473Y of SEQ ID NO: 2, h) C475T, K476R, Q477T, K478T, and Y479H of SEQ ID NO: 2, and i) E481D, Q482E, and Q483P of SEQ ID NO: 2.

The present invention also provides an isolated polynucleotide that encodes a polypeptide selected from the group consisting of a) a polypeptide comprising a transactivation domain, a DNA-binding domain, and a Group B nuclear receptor ligand binding domain comprising a substitution mutation according to the invention; b) a polypeptide comprising a DNA-binding domain and a Group B nuclear receptor ligand binding domain comprising a substitution mutation according to the invention; and c) a polypeptide comprising a transactivation domain and a Group B nuclear receptor ligand binding domain comprising a substitution mutation according to the invention.

In a specific embodiment, the isolated polynucleotide encodes a hybrid polypeptide selected from the group consisting of a) a hybrid polypeptide comprising a transactivation domain, a DNA-binding domain, and a Group B nuclear receptor ligand binding domain comprising a substitution mutation according to the invention; b) a hybrid polypeptide comprising a DNA-binding domain and a Group B nuclear receptor ligand binding domain comprising a substitution mutation according to the invention; and c) a hybrid polypeptide comprising a transactivation domain and a Group B nuclear receptor ligand binding domain comprising a substitution mutation according to the invention.

The present invention also relates to an isolated polynucleotide encoding a Group B nuclear receptor ligand binding domain comprising a substitution mutation, wherein the substitution mutation affects ligand binding activity or ligand sensitivity of the Group B nuclear receptor ligand binding domain.

In particular, the present invention relates to an isolated polynucleotide encoding a Group B nuclear receptor ligand binding domain comprising a substitution mutation, wherein the substitution mutation reduces ligand binding activity or ligand sensitivity of the Group B nuclear receptor ligand binding domain.

In a specific embodiment the present invention relates to an isolated polynucleotide encoding a Group B nuclear receptor ligand binding domain comprising a substitution mutation, wherein the substitution mutation reduces steroid binding activity or steroid sensitivity of the Group B nuclear receptor ligand binding domain. Preferably, the isolated polynucleotide comprises a codon mutation that results in a substitution of an amino acid residue, wherein the amino acid residue is at a position equivalent or analogous to a) amino acid residue 401 or 429 of SEQ ID NO: 1, or b) amino acid residue 344, 431, 442, 495, 511, or 528 of SEQ ID NO: 2. More preferably, the isolated polynucleotide comprises a codon mutation that results in a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an asparagine residue at a position equivalent or analogous to amino acid residue 344 of SEQ ID NO: 2, d) a leucine residue at a position equivalent or analogous to amino acid residue 431 of SEQ ID NO: 2, e) a lysine residue at a position equivalent or analogous to amino acid residue 442 of SEQ ID NO: 2, f) a serine residue at a position equivalent or analogous to amino acid residue 495 or 528 of SEQ ID NO: 2, or g) an arginine residue at a position equivalent or analogous to amino acid residue 511 of SEQ ID. NO: 2. Even more preferably, the isolated polynucleotide comprises a codon mutation that results in a substitution mutation selected from the group consisting of a) E401D or G429S of SEQ ID NO: 1, and b) D344N, M431L, R442K, A495S, K511R, or A528S of SEQ ID NO: 2.

In a specific embodiment, the present invention relates to an isolated polynucleotide encoding a Group B nuclear receptor ligand binding domain comprising a substitution mutation, wherein the substitution mutation reduces non-steroid ligand binding activity or ligand sensitivity of the Group B nuclear receptor ligand binding domain. Preferably, the isolated polynucleotide comprises a codon mutation that results in a substitution of an amino acid residue, wherein the amino acid residue is at a position equivalent or analogous to a) amino acid residue 401 or 429 of SEQ ID NO: 1, orb) amino acid residue 344, 431, 442, 495, 511, or 528 of SEQ ID NO: 2. More preferably, the isolated polynucleotide comprises a codon mutation that results in a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an asparagine residue at a position equivalent or analogous to amino acid residue 344 of SEQ ID NO: 2, d) a leucine residue at a position equivalent or analogous to amino acid residue 431 of SEQ ID NO: 2, e) a lysine residue at a position equivalent or analogous to amino acid residue 442 of SEQ ID NO: 2, f) a serine residue at a position equivalent or analogous to amino acid residue 495 or 528 of SEQ ID NO: 2, or g) an arginine residue at a position equivalent or analogous to amino acid residue 511 of SEQ ID NO: 2. Even more preferably, the isolated polynucleotide comprises a codon mutation that results in a substitution mutation selected from the group consisting of a) E401D or G429S of SEQ ID NO: 1, and b) D344N, M431L, R442K, A495S, K511R or A528S of SEQ ID NO: 2.

In addition, the present invention also relates to an isolated polynucleotide encoding a Group B nuclear receptor ligand binding domain comprising a substitution mutation, wherein the substitution mutation enhances ligand binding activity or ligand sensitivity of the Group B nuclear receptor ligand binding domain.

In a specific embodiment, the present invention relates to an isolated polynucleotide encoding a Group B nuclear receptor ligand binding domain comprising a substitution mutation, wherein the substitution mutation enhances steroid binding activity or steroid sensitivity of the Group B nuclear receptor ligand binding domain. Preferably, the isolated polynucleotide con rises a codon mutation that results in a substitution of an amino acid residue at a position equivalent or analogous to amino acid residue selected from the group consisting of a) 401 or 429 of SEQ ID NO: 1, b) 401 and 429 of SEQ ID NO: 1, c) 337, 355, 385, 462, 470, 472, 473, or 500 of SEQ ID NO: 2, d) 321, 322, and 323 of SEQ ID NO: 2, e) 450, 451, and 452 of SEQ ID NO: 2, f) 455, 456, 457, and 458 of SEQ ID NO: 2, g) 470, 472, and 473 of SEQ ID NO: 2, h) 475, 476, 477, 478, and 479 of SEQ ID NO: 2, and i) 481, 482, and 483 of SEQ ID NO: 2. More preferably, the isolated polynucleotide comprises a codon mutation that results in a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an aspartic acid residue at a position equivalent or analogous to amino acid residue 401 of SEQ ID NO: 1, and a serine residue at a position equivalent to or analogous to amino acid residue 429 of SEQ ID NO: 1, d) a serine residue at a position equivalent or analogous to amino acid residue 337 or 500 of SEQ ID NO: 2, c) an arginine residue at a position equivalent to or analogous to amino acid residue 355 of SEQ ID NO: 2, f) a alanine residue at a position equivalent or analogue to amino acid residue 385 or 470 of SEQ ID NO: 2, g) a leucine residue at a position equivalent or analogous to amino acid residue 462 of SEQ ID NO: 2, h) an aspartic acid residue at a position equivalent or analogous to amino acid residue 472 of SEQ ID NO: 2, i) a glutamic acid at a position equivalent to or analogous to amino acid residue 473 of SEQ ID NO: 2, j) a leucine residue at a position equivalent or analogous to amino acid residue 321 of SEQ ID NO: 2, an arginine residue at a position equivalent or analogous to amino acid residue 322 of SEQ ID NO: 2, and a valine residue at a position equivalent or analogous to amino acid residue 323 of SEQ ID NO: 2, k) a glutamic acid residue at a position equivalent to or analogous to amino acid residue 450 of SEQ ID NO: 2, a valine residue at a position equivalent to or analogous to amino acid residue 451 of SEQ ID NO: 2, and an arginine residue at a position equivalent to or analogous to amino acid residue 452 of SEQ ID NO: 2, l) a lysine residue at a position equivalent to or analogous to amino acid residue 455 of SEQ ID NO: 2, a serine residue at a position equivalent to or analogous to amino acid residue 456 of SEQ ID NO: 2, an alanine residue at a position equivalent to or analogous to amino acid residue 457 of SEQ ID NO: 2, and a glutamine residue at a position equivalent to or analogous to amino acid residue 458 of SEQ ID NO: 2, m) an alanine residue at a position equivalent to or analogous to amino acid residue 470 of SEQ ID NO: 2, an aspartic acid residue at a position equivalent to or analogous to amino acid residue 472 of SEQ ID NO: 2, and a tyrosine residue at a position equivalent to or analogous to amino acid residue 473 of SEQ ID NO: 2, a) a threonine residue at a position equivalent to or analogous to amino acid residues 475, 477, and 478 of SEQ ID NO: 2, an arginine residue at a position equivalent to or analogous to amino acid residue 476 of SEQ ID NO: 2, and a histidine residue at a position equivalent to or analogous to amino acid residue 479 of SEQ ID NO: 2, or o) an aspartic acid residue at a position equivalent to or analogous to amino acid residue 481 of SEQ ID NO: 2, a glutamic acid residue at a position equivalent to or analogous to amino acid residue 482 of SEQ ID NO: 2, and a proline residue at a position equivalent to or analogous to amino acid residue 483 of SEQ ID NO: 2. Even more preferably, the isolated polynucleotide comprises a codon mutation or codon mutations that results in a substitution mutation selected from the group consisting of a) B401D or G429S of SEQ ID NO: 1, b) E401D and G429S of SEQ ID NO: 1, c) T337S, K355R, S385A, V462L, S470A, E471D, T473B, or E500S of SEQ ID NO: 2, d) G321L, P322R, and G323V of SEQ ID NO: 2, e) D450E, A451V, and K452R of SEQ ID NO: 2, f) S455K, N456S, P457A, and S458Q of SEQ ID NO: 2, g) S470A, B472D, and T473Y of SEQ ID NO: 2, b) C475T, K476R, Q477T, K478T, and Y479H of SEQ ID NO: 2, and i) E481D, Q482E, and Q483P of SEQ ID NO: 2.

In another specific embodiment, the present invention relates to an isolated polynucleotide encoding a Group B nuclear receptor ligand binding domain comprising a substitution mutation, wherein the substitution mutation enhances non-steroid binding activity or no-steroid sensitivity of the Group B nuclear receptor ligand binding domain. Preferably, the isolated polynucleotide comprises a codon mutation that results in a substitution of an amino acid residue at a position equivalent or analogous to amino acid residue selected from the group consisting of a) 401 or 429 of SEQ ID NO: 1, b) 401 and 429 of SEQ ID NO: 1, c) 337, 355, 385, 462, 470, 472, 473, or 500 of SEQ ID NO: 2, d) 321, 322, and 323 of SEQ ID NO: 2, e) 450, 451, and 452 of SEQ ID NO: 2, f) 455, 456, 457, and 458 of SEQ ID NO: 2, g) 470, 472, and 473 of SEQ ID NO: 2, h) 475, 476, 477, 478, and 479 of SEQ ID NO: 2, and i) 481, 482, and 483 of SEQ ID NO: 2. More preferably, the isolated polynucleotide comprises a codon mutation that results in a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an aspartic acid residue at a position equivalent or analogous to amino acid residue 401 of SEQ ID NO: 1, and a serine residue at a position equivalent to or analogous to amino acid residue 429 of SEQ ID NO: 1, d) a serine residue at a position equivalent or analogous to amino acid residue 337 or 500 of SEQ ID NO: 2, e) an arginine residue at a position equivalent to or analogous to amino acid residue 355 of SEQ ID NO: 2, f) an alanine residue at a position equivalent or analogous to amino acid residue 385 or 470 of SEQ ID NO: 2, g) a leucine residue at a position equivalent or analogous to amino acid residue 462 of SEQ ID NO: 2, h) an aspartic acid residue at a position equivalent or analogous to amino acid residue 472 of SEQ ID NO: 2, i) a glutamic acid at a position equivalent to or analogous to amino acid residue 473 of SEQ ID NO: 2, j) a leucine residue at a position equivalent or analogous to amino acid residue 321 of SEQ ID NO: 2, an arginine residue at a position equivalent or analogous to amino acid residue 322 of SEQ ID NO: 2, and a valine residue at a position equivalent or analogous to amino acid residue 323 of SEQ ID NO: 2, k) a glutamic acid residue at a position equivalent to or analogous to amino acid residue 450 of SEQ ID NO: 2, a valine residue at a position equivalent to or analogous to amino acid residue 451 of SEQ ID NO: 2, and an arginine residue at a position equivalent to or analogous to amino acid residue 452 of SEQ ID NO: 2, l) a lysine residue at a position equivalent to or analogous to amino acid residue 455 of SEQ ID NO: 2, a serine residue at a position equivalent to or analogous to amino acid residue 456 of SEQ ID NO: 2, an alanine residue at a position equivalent to or analogous to amino acid residue 457 of SEQ ID NO: 2, and a glutamine residue at a position equivalent to or analogous to amino acid residue 458 of SEQ ID NO: 2, m) an alanine residue at a position equivalent to or analogous to amino acid residue 470 of SEQ ID NO: 2, an aspartic acid residue at a position equivalent to or analogous to amino acid residue 472 of SEQ ID NO: 2, and a tyrosine residue at a position equivalent to or analogous to amino acid residue 473 of SEQ ID NO 2, n) a threonin residue at a position equivalent to or analogous to amino acid residues 475, 477, and 478 of SEQ ID NO: 2, an arginine residue at a position equivalent to or analogous to amino acid residue 476 of SEQ ID NO: 2, and a histidine residue at a position equivalent to or analogous to amino acid residue 479 of SEQ ID NO: 2, or o) an aspartic acid residue at a position equivalent to or analogous to amino acid residue 481 of SEQ ID NO: 2, a glutamic acid residue at a position equivalent to or analogous to amino acid residue 482 of SEQ ID NO: 2, and a proline residue at a position equivalent to or analogous to amino acid residue 483 of SEQ ID NO: 2. Even more preferably, the isolated polynucleotide comprises a codon mutation or codon mutations that results in a substitution mutation selected from the group consisting of a) E401D or G429S of SEQ ID NO: 1, b) E401D and G429S of SEQ ID NO: 1, c) T337S, K355R, S385A, V462L, S470A, E471D, T473E, or E500S of SEQ ID NO: 2, d) G321L, P322R, and G323V of SEQ ID NO: 2, c) D450E, A451V, and K452R of SEQ ID NO: 2, f) S455K, N456S, P457A, and S458Q of SEQ ID NO: 2, g) S470A, E472D, and T473Y of SEQ ID NO: 2, h) C475T, K476R, Q477T, K478T, and Y479H of SEQ ID NO: 2, and i) E481D, Q482B, and Q483P of SEQ ID NO: 2.

In another specific embodiment, the present invention relates to an isolated polynucleotide encoding a Group B nuclear receptor ligand binding domain comprising a substitution mutation, wherein the substitution mutation enhances both steroid binding activity or steroid sensitivity and non-steroid binding activity or non-steroid sensitivity of the Group B ligand binding domain.

In another specific embodiment, the present invention also relates to an isolated polynucleotide encoding a Group B nuclear receptor ligand binding domain comprising a substitution mutation, wherein the substitution mutation increases ligand sensitivity of a heterodimer comprising the Group B nuclear receptor ligand binding domain comprising a substitution mutation and a dimerization partner. In a specific embodiment, the dimerization partner is an ecdysone receptor polypeptide. In another specific embodiment, the dimerization partner is a truncated EcR polypeptide.

In addition, the present invention relates to an expression vector comprising a polynucleotide according the invention, operatively linked to a transcription regulatory element. Preferably, the polynucleotide encoding a nuclear receptor ligand binding domain comprising a substitution mutation is operatively linked with an expression control sequence permitting expression of the nuclear receptor ligand binding domain in an expression competent host cell. The expression control sequence may comprise a promote that is functional in the host cell in which expression is desired. The vector may be a plasmid DNA molecule or a viral vector. Preferred viral vectors include retrovirus, adenovirus, adeno-associated virus, herpes virus, and vaccinia virus. The invention further relates to a replication defective recombinant virus comprising in its genome, the polynucleotide encoding a nuclear receptor ligand binding domain comprising a substitution mutation as described above. Thus, the present invention also relates to an isolated host cell comprising such an expression vector, wherein the transcription regulatory element is operative in the host cell.

The present invention also relates to an isolated polypeptide encoded by a polynucleotide according to the invention.

Polypeptides of the Invention

The novel nuclear receptor-based inducible gene expression system of the invention comprises at least one gene expression cassette comprising a polynucleotide that encodes a polypeptide comprising a Group B nuclear receptor ligand binding domain comprising a substitution mutation. Thus, the present invention also provides an isolated polypeptide comprising a Group B nuclear receptor ligand binding domain comprising a substitution mutation according to the invention.

In another specific embodiment, the Group B nuclear receptor ligand binding domain comprises a substitution mutation at a position equivalent or analogous to amino acid residue a) 401 or 429 of SEQ ID NO: 1, b) 401 and 429 of SEQ ID NO: 1, c) 337, 344, 355, 385, 431, 442, 462, 470, 472, 473, 495, 500, 511, 516, or 528 of SEQ ID NO: 2, d) 321, 322, and 323 of SEQ ID NO: 2, e) 450, 451, and 452 of SEQ ID NO: 2, f) 455, 456, 457, and 458 of SEQ ID NO: 2, g) 470, 472, and 473 of SEQ ID NO: 2, h) 475, 476, 477, 478, and 479 of SEQ ID NO: 2, and i) 481, 482, and 483 of SEQ ID NO: 2.

Preferably, the Group B nuclear receptor ligand binding domain comprises a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an aspartic acid residue at a position equivalent or analogous to amino acid residue 401 of SEQ ID NO: 1, and a serine residue at a position equivalent to or analogous to amino acid residue 429 of SEQ ID NO: 1, d) a serine residue at a position equivalent or analogous to amino acid residue 337, 495, 500, or 528 of SEQ ID NO: 2, e) an asparagine residue at a position equivalent or analogous to amino acid residue 344 of SEQ ID NO: 2, f) an arginine residue at a position equivalent to or analogous to amino acid residue 355 or 511 of SEQ ID NO: 2, g) an alamine residue at a position equivalent or analogous to amino acid residue 385 or 470 of SEQ ID NO: 2, h) a leucine residue at a position equivalent or analogous to amino acid residue 431 or 462 of SEQ ID NO: 2, i) a lysine residue at a position equivalent to or analogous to amino acid residue 442 of SEQ ID NO: 2, j) an aspartic acid residue at a position equivalent or analogous to amino acid residue 472 of SEQ ID NO: 2, k) a glutamic acid at a position equivalent to or analogous to amino acid residue 473 of SEQ ID NO: 2, l) a valine residue at a position equivalent to or analogous to amino acid residue 516 of SEQ ID NO: 2, m) a leucine residue at a position equivalent to or analogous to amino acid residue 321 of SEQ ID NO: 2, an arginine residue at a position equivalent to or analogous to amino acid residue 322 of SEQ ID NO: 2, and a valine residue at a position equivalent to or analogous to amino acid residue 323 of SEQ ID NO: 2, n) a glutamic acid residue at a position equivalent to or analogous to amino acid residue 450 of SEQ ID NO: 2, a valine residue at a position equivalent to or analogous to amino acid residue 451 of SEQ ID NO: 2, and an arginine residue at a position equivalent to or analogous to amino acid residue 452 of SEQ ID NO: 2, o) a lysine residue at a position equivalent to or analogous to amino acid residue 455 of SEQ ID NO: 2, a serine residue at a position equivalent to or analogous to amino acid residue 456 of SEQ ID NO: 2, an alanine residue at a position equivalent to or analogous to amino acid residue 457 of SEQ ID NO: 2, and a glutamine residue at a position equivalent or analogous to amino acid residue 458 of SEQ ID NO: 2, p) an alanine residue at a position equivalent to or analogous to amino acid residue 470 of SEQ ID NO: 2, an aspartic acid residue at a position equivalent to or analogous to amino acid residue 472 of SEQ ID NO: 2, and a tyrosine residue at a position equivalent to or analogous to amino acid residue 473 of SEQ ID NO: 2, q) a threonine residue at a position equivalent to or analogous to amino acid residues 475, 477, and 478 of SEQ ID NO: 2, an arginine residue at a position equivalent to or analogous to amino acid residue 476 of SEQ ID NO: 2, and a histidine residue at a position equivalent to or analogous to amino acid residue 479 of SEQ ID NO: 2, or r) an aspartic acid residue at a position equivalent to or analogous to amino acid residue 481 of SEQ ID NO: 2, a glutamic acid residue at a position equivalent to or analogous to amino acid residue 482 of SEQ ID NO: 2, and a proline residue at a position equivalent to or analogous to amino acid residue 483 of SEQ ID NO: 2. In a preferred embodiment, the Group R nuclear receptor ligand binding domain is from a retinoid X receptor.

In another specific embodiment, the Group B nuclear receptor ligand binding domain comprising a substitution mutation is a retinoid X receptor ligand binding domain comprising a substitution mutation, wherein the substitution mutation is selected from the group consisting of a) B401D or G429S of SEQ ID NO: 1, b) E401D and G429S of SEQ ID NO: 1, c) T337S, D344N, K355R, S385A, M431L, R442K, V462L, S470A, B471D, T473E, A495S, E500S, K511R, T516V, or A528S of SEQ ID NO: 2, d) G321L, P322R, and 0323V of SEQ ID NO: 2, e) D450E, A451V, and K452R of SEQ ID NO: 2, f) S455K, N456S, P457A, and S458Q of SEQ ID NO: 2, g) S470A, E472D, and T473Y of SEQ ID NO: 2, h) C475T, K476R, Q477T, K478T, and Y479H of SEQ ID NO: 2, and i) B481D, Q482E, and Q483P of SEQ ID NO: 2.

The present invention also provides an isolated polypeptide selected from the group consisting of a) an isolated polypeptide comprising a transactivation domain, a DNA-binding domain, and a Group B nuclear receptor ligand binding domain comprising a substitution mutation according to the invention; b) an isolated polypeptide comprising a DNA-binding domain and a Group B nuclear receptor ligand binding domain comprising a substitution mutation according to the invention; and c) an isolated polypeptide comprising a transactivation domain and a Group B nuclear receptor ligand binding domain comprising a substitution mutation according to the invention. In a preferred embodiment, the Group B nuclear receptor ligand binding domain is from a retinoid X receptor.

The present invention also provides an isolated hybrid polypeptide selected from the group consisting of a) an isolated hybrid polypeptide comprising a transactivation domain, a DNA-binding domain, and a Group B nuclear receptor ligand binding domain comprising a substitution mutation according to the invention; b) an isolated hybrid polypeptide comprising a DNA-binding domain and a Group B nuclear receptor ligand binding domain comprising a substitution mutation according to the invention; and e) an isolated hybrid polypeptide comprising a transactivation domain and a Group B nuclear receptor ligand binding domain comprising a substitution mutation according to the invention. In a preferred embodiment, the Group B nuclear receptor ligand binding domain is from a retinoid X receptor.

The present invention also provides an isolated polypeptide comprising a Group B nuclear receptor ligand binding domain comprising a substitution mutation that affects ligand binding activity or ligand sensitivity of the Group B nuclear receptor ligand binding domain.

In particular, the present invention relates to an isolated Group B nuclear receptor polypeptide comprising a ligand binding domain comprising a substitution mutation that reduces ligand binding activity or ligand sensitivity of the Group B nuclear receptor ligand binding domain.

In a specific embodiment, the present invention relates to an isolated polypeptide comprising a Group B nuclear receptor ligand binding domain comprising a substitution mutation, wherein the substitution mutation reduces steroid binding activity or steroid sensitivity of the Group B nuclear receptor ligand binding domain. Preferably, the isolated polypeptide comprises a substitution of an amino acid residue at a position equivalent or analogous to a) amino acid residue 401 or 429 of SEQ ID NO: 1, or b) amino acid residue 344, 431, 442, 495, 511, or 528 of SEQ ID NO: 2. More preferably, the isolated polypeptide comprises a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an asparagine residue at a position equivalent or analogous to amino acid residue 344 of SEQ ID NO: 2, d) a leucine residue at a position equivalent or analogous to amino acid residue 431 of SEQ ID NO: 2, e) a lysine residue at a position equivalent or analogous to amino acid residue 442 of SEQ ID NO: 2, f) a serine residue at a position equivalent or analogous to amino acid residue 495 or 528 of SEQ ID NO: 2, or g) an arginine residue at a position equivalent or analogous to amino acid residue 511 of SEQ ID NO: 2. Even more preferably, the isolated polypeptide comprises a substitution mutation selected from the group consisting of a) E401D or G429S of SEQ ID NO: 1, and b) D344N, M431L, R442K, A495S, K511R, or A528S of SEQ ID NO: 2.

In a specific embodiment, the present invention relates to an isolated polypeptide comprising a Group B nuclear receptor ligand binding domain comprising a substitution mutation, wherein the substitution mutation reduces non-steroid ligand binding activity or ligand sensitivity of the Group B nuclear receptor ligand binding domain. Preferably, the isolated polypeptide comprises a substitution of a amino acid residue at a position equivalent or analogous to a) amino acid residue 401 or 429 of SEQ ID NO: 1, or b) amino acid residue 344, 431, 442, 495, 511, or 528 of SEQ ID NO: 2. More preferably, the isolated polypeptide comprises a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an asparagine residue at a position equivalent or analogous to amino acid residue 344 of SEQ ID NO: 2, d) a leucine residue at a position equivalent or analogous to amino acid residue 431 of SEQ ID NO: 2, e) a lysine residue at a position equivalent or analogous to amino acid residue 442 of SEQ ID NO: 2, f) a serine residue at a position equivalent or analogous to amino acid residue 495 or 528 of SEQ ID NO: 2, or g) an arginine residue at a position equivalent or analogous to amino acid residue 511 of SEQ ID NO: 2. Even more preferably, the isolated polypeptide comprises a substitution mutation selected from the group consisting of a) E401D or G429S of SEQ ID NO: 1, and b) D344N, M431L, R442K, A495S, K511R, or A528S of SEQ ID NO: 2.

In addition, the present invention relates to an isolated polypeptide comprising a Group B nuclear receptor ligand binding domain comprising a substitution mutation that enhances ligand binding activity or ligand sensitivity of the Group B nuclear receptor ligand binding domain.

In a specific embodiment, the present invention relates to an isolated polypeptide comprising a Group B nuclear receptor ligand binding domain comprising a substitution mutation that enhances steroid binding activity or steroid sensitivity of the Group B nuclear receptor ligand binding domain. Preferably, the isolated polypeptide comprises a substitution of an amino acid residue at a position equivalent or analogous to amino acid residue selected from the group consisting of a) 401 or 429 of SEQ ID NO: 1, b) 401 and 429 of SEQ ID NO: 1, c) 337, 355, 385, 462, 470, 472, 473, or 500 of SEQ ID NO: 2, d) 321, 322, and 323 of SEQ ID NO: 2, e) 450, 451, and 452 of SEQ ID NO: 2, f) 455, 456, 457, and 458 of SEQ ID NO: 2, g) 470, 472, and 473 of SEQ ID NO: 2, h) 475, 476, 477, 478, and 479 of SEQ ID NO: 2, and i) 481, 482, and 483 of SEQ ID NO: 2. More preferably, the isolated polypeptide comprises a substitution of a) an aspartic acid residue at a position equivalent or analogous to amino acid residue 401 of SEQ ID NO: 1, b) a serine residue at a position equivalent or analogous to amino acid residue 429 of SEQ ID NO 1, c) an aspartic acid residue at a position equivalent or analogous to amino acid residue 401 of SEQ ID NO: 1, and a serine residue at a position equivalent to or analogous to amino acid residue 429 of SEQ ID NO: 1, d) a serine residue at a position equivalent or analogous to amino acid residue 337 or 500 of SEQ ID NO: 2, e) an arginine residue at a position equivalent to or analogous to amino acid residue 355 of SEQ ID NO: 2, t) an alanine residue at a position equivalent or analogous to amino acid residue 385 or 470 of SEQ ID NO: 2, g) a leucine residue at a position equivalent or analogous to amino acid residue 462 of SEQ ID NO: 2, h) an aspartic acid residue at a position equivalent or analogous to amino acid residue 472 of SEQ ID NO: 2, i) a glutamic acid at a position equivalent to or analogous to amino acid residue 473 of SEQ ID NO: 2, j) a leucine residue at a position equivalent or analogous to amino acid residue 321 of SEQ ID NO: 2, an arginine residue at a position equivalent or analogous to amino acid residue 322 of SEQ ID NO: 2, and a valine residue at a position equivalent or analogous to amino acid residue 323 of SEQ ID NO: 2, k) a glutamic acid residue at a position equivalent to or analogous to amino acid residue 450 of SEQ ID NO: 2, a valine residue at a position equivalent to or analogous to amino acid residue 451 of SEQ ID NO: 2, and an arginine residue at a position equivalent to or analogous to amino acid residue 452 of SEQ ID NO: 2, l) a lysine residue at a position equivalent to or analogous to amino acid residue 455 of SEQ ID NO: 2, a serine residue at a position equivalent to or analogous to amino acid residue 456 of SEQ ID NO: 2, an alanine residue at a position equivalent to or analogous to amino acid residue 457 of SEQ ID NO: 2, and a glutamine residue at a position equivalent to or analogous to amino acid residue 458 of SEQ ID NO: 2, m) an alanine residue at a position equivalent to or analogous to amino aid residue 470 of SEQ ID NO: 2, an aspartic acid residue at a position equivalent to or analogous to amino acid residue 472 of SEQ ID NO: 2, and a tyrosine residue at a position equivalent to or analogous to amino acid residue 473 of SEQ ID NO: 2, n) a threonine residue at a position equivalent to or analogous to amino acid residues 475, 477, and 478 of SEQ ID NO: 2, an arginine residue at a position equivalent to or analogous to amino aid residue 476 of SEQ ID NO: 2, and a histidine residue at a position equivalent to or analogous to amino acid residue 479 of SEQ ID NO: 2, or o) an aspartic acid residue at a position equivalent to or analogous to amino acid residue 481 of SEQ ID NO: 2, a glutamic acid residue at a position equivalent to or analogous to amino acid residue 482 of SEQ ID NO: 2, and a proline residue at a position equivalent to or analogous to amino acid residue 483 of SEQ ID NO: 2. Even more preferably, the isolated polypeptide comprises a substitution mutation selected from the group consisting of a) E401D or G429S of SEQ ID NO: 1, b) B401D and G429S of SEQ ID NO: 1, c) T337S, K355R, S385A, V462L, S470A, E471D, T473E, or E500S of SEQ ID NO 2, d) G321L, P322R, and G323V of SEQ ID NO: 2, e) D450B, A451V, and K452R of SEQ ID NO: 2, f) S455K, N456S, P457A, and S458Q of SEQ ID NO: 2, g) S470A, B472D, and T473Y of SEQ ID NO: 2, h) C475T, K476R, Q477T, K478T, and Y479H of SEQ ID NO: 2, and i) B481D, Q482E, and Q483P of SEQ ID NO: 2.

In another specific embodiment, the present invention relates to an isolated polypeptide comprising a Group B nuclear receptor ligand binding domain comprising a substitution mutation that enhances non-steroid binding activity or non-steroid sensitivity of the Group B nuclear receptor ligand binding domain. Preferably, the isolated polypeptide comprises a substitution of an amino acid residue at a position equivalent or analogous to amino acid residue selected from the group consisting of a) 401 or 429 of SEQ ID NO: 1, b) 401 and 429 of SEQ ID NO: 1, c) 337, 355, 385, 462, 470, 472, 473, or 500 of SEQ ID NO: 2, d) 321, 322, and 323 of SEQ ID NO: 2, e) 450, 451, and 452 of SEQ ID NO: 2, f) 455, 456, 457, and 458 of SEQ ID NO: 2, g) 470, 472, and 473 of SEQ ID NO: 2, h) 475, 476, 477, 478, and 479 of SEQ ID NO: 2, and i) 481, 482, and 483 of SEQ ID NO: 2. More preferably, the isolated polypeptide comprises a substitution of a) an aspartic acid residue at a position equivalent or analogous to amino acid residue 401 of SEQ ID NO: 1, b) a serine residue at a position equivalent or analogous to amino acid residue 429 of SEQ ID NO: 1, c) an aspartic acid residue at a position equivalent or analogous to amino acid residue 401 of SEQ ID NO: 1, and a serine residue at a position equivalent to or analogous to amino acid residue 429 of SEQ ID NO: 1, d) a serine residue at a position equivalent or analogous to amino acid residue 337 or 500 of SEQ ID NO: 2, e) an arginine residue at a position equivalent to or analogous to amino acid residue 355 of SEQ ID NO. 2, f) an alanine residue at a position equivalent or analogous to amino acid residue 385 or 470 of SEQ ID NO 2, g) a leucine residue at a position equivalent or analogous to amino acid residue 462 of SEQ ID NO: 2, h) an aspartic acid residue at a position equivalent or analogous to amino acid residue 472 of SEQ ID NO: 2, i) a glutamic acid at a position equivalent to or analogous to amino acid residue 473 of SEQ ID NO: 2, j) a leucine residue at a position equivalent or analogous to amino acid residue 321 of SEQ ID NO: 2, an arginine residue at a position equivalent or analogous to amino acid residue 322 of SEQ ID NO: 2, and a valine residue at a position equivalent or analogous to amino acid residue 323 of SEQ ID NO: 2, k) a glutamic acid residue at a position equivalent to or analogous to amino acid residue 450 of SEQ ID NO: 2, a valine residue at a position equivalent to or analogous to amino acid residue 451 of SEQ ID NO: 2, and an arginine residue at a position equivalent to or analogous to amino acid residue 452 of SEQ ID NO: 2, l) a lysine residue at a position equivalent to or analogous to amino acid residue 455 of SEQ ID NO: 2, a serine residue at a position equivalent to or analogous to amino acid residue 456 of SEQ ID NO: 2, an alanine residue at a position equivalent to or analogous to amino acid residue 457 of SEQ ID NO: 2, and a glutamine residue at a position equivalent to or analogous to amino acid residue 458 of SEQ ID NO: 2, m) an alanine residue at a position equivalent to or analogous to amino acid residue 470 of SEQ ID NO: 2, an aspartic acid residue at a position equivalent to or analogous to amino acid residue 472 of SEQ ID NO: 2, and a tyrosine residue at a position equivalent to or analogous to amino acid residue 473 of SEQ ID NO: 2, n) a threonine residue at a position equivalent to or analogous to amino acid residues 475, 477, and 478 of SEQ ID NO: 2, an arginine residue at a position equivalent to or analogous to amino acid residue 476 of SEQ ID NO: 2, and a histidine residue at a position equivalent to or analogous to amino acid residue 479 of SEQ ID NO: 2, or o) an aspartic acid residue at a position equivalent to or analogous to amino acid residue 481 of SEQ ID NO: 2, a glutamic acid residue at a position equivalent to or analogous to amino acid residue 482 of SEQ ID NO: 2, and a proline residue at a position equivalent to or analogous to amino acid residue 483 of SEQ ID NO: 2. Even more preferably, the isolated polypeptide comprises a substitution mutation selected from the group consisting of a) E401D or G429S of SEQ ID NO: 1, b) E401D and 04295 of SEQ ID NO: 1, c) T3378, K355R, S385A, V462L, 8470A, E471D, T473E, or E500S of SEQ ID NO: 2, d) G321L, P322R, and G323V of SEQ ID NO: 2, e) D450B, A451V, and K452R of SEQ ID NO: 2, f) S455K, N456S, P457A, and S458Q of SEQ ID NO: 2, g) S470A, E472D, and T473Y of SEQ ID NO: 2, h) C475T, K476R, Q477T, K478T, and Y479H of SEQ ID NO: 2, and i) B481D, Q482E, and Q483P of SEQ ID NO: 2.

In another specific embodiment, the present invention relates to an isolated polypeptide comprising a Group B nuclear receptor ligand binding domain comprising a substitution mutation, wherein the substitution mutation enhances both steroid binding activity or steroid sensitivity and non-steroid binding activity or non-steroid sensitivity of the Group B ligand binding domain.

In another specific embodiment, the present invention also relates to an isolated polypeptide comprising a Group B nuclear receptor ligand binding domain comprising a substitution mutation, wherein the substitution mutation increases ligand sensitivity of a heterodimer comprising the Group B nuclear receptor ligand binding domain comprising a substitution mutation and a dimerization partner. In a specific embodiment, the dimerization partner is an ecdysone receptor polypeptide. In another specific embodiment, the dimerization partner is a truncated EcR polypeptide.

The present invention also relates to compositions comprising an isolated polypeptide according to the invention.

Method of Modulating Gene Expression of the Invention

Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the ligand into the host cell, expression of the gene is modulated.

The invention also provides a method of modulating the expression of a gene in a host cell comprising the steps of a) introducing into the host cell a gone expression modulation system according to the invention; b) introducing into the host cell a gene expression cassette according to the invention, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a ligand; whereby upon introduction of the ligand into the host cell, expression of the gene is modulated.

Applicants' invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Genes of interest for expression in a host cell using Applicants' methods may be endogenous genes or heterologous genes. Nucleic acid or amino acid sequence information for a desired gone or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for expression in a host cell using Applicants' methods include, but are not limited to: antigens produced in plants as vaccines, enzymes like alpha-amylase, phytase, glucanes, xylase and xylanase, gum for resistance against insects, nematodes, fungi, bacteria, viruses, and abiotic stresses, nutraceuticals, antigens, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferon, insulin, erythropoietin, clotting factors, other blood factors or components, viral vectors for gene therapy, virus for vaccines, targets for drug discovery, functional genomics, and proteomics analyses and applications, and the like.

Acceptable ligands are any that modulate expression of the gene when binding of the DNA binding domain of the gene expression system according to the invention to the response element in the presence of the ligand results in activation or suppression of expression of the genes. Preferred ligands include an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726; dibenzoylalkyl cyanohydrazines such as those disclosed in European Application No. 461,809; N-alkyl-N,N'-diarylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U. U.S. Pat. No. 4,985,461; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T1901317, 5-alpha-6-alpha-epoxycholesterol-3-sulfate (ECHS), 7-ketocholesterol-3-sulfate, farnesol, bile acids, 1,1-biphosphonate esters, Juvenile hormone III, a 9-cis-retinoic acid, 4-(1-(3,5,5,8,8-pentamethyl-5,6,7,8-tetrahydro-2-napthyl)-ethenyl) benzoic acid (3-methyl-TTEB), ((E)-2)2-(5,6,7,8-tetrat-hydro-3,5,5,8,8-pentamethyl-2-napthyl)propen-1-yl)-4-thiophenecarboxylic acid), 2-(5,6,7,8-tetra-hydro-3,5,5,8,8-tetramethyl-2-naphthyl)-2-(carboxyphenyl)-1,3-dioxolane, 4-(5H-2,3-(2,5-dimethyl-2,5-hexano)-5-methyl-dibenzo (b,e) (1,4)diazepin-11-yl)-benzoic acid (HX600) or thiadiazepin analogs thereof, 3,7,11,15-tetramethyl hexadecanoic acid (phytanic acid), 6-(1-(3,5,5,8,8-pentamethyl-5,6,7,8-tetrahydronaphthalen-2-yl) cyclopropyl) nicotinic acid, 2-(4-carboxyphenyl)-2-(5,6,7,8-tetrahydro-5,5,8,8-tetramethyl-2-naphthalenyl)-1,3-dithiane, or 4-(2-methyl)-1,6,7,8-tetrahydro-5,5,8,8-tetramethyl-2-napthalenyl) propenyl)benzoic acid, and the like.

In a preferred embodiment, the ligand for use in Applicants' method of modulating expression of gene is a compound of the formula:

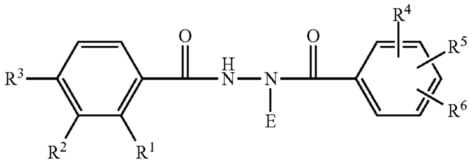

wherein:

E is a $(C_4-C_6)$alkyl containing a tertiary carbon or a cyano$(C_3-C_5)$alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH═CHCN, allyl, azido, SCN, or $SCHF_2$;

$R^2$ is H, Me, Et, n-Pt, i-Pr, formyl, $CF_3$, $CHF_2$, $CHCl_2$, $CH_2F$, $CH_2C1$, $CH_2OH$, $CH_2OMe$, $CH_2CN$, CN, C≡CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH═CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt;

In another preferred embodiment, the ligand for use in Applicants' method of modulating expression of gene is an ecdysone, 20-hydroxyecdysone, ponasterone A, or muristerone A.

In another preferred embodiment, the ligand for use in Applicants' method of modulating expression of gene is a 9-cis-retinoic acid, 4-(1-(3,5,5,8,8-pentamethyl-5,6,7,8-tetrahydro-2-napthyl)-ethenyl) benzoic acid (3-methyl-TTEB), ((E)-2)2-(5,6,7,8-tetrat-hydro-3,5,5,8,8-pentamethyl-naphtyl)propen-1-yl)-4-thiophenecarboxylic acid), 2-(5,6,7,8-tetra-hydro-3,5,5,8,8-tetramethyl-2-naphthyl)-2-(carboxyphenyl)-1,3-dioxolane, 4-(5H-2,3-(2,5-dimethyl-2,5-hexano)-5-methyl-dibenzo (b,e) (1,4)diazepin-11-yl)-benzoic acid (HX600) or thiadiazepin analogs thereof, 3,7,11,15-tetramethyl hexadecanoic acid (phytanic acid), 6-(1-(3,5,5,8,8-pentamethyl-5,6,7,8-tetrahydronaphthalen-2-yl) cyclopropyl) nicotinic acid, 2-(4-carboxyphenyl)-2-(5,6,7,8-tetrahydro-5,5,8,8-tetramethyl-2-naphthalenyl)-1,3-dithiane, or 4-(2-methy)-1-(5,6,7,8-tetrahydro-5,5,8,8-tetramethyl-2-napthalenyl) propenyl)benzoic acid.

In another preferred embodiment, a second ligand may be used in addition to the first ligand discussed above in Applicants' method of modulating expression of a gene. Preferably, this second ligand is 9-cis-retinoic acid or a synthetic analog of retinoic acid.

Host Cells and Non-Human Organisms of the Invention

As described above, the gene expression modulation system of the present invention may be used to modulate gene expression in a host cell. Expression in transgenic host cells may be useful for the expression of various genes of interest. Applicants' invention provides for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanes, xylase and xylanase, genes for resistance against insects, nematodes, fungi, bacteria, viruses, and abiotic stresses, nutraceuticals, antigens, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Thus, Applicants' invention provides an isolated host cell comprising a gene expression system according to the invention. The present invention also provides an isolated host cell comprising a gene expression cassette according to the invention. Applicants' invention also provides an isolated host cell comprising a polynucleotide or a polypeptide according to the invention. In another embodiment, the invention relates to a host cell transfected with an expression vector according to the invention. The host cell may be a bacterial cell, a fungal cell, a nematode cell, an insect cell, a fish cell, a plant cell, an avian cell, an animal cell, or a mammalian cell. In still another embodiment, the invention relates to a method for producing a nuclear receptor ligand binding domain comprising a substitution mutation, wherein the method comprises culturing the host cell as described above in culture medium under conditions permitting expression of a polynucleotide encoding the nuclear receptor ligand binding domain comprising a substitution mutation, and isolating the nuclear receptor ligand binding domain comprising a substitution mutation from the culture.

In a specific embodiment, the isolated host cell is a prokaryotic host cell or a eukaryotic host cell. In another specific embodiment, the isolated boat cell is an invertebrate host cell or a vertebrate host cell. Preferably, the host cell is selected from the group consisting of a bacterial cell, a fungal cell, a yeast cell, a nematode cell, an insect cell, a fish cell, a plant cell, an avian cell, an animal cell, and a mammalian cell. More preferably, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell.

Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*, plant species selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, *sorghum*, soybean, squash, sugarcane, sugarbeet, sunflower, sweet potato, tea, tomato, tobacco, watermelon, and wheat, animal, and mammalian host cells.

In a specific embodiment, the host cell is a yeast cell selected from the group consisting of a *Saccharomyces*, a *Pichia*, and a *Candida* host cell.

In another specific embodiment, the host cell is a *Caenorhabdus elegans* nematode coll.

In another specific embodiment, the host cell is an insect cell.

In another specific embodiment, the host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum, papaya*, peanut, pea, pepper, pigeonpea, pineapple, *Phaseolus*, potato, pumpkin, rice, *sorghum*, soybean, squash, sugarcane, sugarbeet, sunflower, sweet potato, tea, tomato, tobacco, watermelon, and wheat cell.

In another specific embodiment, the host cell is a zebrafish cell.

In another specific embodiment, the host cell is a chicken cell.

In another specific embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell and a human cell.

Host cell transformation is well known in the art and may be achieved by a variety of methods including but not limited to electroporation, viral infection, plasmid/vector transfection, no-viral vector mediated transfection, *Agrobacterium*-mediated transformation particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanism for the translational and post-translational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of *Saccharomyces*, *Pichia*, and *Candida*.

In another specific embodiment, the non-human organism is a *Caenorhabdus elegans* nematode.

In another specific embodiment, the non-human organism is a plant selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum, papaya*, peanut, pea, pepper, pigeonpea, pineapple, *Phaseolus*, potato, pumpkin, rice, *sorghum*, soybean, squash, sugarcane, sugarbeet, sunflower, sweet potato, tea, tomato, tobacco, watermelon, and wheat.

In another specific embodiment, the non-human organism is a *Mus musculus* mouse.

Measuring Gene Expression/Transcription

One useful measurement of Applicants' methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonuclotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonuclotides which allow fractionation of short DNA molecules whereas the larger DNA targets of microarrays, approximately 1000 base pairs, may provide more sensitivity in fractionating complex DNA mixtures.

Another useful measurement of Applicants' methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, a senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using Applicants' invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybridizes.

In same cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like.

PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are preset.

Ligand Screening Assays

The present invention also relates to methods of screening for a compound that induces or represses transactivation of a nuclear receptor ligand binding domain comprising a substitution mutation in a cell by contacting a nuclear receptor ligand binding domain with a candidate molecule and detecting reporter gene activity in the presence of the ligand. Candidate compounds may be either agonists or antagonists of the nuclear receptor ligand binding domain. In a preferred embodiment, the nuclear receptor ligand binding domain is expressed from a polynucleotide in the cell and the transactivation activity (i.e., expression or repression of a reporter gene) or compound binding activity is measured.

Accordingly, in addition to rational design of agonists and antagonists based on the structure of a nuclear receptor ligand binding domain, the present invention contemplates an alternative method for identifying specific ligands of a nuclear receptor ligand binding domain using various screening assays known in the art.

Any screening technique known in the art can be used to screen for Group B nuclear receptor ligand binding domain agonists or antagonists. For example, a suitable cell line comprising a nuclear receptor-based gene expression system according to the invention can be transfected with a gene expression cassette encoding a marker gene operatively linked to an inducible or repressible promoter. The transfected cells are then exposed to a test solution comprising a candidate agonist or antagonist compound, and then assayed for marker gene expression or repression. The presence of more marker gene expression relative to control cells not exposed to the test solution is an indication of the presence of an agonist compound in the test solution. Conversely, the presence of less marker gene expression relative to control cells not exposed to the test solution is an indication of the presence of an antagonist compound in the test solution.

The present invention contemplates screens for small molecule ligands or ligand analogs and mimics, as well as screens for natural ligands that bind to and agonize or antagonize a Group B nuclear receptor ligand binding domain according to the invention in vivo. For example, natural products libraries can be screened using assays of the invention for molecules that agonize or antagonize nuclear receptor-based gene expression system activity.

Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386-390 (1990); Cwirla, et al., *Proc. Natl. Acad. Sci.,* 87:6378-6382 (1990); Devlin et al., *Science,* 249:404-406 (1990)], very large libraries can be constructed ($10^6$-$10^8$ chemical entities). A second approach uses primarily chemical methods, of which the Geysen method [Geysen et al., *Molecular Immunology* 23:709-715 (1986); Geysen et al. *J. Immunologic Method* 102:259-274 (1987)] and the method of Fodor et al. [*Science* 251:767-773 (1991)] are examples. Furka et al. [*14th International Congress of Biochemistry, Volume* 5, Abstract FR:013 (1988); Furka, *Int. J. Peptide Protein Res.* 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. USA* 90:10700-4 (1993); Ohlmeyer et al., *Proc. Natl. Acad. Sci. USA* 90:10922-10926 (1993); Lam et al., International Patent Publication No. WO 92/00252; Kocis et al., International Patent Publication No. WO 9428028, each of which is incorporated herein by reference in its entirety], and the like can be used to screen for candidate ligands according to the present invention.

The screening can be performed with recombinant cells that express a nuclear receptor ligand binding domain according to the invention, or alternatively, using purified protein, e.g., produced recombinantly, as described above. For example, labeled, soluble nuclear receptor ligand binding domains can be used to screen libraries, as described in the foregoing references.

In one embodiment, a Group B nuclear receptor ligand binding domain according to the invention may be directly labeled. In another embodiment, a labeled secondary reagent may be used to detect binding of a nuclear receptor ligand binding domain of the invention to a molecule of interest, e.g., a molecule attached to a solid phase support. Binding may be detected by in situ formation of a chromophore by an enzyme label. Suitable enzymes include, but are not limited to, alkaline phosphatase and horseradish peroxidase. In a further embodiment, a two-color assay, using two chromogenic substrates with two enzyme labels on different acceptor molecules of interest, may be used. Cross-reactive and singly-reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Two color assays may be performed with two or more colored latex beads, or fluorophores that emit at different wavelengths. Labeled molecules or cells may be detected visually or by mechanical/optical means. Mechanical/optical means include fluorescence activated sorting, i.e., analogous to FACS, and micromanipulator removal means.

The present invention may be better understood by reference to the following non-limiting Examples, which are provided as exemplary of the invention.

EXAMPLES

Applicants have developed a novel nuclear receptor-based inducible gene expression system comprising a Group B nuclear receptor ligand binding domain comprising a substitution mutation. Applicants have shown that the effect of such a substitution mutation may increase ligand binding activity or ligand sensitivity and may be steroid or non-steroid specific. Thus, Applicants' invention provides a Group B nuclear receptor-based inducible gene expression system useful for modulating expression of a gene of interest in a host cell. Applicants' novel inducible gene expression system and its use in methods of modulating gene expression in a host cell overcome the limitations of currently available inducible expression systems and provide the skilled artisan with an effective means to control gene expression.

Applicants' novel substitution mutated nuclear receptor polynucleotides and polypeptides are useful in a nuclear receptor-based inducible gene modulation system for various applications including but not limited to gene therapy, expression of proteins of interest in host cells, production of transgenic organisms, and cell-based assays.

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the GCG "Gap" or "Bestfit" program is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s) "sec" means second(s), "d" means day(s), "μl" means microliter(s), "ml" means milliliter(s), "L" means liter(s), "μM" means micromolar, "mM" means millimolar, "μg" means microgram(s), "mg" means milligram(s), "A" means adenine or adenosine, "T" means thymine or thymidine, "G" means guanine or guanosine, "C" means cytidine or cytosine, "xg" means times gravity, "nt" means nucleotide(s), "aa" means amino acid(s), "bp" means base pair(s), "kb" means kilobase(s), "k" means kilo, "μ" means micro, and "° C." means degrees Celsius.

Example 1

This Example describes the construction of several gene expression cassettes comprising novel substitution mutated Group B nuclear receptor polynucleotides and polypeptides of the invention for use in a nuclear receptor-based inducible gene expression system. Applicants constructed several gene expression cassettes based on the spruce budworm *Choristoneura fumiferana* EcR ("CfEcR"), mouse *Mus musculus* retinoid X receptor α ("MmRXRα"), human *Homo sapiens* retinoid X receptor A ("HsRXR"), locust *Locusta migratoria* ultraspiracle protein (referred to herein interchangeably as "LmUSP" or "LmRXR"), which is an invertebrate RXR homolog of vertebrate RXR, and *C. fumiferana* USP ("CfUSP"). The prepared receptor constructs comprise a ligand binding domain of either an EcR, an invertebrate USP, a vertebrate RXR, or an invertebrate RXR; and a GAL4 DNA binding domain (DBD) or a VP16 transactivation domain (AD). The reporter constructs include a reporter gene, luciferase or LacZ (β-galactosidase), operably linked to a synthetic promoter construct that comprises a GALA response element to which the Gal4 DBD binds. Various combinations of these receptor and reporter constructs were cotransfected into mammalian cells as described in Examples 2-4 infra.

Gene Expression Cassettes:

The gene expression cassettes (switches) were constructed as followed, using standard cloning methods available in the art. The following is a brief description of preparation and composition of each switch used in the Examples described herein.

1.1—GAL4CfEcR-DEF/VP16LmUSP-EF:

The wild-type D, E, and F domains from spruce budworm *Choristoneura fumiferana* EcR ("CfEcR-DEF"; SEQ ID NO: 20) were fused to a GAL4 DNA binding domain ("Gal4DNABD" or "Gal4DBD"; SEQ ID NO: 5) and placed under the control of an SV40e promoter (SEQ ID) NO: 21). The E and F domains from locust *Locusta migratoria* ultraspiracle protein ("LmUSP-EP"; SEQ ID NO: 22) were fused to the transactivation domain from VP16 ("VP16AD"; SEQ ID NO: 11) and placed under the control of an SV40e promoter (SEQ ID NO: 21). Five consensus GAL4 response element binding sites ("5XGAL4E"; comprising 5 copies of a GAL4RE comprising SEQ ID NO: 18) were fused to a synthetic E1b minimal promoter (SEQ ID NO: 23) and placed upstream of the luciferase gene (SEQ ID NO: 24).

1.2—GAL4CfEcR-DEF/VP16MmRXRα-EF:

This construct was prepared in the same way as in switch 1.1 above except LmUSP-EF was replaced with the E and P domains of MmRXRα ("MmRXRα-EF"; SEQ ID NO: 25).

1.3—GAL4CfEcR-DEF/VP16mutantMmRXRα-EF:

This construct was prepared in the same way as in switch 1.2 above except wild-type MmRXRα-EF was replaced with mutant MmRXRα-EF comprising a ligand binding domain comprising a substitution mutation selected from Table 1 below.

TABLE 1

Substitution Mutants of *Mus musculus* Retinoid X Receptor α ("MmRXRα") Ligand Binding Domain (LBD).

| MmRXRα LBD Mutation | Resulting "WT to Mutant" Amino Acid Substitution | Corresponding amino acid in full length MmRXRα (SEQ ID NO: 1) |
|---|---|---|
| E401D | Glutamic Acid (E) to Aspartic Acid (D) | 401 |
| G429S | Glycine (G) to Serine (S) | 429 |
| E401D/G429S | Glutamic Acid (E) to Aspartic Acid (D) and Glycine (G) to Serine (S) | 401 and 429 respectively |

1.4—GAL4CfEcR-DEF/VP16MmRXRαH1-7LmUSP-H8-12chimera:

This construct was prepared in the same way as in switch 1.1 above except LmUSP-EF was replaced with a chimeric ligand binding domain comprising helices (H) 1-7 of MmRXRα-EF and helices 8-12 of LmUSP-EF (SEQ ID NO: 26).

1.5—GALCfEcR-DEF/VP16HsRXRβ-EF:

This construct was prepared in the same way as in switch 1.1 above except LmUSP-EF was replaced with the E and F domains of HsRXRβ ("HsRXRβ-EF"; SEQ ID NO: 27).

1.6—GAL4CfEcR-DEF/VP16mutantHsRXRβ-EF:

This construct was prepared in the some way as in switch 1.5 above except wild-type HsRXRβ-EF was replaced with mutant HsRXRβ-EF comprising a ligand binding domain comprising a substitution mutation selected from Table 2 below.

TABLE 2

Substitution Mutants of *Homo sapiens* Retinoid X Receptor β ("HsRXRβ") Ligand Binding Domain (LBD).

| HsRXRβ LBD Mutation | Resulting "WT to Mutant" Amino Acid Substitution | Corresponding amino acid in full length HsRXRβ (SEQ ID NO: 2) |
|---|---|---|
| G321L/P322R/G323V | Glycine (G) to Leucine (L), Proline (P) to Arginine (R), and Glycine (G) to Valine (V) | 321, 322, and 323 respectively |
| T337S | Threonine (T) to Serine (S) | 337 |
| D344N | Aspartic Acid (D) to Asparagine (N) | 344 |
| K355R | Lysine (K) to Arginine (R) | 355 |
| S385A | Serine (S) to Alanine (A) | 385 |
| M431L | Methionine (M) to Leucine (L) | 431 |
| R442K | Arginine (R) to Lysine (K) | 442 |
| D450E/A451V/K452R | Aspartic Acid (D) to Glutamic Acid (E), Alanine (A) to Valine (V), and Lysine (K) to Arginine (R) | 450, 451, and 452 respectively |
| S455K/N456S/P457A/S458Q | Serine (S) to Lysine (K), Asparagine (N) to Serine (S), Proline (P) to Alanine (A), and Serine (S) to Glutamine (Q) | 455, 456, 457, and 458 respectively |
| V462L | Valine (V) to Leucine (L) | 462 |
| S470A | Serine (S) to Alanine (A) | 470 |
| E472D | Glutamic Acid (E) to Aspartic Acid (D) | 472 |
| T473E | Threonine (T) to Glutamic Acid (E) | 473 |
| S470A/E472D/T473Y | Serine (S) to Alanine (A), Glutamic Acid (E) to Aspartic Acid (D), and Threonine (T) to Tyrosine (Y) | 470, 472, and 473 respectively |

TABLE 2-continued

Substitution Mutants of *Homo sapiens* Retinoid X Receptor β ("HsRXRβ") Ligand Binding Domain (LBD).

| HsRXRβ LBD Mutation | Resulting "WT to Mutant" Amino Acid Substitution | Corresponding amino acid in full length HsRXRβ (SEQ ID NO: 2) |
|---|---|---|
| C475T/K476R/Q477T/K478T/Y479H | Cysteine (C) to Threonine (T), Lysine (K) to Arginine (R), Glutamine (Q) to Threonine (T), Lysine (K) to Threonine (T), and Tyrosine (Y) to Histidine (H) | 475, 476, 477, 478, and 479 respectively |
| E481D/Q482E/Q483P | Glutamic Acid (E) to Aspartic Acid (D), Glutamine (Q) to Glutamic Acid (E), and Glutamine (Q) to Proline (P) | 481, 482, and 483 respectively |
| A495S | Alanine (A) to Serine (S) | 495 |
| G500S | Glycine (G) to Serine (S) | 500 |
| K511R | Lysine (K) to Arginine (R) | 511 |
| T516V | Threonine (T) to Valine (V) | 516 |
| A528S | Alanine (A) to Serine (S) | 528 |

Construction of Retinoid X Receptor Ligand Binding Domains Comprising a Substitution Mutation:

In an effort to modify RXR transactivation activity, residues within the RXR ligand binding domains that were predicted to be important based upon sequence comparisons were mutated in RXRs from two different organisms. Tables 1 and 2 indicate the amino acid residues within the ligand binding domain of MmRxRα and HsRXRβ, respectively that were mutated and examined for modification of transactivation ability.

Each one of the amino acid substitution mutations listed in Tables 1 and 2 was constructed in an RXR cDNA by PCR mediated site-directed mutagenesis. One double point mutant RXR LBD (see Table 1), four different triple point mutant RXR LBDs (see Table 2), one quadruple point mutant RXR LBD (see Table 2), and one quintuple point mutant RXR LBD (see Table 2) were also constructed.

PCR site-directed mutagenesis was performed using the Quikchange site-directed mutagenesis kit (Stratagene, La Jolla, Calif.) using the reaction conditions and cycling parameters as follows. PCR site-directed mutagenesis was performed using 1× reaction buffer (supplied by manufacturer), 50 ng of dsDNA template, 125 ng of forward primer (FP), 125 ng of reverse complementary primer (RCP), and 1 μl of dNTP mix (supplied by manufacturer) in a final reaction volume of 50 μL. The forward primer and reverse complementary primer pairs used to produce each RXR substitution mutation are presented in Tables 3 and 4. The cycling parameters used consisted of one cycle of denaturing at 95° C. for 30 seconds, followed by 16 cycles of denaturing at 95° C. for 30 seconds, annealing at 55° C. for 1 minute, and extending at 68° C. for 22 minute.

TABLE 3

PCR Primers for Substitution Mutant MmRXRα Ligand Binding Domain Construction

| MUTANT | PRIMER (SEQ ID NO:) | PRIMER NUCLEOTIDE SEQUENCE (5' TO 3') |
|---|---|---|
| E401D | FP (SEQ ID NO: 28) | GTGTATGCGTCACTAGATG CGTACTGCAAACAC |
| E401D | RCP (SEQ ID NO: 29) | GTGTTTGCAGTACGCATCT AGTGACGCATACAC |

TABLE 3-continued

PCR Primers for Substitution Mutant MmRXRα Ligand Binding Domain Construction

| MUTANT | PRIMER (SEQ ID NO:) | PRIMER NUCLEOTIDE SEQUENCE (5' TO 3') |
|---|---|---|
| G429S | FP (SEQ ID NO: 30) | GCACTGCGTTCCATCAGCCTCAAGTGCCTGGAG |
| G429S | RCP (SEQ ID NO: 31) | CTCCAGGCACTTGAGGCTGATGGAACGCAGTGC |

TABLE 4

PCR Primers for Substitution Mutant HsRXRβ Ligand Binding Domain Construction

| MUTANT | PRIMER (SEQ ID NO:) | PRIMER NUCLEOTIDE SEQUENCE (5' TO 3') |
|---|---|---|
| G321L/P322R/G323V | FP (SEQ ID NO: 32) | GACCAGGGCGTTGAGCGTCGTGTGGGAACCGGGGGTAGC |
| G321L/P322R/G323V | RCP (SEQ ID NO: 33) | GCTACCCCCGGTTCCCACACGACGCTCAACGCCCTGGTC |
| T337S | FP (SEQ ID NO: 34) | CCAAATGACCCTGTGTCTAACATCTGTCAGGC |
| T337S | RCP (SEQ ID NO: 35) | GCCTGACAGATGTTAGACACAGGGTCATTTGG |
| D344N | FP (SEQ ID NO: 36) | ATCTGTCAGGCAGCTAACAAACAGCTATTCACG |
| D344N | RCP (SEQ ID NO: 37) | CGTGAATAGCTGTTTGTTAGCTGCCTGACAGAT |
| K355R | FP (SEQ ID NO: 38) | CTTGTTGAGTGGGCGAGGAGGATCCCACACTTTTC |
| K355R | RCP (SEQ ID NO: 39) | GAAAAGTGTGGGATCCTCCTCGCCCACTCAACAAG |
| S385A | FP (SEQ ID NO: 40) | CTCATTGCCTCCTTTGCACACCGATCCATTGATG |
| S385A | RCP (SEQ ID NO: 41) | CATCAATGGATCGGTGTGCAAAGGAGGCAATGAG |
| M431L | FP (SEQ ID NO: 42) | TCCAAAATGCGTGACCTGAGGATGGACAAGAC |
| M431L | RCP (SEQ ID NO: 43) | GTCTTGTCCATCCTCAGGTCACGCATTTTGGA |
| R442K | FP (SEQ ID NO: 44) | GAGCTTGGCTGCCTGAAGGCAATCATTCTGTTTAATC |
| R442K | RCP (SEQ ID NO: 45) | GATTAAACAGAATGATTGCCTTCAGGCAGCCAAGCTC |
| D450E/A451V/K452R | FP (SEQ ID NO: 46) | CATTCTGTTTAATCCAGAGGTCAGGGGCCTCTCCAACCC |
| D450E/A451V/K452R | RCP (SEQ ID NO: 47) | GGGTTGGAGAGGCCCCTGACCTCTGGATTAAACAGAATC |
| S455K/N456S/P457A/S458Q | FP (SEQ ID NO: 48) | GATGCCAAGGGCCTCAAGTCCGCGCAGGAGGTGGAGGTCCTG |

TABLE 4-continued

PCR Primers for Substitution Mutant HsRXRβ Ligand Binding Domain Construction

| MUTANT | PRIMER (SEQ ID NO:) | PRIMER NUCLEOTIDE SEQUENCE (5' TO 3') |
|---|---|---|
| S455K/N456S/P457A/S458Q | RCP (SEQ ID NO: 49) | CAGGACCTCCACCTCCTGCGCGGACTTGAGGCCCTTGGCATC |
| V462L | FP (SEQ ID NO: 50) | CCTAGTGAGGTGGAGCTCCTGCGGGAGAAAGTGTATG |
| V462L | RCP (SEQ ID NO: 51) | CATACACTTTCTCCCGCAGGAGCTCCACCTCACTAGG |
| S470A | FP (SEQ ID NO: 52) | GAGAAAGTGTATGCAGCACTGGAGACCTACTGC |
| S470A | RCP (SEQ ID NO: 53) | GCAGTAGGTCTCCAGTGCTGCATACACTTTCTC |
| E472D | FP (SEQ ID NO: 54) | GTGTATGCATCACTGGATACCTACTGCAAACAG |
| E472D | RCP (SEQ ID NO: 55) | CTGTTTGCAGTAGGTATCCAGTGATGCATACAC |
| T473E | FP (SEQ ID NO: 56) | GTATGCATCACTGGAGGAGTACTGCAAACAGAAG |
| T473E | RCP (SEQ ID NO: 57) | CTTCTGTTTGCAGTACTCCTCCAGTGATGCATAC |
| S470A/E472D/T473Y | FP (SEQ ID NO: 58) | GAGAAAGTGTATGCAGCACTGGATGAGTACTGCAAACAGAAG |
| S470A/E472D/T473Y | RCP (SEQ ID NO: 59) | CTTCTGTTTGCAGTACTCATCCAGTGCTGCATACACTTTCTC |
| C475T/K476R/Q477T/K478T/Y479H | FP (SEQ ID NO: 60) | CATCACTGGAGACCTACACCAGAACGACGCACCCTGAGCAGCAGGGAC |
| C475T/K476R/Q477T/K478T/Y479H | RCP (SEQ ID NO: 61) | GTCCCTGCTGCTCAGGGTGCGTCGTTCTGGTGTAGGTCTCCAGTGATG |
| E481D/Q482E/Q483P | FP (SEQ ID NO: 62) | CAAACAGAAGTACCCTGACGAGCCGGGACGGTTTGCCAAG |
| E481D/Q482E/Q483P | RCP (SEQ ID NO: 63) | CTTGGCAAACCGTCCCGGCTCGTCAGGGTACTTCTGTTTG |
| A495S | FP (SEQ ID NO: 64) | CTGCTACGTCTTCCTTCCCTCCGGTCCATTGGC |
| A495S | RCP (SEQ ID NO: 65) | GCCAATGGACCGGAGGGAAGGAAGACGTAGCAG |
| G500S | FP (SEQ ID NO: 66) | GCCCTCCGGTCCATTAGCCTTAAGTGTCTAGAG |
| G500S | RCP (SEQ ID NO: 67) | CTCTAGACACTTAAGGCTAATGGACCGGAGGGC |
| K511R | FP (SEQ ID NO: 68) | CATCTGTTTTTCTTCAGGCTCATTGGTGACACC |
| K511R | RCP (SEQ ID NO: 69) | GGTGTCACCAATGAGCCTGAAGAAAAACAGATG |

TABLE 4-continued

PCR Primers for Substitution Mutant HsRXRβ Ligand Binding Domain Construction

| MUTANT | PRIMER (SEQ ID NO:) | PRIMER NUCLEOTIDE SEQUENCE (5' TO 3') |
|---|---|---|
| T516V | FP (SEQ ID NO: 70) | AGCTCATTGGTGACGTCCC CATCGACACCTTCC |
| T516V | RCP (SEQ ID NO: 71) | GGAAGGTGTCGATGGGGAC GTCACCAATGAGCT |
| A528S | FP (SEQ ID NO: 72) | ATGGAGATGCTTGAGTCTC CCCATCAACTGGCC |
| A528S | RCP (SEQ ID NO: 73) | GGCCAGTTGATGGGGAGAC TCAAGCATCTCCAT |

The resulting PCR nucleic acid products encoding the mutant RXR ligand binding domains were then each fused to a VP16 transactivation domain as described in Examples 1.3 and 1.6 above. The VP16/mutant RXR receptor constructs were tested for activity by transfecting them into NIH3T3 cells along with GAL4/CfEcR-DEF and pFRLuc in the presence of non-steroid ligand.

Ligand:

The non-steroidal ligand N-(2-ethyl-3-methoxybenzoyl)-N'-(3,5-dimethylbenzoyl)-N'-tert-butylhydrazine (GS™-E) is a synthetic stable ecdysteroid ligand synthesized at Rohm and Hams Company. The ligand was dissolved in DMSO and the final concentration of DMSO was maintained at 0.1% in both controls and treatments.

Transfections:

DNAs corresponding to the various switch constructs outlined in Example 1.1-1.6 were transfected into mouse NIH3T3 cells (ATCC) as follows. Standard methods for culture and maintenance of the cells were followed. Cells were harvested when they reached 50% confluency and plated in 6-, 12- or 24-well plates at 125,000, 50,000, or 25,000 cells, respectively, in 2.5, 1.0, or 0.5 ml of growth medium containing 10% fetal bovine serum (FBS), respectively. The next day, the cells were rinsed with growth medium and transfected for four hours. Superfect™ (Qiagen Inc.) was used as the transfection reagent. For 12-well plates, 4 μl of Superfect™ was mixed with 100 μl of growth medium. One μg of reporter construct and 0.25 μg of each receptor construct of the receptor pair to be analyzed were added to the transfection mix. A second reporter construct was added [pTKRL (Promega), 0.1 μg/transfection mix] that comprises a *Renilla* luciferase gene operably linked and placed under the control of a thymidine kinase (IX) constitutive promoter and was used for normalization. The contents of the transfection mix were mixed in a vortex mixer and let stand at room temperature for 30 minutes. At the end of incubation, the transfection mix was added to the cells maintained in 400 μl growth medium. The cells were maintained at 37° C. and 5% $CO_2$ for four hours. At the end of incubation, 500 μl of growth medium containing 20% PBS and either dimethylsulfoxide (DMSO; control) or a DMSO solution of non-steroidal ligand was added and the cells were maintained at 37° C. and 5% $CO_2$ for 48 hours. The cells were harvested and reporter activity was assayed. The same procedure was followed for 6 and 24 well plates as well except all the reagents were doubled for 6 well plates and educed to half for 24-well plates.

Reporter Assays:

Cells were harvested 40 hours after adding ligand. 125 μl of passive lysis buffer (part of Dual-Luciferase™ reporter assay system from Promega Corporation) were added to each well of the 24-well plate. The plates were placed on a rotary shaker for 15 minutes. Twenty μl of lysate were assayed. Luciferase activity was measured using Dual-luciferase reporter assay system from Promega Corporation following the manufacturer's instructions. β-Galactosidase was measured using Galacto-Star™ assay kit from TROPIX following the manufacturer's instructions. All luciferase and β-galactosidase activities were normalized using *Renilla* luciferase as a standard. Fold activities were calculated by dividing normalized relative light units ("RLU") in ligand treated cells with normalized RLU in DMSO treated cells (untreated control).

Example 2

In mammalian cells, the insect (*Choristoneura fumiferana*) Ecdysone Receptor (CfEcR) heterodimerizes with ultraspiracle (USP) or its homolog retinoid X receptor (RXR) and transactivates genes that are placed under the control of cognate response elements. Ligand inducibility of this EcR-based transactivation depends on its heterodimerizing partner. As previously shown by Applicants, transactivation through CfEcR in partnership with insect USPs is ligand independent, whereas transactivation through CfEcR in partnership with invertebrate or vertebrate RXRs is ligand dependent (see U.S. patent application 60/294,814, incorporated herein by reference in its entirety). Applicants have now discovered that the sequence of RXR can be modified by substitution mutation of the ligand binding domain to influence the magnitude of transactivation as well as ligand sensitivity of an EcR-based inducible gene expression system.

This Example describes the identification of three MmRXRα ligand binding domain substitution mutants that exhibit improved ligand sensitivity in response to non-steroidal ligand. Briefly, Applicants constructed three mouse RXR isoform α ligand binding domain substitution mutants and created VP16/mutantMmRXRAα-EF cDNA gene expression cassettes as described in Example 1 above using the Quikchange PCR-mediated site-directed mutagenesis kit (Stratagene, La Jolla, Calif.). The mutated cDNAs were tested along with GAL4/CfEcR-DEP in GAL4-driven luciferase reporter assays and the results were compared to wild type VP16/MmRXRα-EF and VP16/MmRXRα-LmUSPchimera-EF switches in mouse NIH3T3 cells.

Transfections:

DNAs corresponding to the various switch constructs outlined in Example 1, specifically switches 1.1-1.4, were transfected into mouse NIH3T3 cells (ATCC) as follows. Cells were harvested when they reached 50% confluency and plated in 24 well plates at 12,500 cells/well in 0.5 ml of growth medium containing 10% fetal bovine serum (FBS). The next day, the cells were rinsed with growth medium and transfected for four hours. Superfect™ (Qiagen Inc.) was found to be the best transfection reagent for 3T3 cells. Two μl of Superfect™ was mixed with 100 μl of growth medium and 50 ng of GAL4/CfEcR-DEF cassette, 50 ng of: VP16/LmUSP-EF, VP16/wild-typeMmRXRα-EF, VP16/MmRXRα-LmUSPchimera-EF, or VP16/mutantMmRXRα-EF, and 200 ng of pFRLuc were added to the transfection mix. A second reporter construct was added [pTKRL (Promega), 0.05 μg/transfection mix] that comprises a *Renilla* luciferase gene operably linked and placed under the control of a thymidine kinase (TK) constitutive promoter and was used for normalization. The contents of the transfection mix were mixed in a vortex mixer and let stand at room temperature for 30 min. At the end of incubation, the transfection mix was added to the cells maintained in 200 µl growth medium. The cells were maintained at 37° C. and 5% $CO_2$ for four hours. At the end of incubation, 250 µl of growth medium containing 20% PBS and either dimethylsulfoxide (DMSO; control) or a DMSO solution of 0.2, 1, or 10 µM GS™-E [N-(2-ethyl-3-methoxybenzoyl)N'-(3,5-dimethylbenzoyl)-N'-tert-butylhydrazine] non-steroidal ligand was added and the cells were maintained at 37° C. and 5% $CO_2$ for 40 hours. The cells were harvested and reporter activity was assayed as described above. Fold activities were calculated by dividing normalized relative light units ("RLU") in ligand treated cells with normalized RLU in DMSO treated cells (untreated control).

As discussed above, Applicants have previously shown that non-lepidopteran/non-dipteran invertebrate RXRs and RX homologs (USPs), referred to herein collectively as invertebrate RXRs, bind EcR and transactivate reporters at higher levels than those achieved by vertebrate RXRs in mammalian cells. However, vertebrate RXRα provide lower background levels in the absence of ligand. Applicants compared the amino acid sequences from ligand binding domain of vertebrate RXRs and invertebrate RXRs and have identified two particular amino acids that are conserved in all vertebrate RXRs but are different in invertebrate RXRs. Applicants determined whether replacing a vertebrate RXR amino acid with an invertebrate RXR amino acid would result in higher activity upon induction, but still provide low background in the absence of ligand.

Applicants have now identified two amino acid residues within the EF domains of a vertebrate mouse RXR, isoform α ("MmRXRα-EF") that, when substituted, yield a mutant RXR that exhibits increased sensitivity to a non-steroid ligand. The effect of these two substitution mutations: an aspartic acid substitution at amino acid residue 401 (E401D mutant), and a serine substitution at amino acid residue 429 (G429S mutant) of SEQ ID NO: 1, on the activity of the mutated MmRXRα-EP receptor is presented in FIG. 1.

In transactivation assays in NIH3T3 cells, the B401D mutant behaved more like an invertebrate RXR than a vertebrate RXR by demonstrating both higher background and higher induction levels (see FIG. 1). The G429S mutant behaved more like an invertebrate RXR, demonstrating increased sensitivity to ligand but less background (see FIG. 1). Thus, Applicants have demonstrated a surprising and unexpected result that a single amino acid change can drastically alter the behavior of the MmRXRα-EF in the presence and absence of ligand.

To determine if the combination of these two mutations would provide a further improved RXR than either single point mutation alone, Applicants made a double substitution mutant MmRXR-EF comprising a point mutation at both positions E401D and G429S. Three independent clones of these double mutants (DM) were analyzed in NIH3T3 cells and compared with each single point mutant alone, MmRXRα-EF, and a chimeric vertebrate RXR/invertebrate RXR (see FIG. 2). Applicants' results show that these double mutants work as well as the chimeric RXR, demonstrating low background levels in the absence of ligand and increased induction levels and ligand sensitivity. These novel double substitution mutants provide an advantageous RXR for use in in vivo applications.

Figure 2:
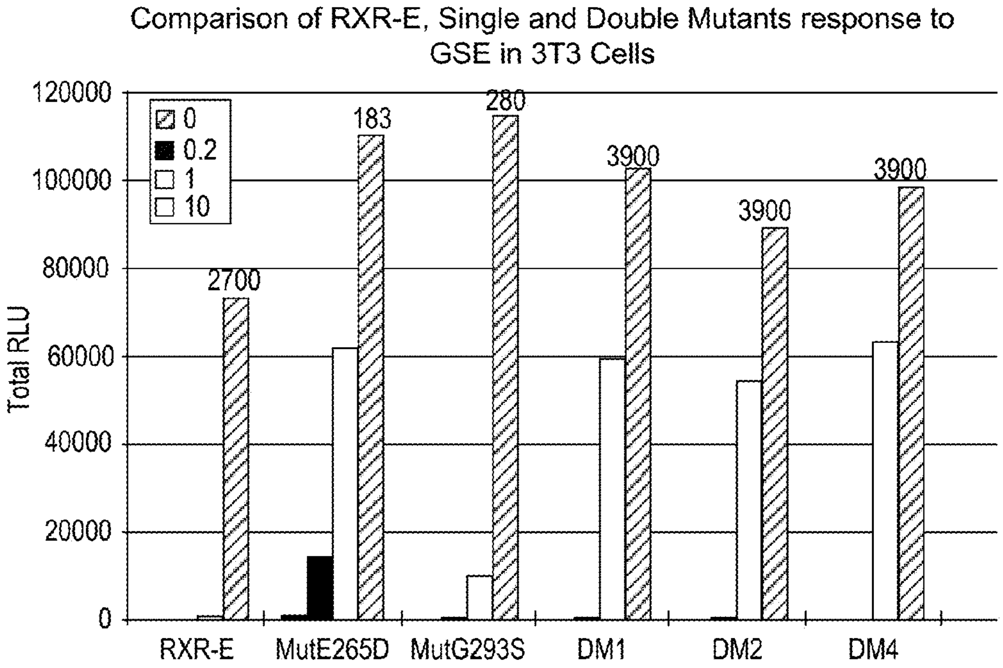
FIG. 2: Reporter gene transactivation of VP16/MmRXRα-EF (RXR-E) VP16/LmUSP-EF (LmUSP-E), VP16/chimeric vertebrate RXR/invertebrate RXR (Chimera), or VP16/RXRα-BF mutants E401D (MutE265D), G429S (MutG293S) or three independent clones of double mutant E401D+G429S (DM1, DM2, and DM4) transfected into NIH3T3 cells along with GAL4/CfEcR-DEF and pFRLuc. The cells were grown in the presence of 0, 0.2, 1 and 10 μM GS™-E for 48 hours and the reporter activity was assayed. The numbers on the top of the bars show the maximum fold induction.

Applicants have also determined that these MmRXRα-EF substitution mutants respond better than wild-type HsRXRβ-EF in the presence of a steroid ligand, ponasterone A (Invitrogen), similar to their response to GS™-E presented in FIGS. 1 and 2 (data not shown).

Example 3

As discussed above, use of an invertebrate RXR, LmUSP (also referred to herein as LmRXR) as a heterodimeric partner for CfEcR improved both the sensitivity and magnitude of induction of a CfEcR-based inducible gene expression system. Applicants have aligned the polypeptide sequences of the LmRXR and HsRXRβ ligand binding domains (domains EF) and identified amino acid residues that are different between these two proteins. This Example describes Applicants' analysis of HsRXRβ substitution mutants in which LmRXR amino acids were substituted in place of the wild-type residues in HsRXRβ. Applicants have now identified several substitution mutants that modify both the sensitivity and magnitude of induction of a CfEcR-based inducible gone expression system in mammalian cells.

Briefly, Applicants constructed and analyzed substitution mutants in human RXR isoform β-EF (HsRXRβ-EF), wherein amino acids that are different in HsRXRβ-EF compared to the invertebrate RXR homolog LmUSP-EF were mutated to the LmUSP-EF amino acid residue and assayed for their effect on transactivation activity in NIH3T3 cells as described in Example 2 above in the presence of 0, 0.04, 0.2, 1, 5, or 25 µM GS™-E [N-(2-ethyl-3-methoxybenzoyl)N'-(3,5-dimethylbenzoyl)-N'-tert-butylhydrazine] non-steroidal ligand. The cells were harvested and reporter activity was assayed as described above. Fold activities were calculated by dividing normalized relative light units ("RLU") in ligand treated cells with normalized RLU in DMSO treated cells (untreated control).

Figure 3:
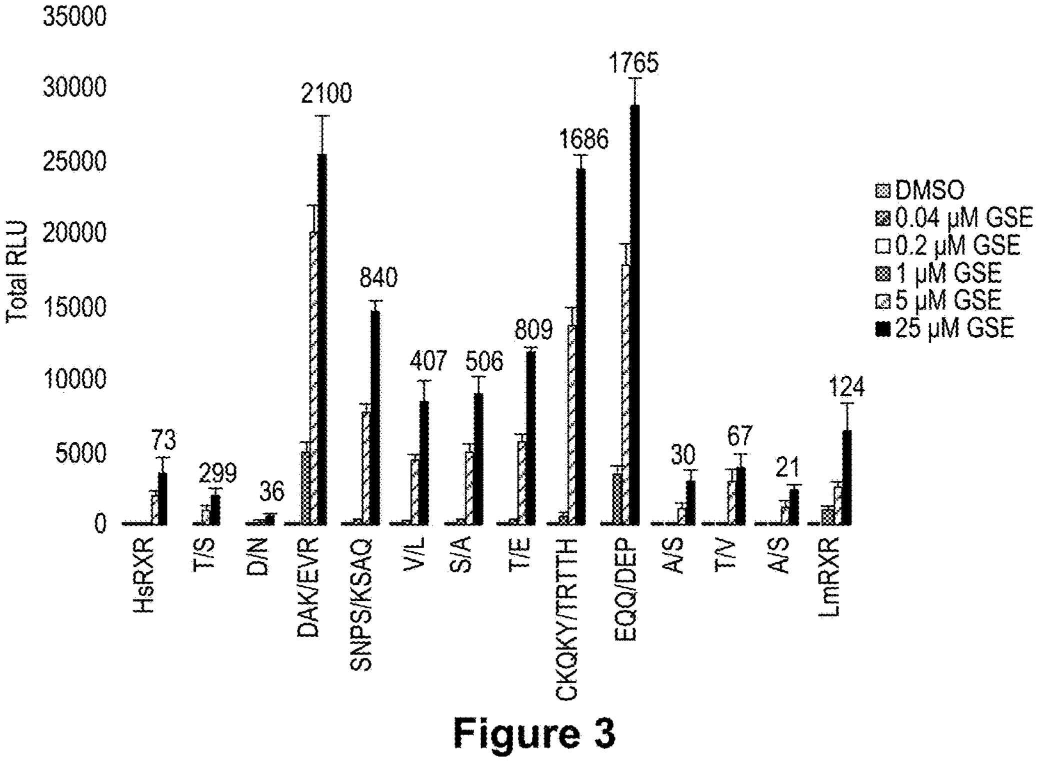
FIG. 3: Reporter gene transactivation of GAL4CfEcRDEF, pFRLUC and VP16HsRXREFβ or its mutant version DNAs transfected into NIH3T3 cells. The transfected calls were grown in the presence of medium containing DMSO or 0.04, 0.2, 1.5, or 25 μM GS™-E in DMSO. Reporter activity was assayed at 48 hours after adding ligands. The numbers on the top of the bars show the maximum fold induction.

As shown in FIG. 3, HsRXRβ-EF substitution mutants T/S, DAK/EVR, SNPS/KSAQ, V/L, S/A, T/E, CKQKY/TRTTH, and EQQ/DEP improved fold induction and magnitude of induction. Applicants' HsRXRβ-EF substitution mutants DAK/EVR, SNPS/KSAQ, V/L, S/A, T/B, CKQKY/TRTTH, and EQQ/DEP also improved non-steroid ligand sensitivity (see FIG. 3).

The results presented in FIG. 3 also show that HsRXRβ-EF substitution mutants D344N, A495S (labeled as A/S with a fold induction of 30), and A528S (labeled a A/S with a fold induction of 21) exhibit reduced fold induction, magnitude of induction, and/or ligand sensitivity compared to wild-type.

Applicants have also determined that these HsRXRβ-EF substitution mutants respond better than wild-type HsRXRβ-EF in the presence of a steroid ligand, ponasterone A (Invitrogen), similar to their response to GS™-E presented in FIG. 3 (data not shown).

Example 4

As discussed above, a CfEcR-based gene regulation system is ligand dependent when RXRs are used as the heterodimeric partner and ligand independent when USPs are used as the heterodimeric partner. However, reporter gene expression is induced at very high levels when CfUSP is used as the heterodimeric partner. To improve RXR as heterodimeric partner, Applicants have aligned the polypeptide sequences of several USP and RXR ligand binding domains (domains EF) and identified amino acid residues that are different between these two nuclear receptor family members. In particular, Applicants identified residues that are conserved in all USPs but are different in RXRs and mutated these residues in HsRXRβ. These substitution mutants were analyzed in NIH3T3 cells as described in Example 2 above in the presence of 0, 0.04, 0.2, 1, 5, or 25 µM GS™-E [N-(2-ethyl-3-methoxybenzoyl)N'-(3,5-dimethylbenzoyl)-N'-tert-butylhydrazine] non-steroidal ligand. The cells were harvested and reporter activity was assayed as described above. Fold activities were calculated by dividing normalized relative light units ("RLU") in ligand treated cells with normalized RLU in DMSO treated cells (untreated control).

Briefly, this Example describes the construction and analysis of substitution mutants in human RXR isoform β-EP (HsRXRβ-EF), wherein amino acid that are different in HsRXR-EF compared to conserved residues of ultraspiracle proteins were mutated to the USP amino acid residue and assayed for their effect on transactivation activity in NIH3T3 cells.

Figure 4:
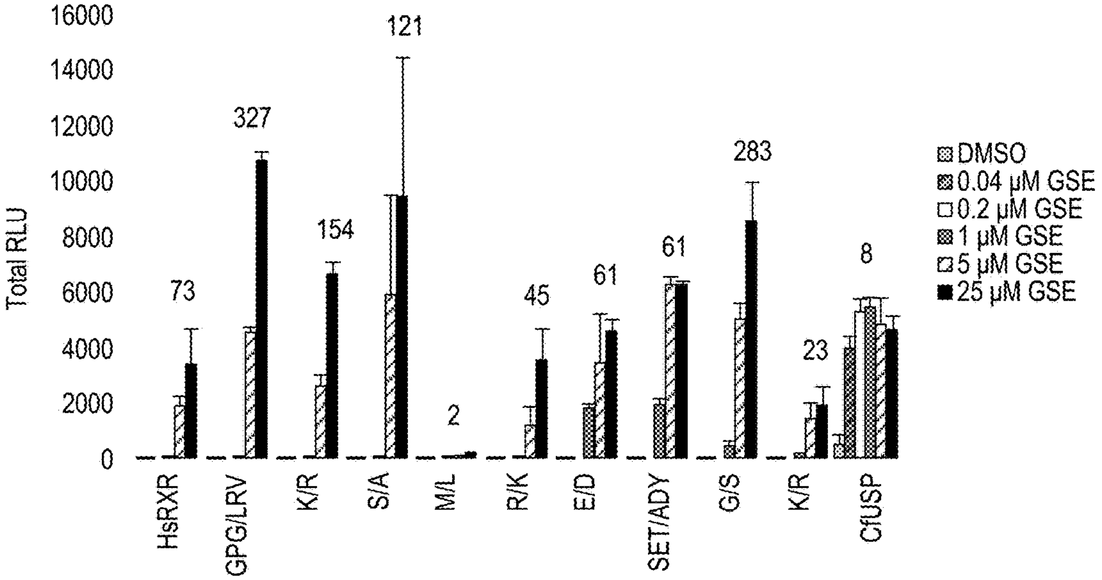
FIG. 4: Reporter gone transactivation of GAL4CfEcRDEF, pFRLUC and VP16HsRXREFβ or its mutant version DNAs transfected into NIH3T3 cells. The transfected cells were grown in the presence of medium containing DMSO or 0.04, 0.2, 1, 5, or 25 μM GS™-E in DMSO. Reporter activity was assayed at 48 hours after adding ligands. The numbers on the top of the bars show the maximum fold induction.

As shown in FIG. 4, HsRXRβ-EF substitution mutants GPG/LRV, K/R, S/A, and G/S improved fold induction and the magnitude of induction of EcR-based gene regulation system. The HsRXR-EF substitution mutants GPG/LRV, S/A, B/D, SET/ADY, and G/S improved ligand sensitivity of the EcR-based gene regulation system (see FIG. 4).

The results presented in FIG. 4 also show that HsRXRβ-EF substitution mutants M431L, R442K, and K511R exhibit reduced fold induction, magnitude of induction, and/or ligand sensitivity compared to wild-type. The HsRXRβ-EP substitution mutant M/L essentially eliminated transactivation activity (see FIG. 4). This M/L mutant is useful in orthogonal ligand screening assays.

Applicants have also determined that these HsRXRβ-EF substitution mutants respond better than wild-type HsRXRβ-EF in the presence of a steroid ligand, ponasterone A (Invitrogen), similar to their response to GS™-E presented in FIG. 4 (data not shown).

We claim:

1. A method of modulating the expression of a gene in a host cell comprising the steps of:

(a) introducing into the host cell a gene expression modulation system; comprising:

(i) a first gene expression cassette comprising a polynucleotide that encodes a first polypeptide, comprising:

(1) a DNA-binding domain that recognizes a response element associated with a gene whose expression is to be modulated; and (2) a first nuclear receptor ligand binding domain; and (ii) a second gene expression cassette comprising a polynucleotide that encodes a second polypeptide, comprising:

(1) a transactivation domain; and (2) a second nuclear receptor ligand binding domain, wherein one of the first and second nuclear receptor ligand binding domains is a Group B nuclear receptor ligand binding domain comprising a substitution mutation at a position selected from the group consisting of (1) 401 or 429 of SEQ ID NO:1, (2) 401 and 429 of SEQ ID NO:1, (3) 337, 462, 470, or 473 of SEQ ID NO:2, (4) 450, 451, and 452 of SEQ ID NO:2, (5) 455, 456, 457, and 458 of SEQ ID NO:2, (6) 475, 476, 477, 478, and 479 of SEQ ID NO:2, and (7) 481, 482, and 483 of SEQ ID NO:2; and the other of said nuclear receptor ligand binding domains is a nuclear receptor ligand binding domain that dimerizes with said Group B nuclear receptor ligand binding domain, and (b) introducing into the host cell a ligand; wherein the gene to be modulated is a component of a gene expression cassette comprising:

(i) a response element recognized by the DNA binding domain;

(ii) a promoter that is activated by the transactivation domain; and (iii) a gene whose expression is to be modulated;

whereby upon introduction of the ligand into the host cell, expression of the gene of (b)(iii) is modulated.

2. The method according to claim 1, wherein the ligand is a) a compound of the formula:

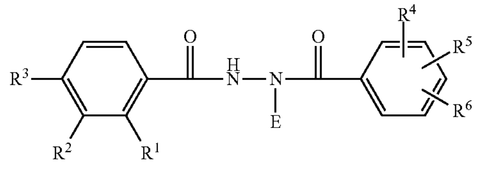

wherein:

E is a ($C_4$-$C_6$)alkyl containing a tertiary carbon or a cyano($C_3$-$C_5$)alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH═CHCN, allyl, azido, SCN, or $SCHF_2$;

$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH═CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$ and $R^6$ are independently H, Me, Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or Set;

b) an ecdysone, 20-hydroxyecdysone, ponasterone A, or muristerone A;

c) an oxysterol, a 22(R) hydroxycholesterol, 24(S) hydroxycholesterol 25-epoxycholesterol, 70901317, 5-alpha-6-alpha-epoxycholesterol-3-sulfate, 7-ketocholesterol-3-sulfate, farnesol, a bile acid, a 1,1-biphosphonate este a Juvenile hormone III; or d) a 9-cis-retinoic acid, 4-(1-(3,5,5,8,8-pentamethyl-5,6,7,8-tetrahydro-2-napthyl)-ethenyl) benzoic acid (3-methyl-TTEB), ((E)-2)2-(5,6,7,8-tetrat-hydro-3,5,5,8,8-pentamethyl-2-napthyl)propen-1-yl)-4-thiophenecarboxylic acid), 2-(5,6,7,8-tetra-hydro-3,5,5,8,8-tetramethyl-2-naphthyl)-2-(carboxyphenyl)-1,3-dioxolane, 4-(5H-2,3-(2,5-dimethyl-2,5-hexano)-5-methyl-dibenzo (b,e) (1.4)diazepin-11-yl)-benzoic acid (HX600) or thiadiazepin analogs thereof, 3,7,11,15-tetramethyl hexadecanoic acid (phytanic acid), 6-(1-(3,5,5,8,8-pentamethyl-5,6,7,8-tetrahydronaphthalen-2-yl) cyclopropyl) nicotinic acid, 2-(4-carboxyphenyl)-2-(5,6,7,8-tetrahydro-5,5,8,8-tetramethyl-2-naphthalenyl)-1,3-dithiane, or 4-(2-methyl)-1-(5,6,7,8-tetrahydro-5,5,8-tetramethyl-2-napthalenyl)propenyl) benzoic acid.

3. The method according to claim 1, wherein the method further comprises introducing into the host cell a second ligand, wherein the second ligand is 9-cis-retinoic acid or a synthetic analog of a retinoic acid.

* * * * *

```
                              SEQUENCE LISTING


<160> NUMBER OF SEQ ID NOS: 75

<210> SEQ ID NO 1
<211> LENGTH: 467
<212> TYPE: PRT
<213> ORGANISM: Mus musculus

<400> SEQUENCE: 1

Met Asp Thr Lys His Phe Leu Pro Leu Asp Phe Ser Thr Gln Val Asn
1               5                   10                  15

Ser Ser Ser Leu Asn Ser Pro Thr Gly Arg Gly Ser Met Ala Val Pro
            20                  25                  30

Ser Leu His Pro Ser Leu Gly Pro Gly Ile Gly Ser Pro Leu Gly Ser
        35                  40                  45

Pro Gly Gln Leu His Ser Pro Ile Ser Thr Leu Ser Ser Pro Ile Asn
    50                  55                  60

Gly Met Gly Pro Pro Phe Ser Val Ile Ser Ser Pro Met Gly Pro His
65                  70                  75                  80

Ser Met Ser Val Pro Thr Thr Pro Thr Leu Gly Phe Gly Thr Gly Ser
                85                  90                  95

Pro Gln Leu Asn Ser Pro Met Asn Pro Val Ser Ser Thr Glu Asp Ile
            100                 105                 110

Lys Pro Pro Leu Gly Leu Asn Gly Val Leu Lys Val Pro Ala His Pro
        115                 120                 125

Ser Gly Asn Met Ala Ser Phe Thr Lys His Ile Cys Ala Ile Cys Gly
    130                 135                 140

Asp Arg Ser Ser Gly Lys His Tyr Gly Val Tyr Ser Cys Glu Gly Cys
145                 150                 155                 160

Lys Gly Phe Phe Lys Arg Thr Val Arg Lys Asp Leu Thr Tyr Thr Cys
                165                 170                 175

Arg Asp Asn Lys Asp Cys Leu Ile Asp Lys Arg Gln Arg Asn Arg Cys
            180                 185                 190

Gln Tyr Cys Arg Tyr Gln Lys Cys Leu Ala Met Gly Met Lys Arg Glu
        195                 200                 205

Ala Val Gln Glu Glu Arg Gln Arg Gly Lys Asp Arg Asn Glu Asn Glu
    210                 215                 220

Val Glu Ser Thr Ser Ser Ala Asn Glu Asp Met Pro Val Glu Lys Ile
225                 230                 235                 240

Leu Glu Ala Glu Leu Ala Val Glu Pro Lys Thr Glu Thr Tyr Val Glu
                245                 250                 255
```

```
Ala Asn Met Gly Leu Asn Pro Ser Ser Pro Asn Asp Pro Val Thr Asn
            260                 265                 270

Ile Cys Gln Ala Ala Asp Lys Gln Leu Phe Thr Leu Val Glu Trp Ala
        275                 280                 285

Lys Arg Ile Pro His Phe Ser Glu Leu Pro Leu Asp Asp Gln Val Ile
    290                 295                 300

Leu Leu Arg Ala Gly Trp Asn Glu Leu Leu Ile Ala Ser Phe Ser His
305                 310                 315                 320

Arg Ser Ile Ala Val Lys Asp Gly Ile Leu Leu Ala Thr Gly Leu His
                325                 330                 335

Val His Arg Asn Ser Ala His Ser Ala Gly Val Gly Ala Ile Phe Asp
            340                 345                 350

Arg Val Leu Thr Glu Leu Val Ser Lys Met Arg Asp Met Gln Met Asp
        355                 360                 365

Lys Thr Glu Leu Gly Cys Leu Arg Ala Ile Val Leu Phe Asn Pro Asp
    370                 375                 380

Ser Lys Gly Leu Ser Asn Pro Ala Glu Val Glu Ala Leu Arg Glu Lys
385                 390                 395                 400

Val Tyr Ala Ser Leu Glu Ala Tyr Cys Lys His Lys Tyr Pro Glu Gln
                405                 410                 415

Pro Gly Arg Phe Ala Lys Leu Leu Leu Arg Leu Pro Ala Leu Arg Ser
            420                 425                 430

Ile Gly Leu Lys Cys Leu Glu His Leu Phe Phe Phe Lys Leu Ile Gly
        435                 440                 445

Asp Thr Pro Ile Asp Thr Phe Leu Met Glu Met Leu Glu Ala Pro His
    450                 455                 460

Gln Ala Thr
465


<210> SEQ ID NO 2
<211> LENGTH: 533
<212> TYPE: PRT
<213> ORGANISM: Homo sapiens

<400> SEQUENCE: 2

Met Ser Trp Ala Ala Arg Pro Pro Phe Leu Pro Gln Arg His Ala Ala
1               5                   10                  15

Gly Gln Cys Gly Pro Val Gly Val Arg Lys Glu Met His Cys Gly Val
            20                  25                  30

Ala Ser Arg Trp Arg Arg Arg Arg Pro Trp Leu Asp Pro Ala Ala Ala
        35                  40                  45

Ala Ala Ala Ala Val Ala Gly Gly Glu Gln Gln Thr Pro Glu Pro Glu
    50                  55                  60

Pro Gly Glu Ala Gly Arg Asp Gly Met Gly Asp Ser Gly Arg Asp Ser
65                  70                  75                  80

Arg Ser Pro Asp Ser Ser Ser Pro Asn Pro Leu Pro Gln Gly Val Pro
                85                  90                  95

Pro Pro Ser Pro Pro Gly Pro Pro Leu Pro Pro Ser Thr Ala Pro Ser
            100                 105                 110

Leu Gly Gly Ser Gly Ala Pro Pro Pro Pro Pro Met Pro Pro Pro Pro
        115                 120                 125

Leu Gly Ser Pro Phe Pro Val Ile Ser Ser Ser Met Gly Ser Pro Gly
    130                 135                 140

Leu Pro Pro Pro Ala Pro Pro Gly Phe Ser Gly Pro Val Ser Ser Pro
145                 150                 155                 160
```

-continued

```
Gln Ile Asn Ser Thr Val Ser Leu Pro Gly Gly Gly Ser Gly Pro Pro
                165                 170                 175

Glu Asp Val Lys Pro Pro Val Leu Gly Val Arg Gly Leu His Cys Pro
            180                 185                 190

Pro Pro Pro Gly Gly Pro Gly Ala Gly Lys Arg Leu Cys Ala Ile Cys
        195                 200                 205

Gly Asp Arg Ser Ser Gly Lys His Tyr Gly Val Tyr Ser Cys Glu Gly
    210                 215                 220

Cys Lys Gly Phe Phe Lys Arg Thr Ile Arg Lys Asp Leu Thr Tyr Ser
225                 230                 235                 240

Cys Arg Asp Asn Lys Asp Cys Thr Val Asp Lys Arg Gln Arg Asn Arg
                245                 250                 255

Cys Gln Tyr Cys Arg Tyr Gln Lys Cys Leu Ala Thr Gly Met Lys Arg
            260                 265                 270

Glu Ala Val Gln Glu Glu Arg Gln Arg Gly Lys Asp Lys Asp Gly Asp
        275                 280                 285

Gly Glu Gly Ala Gly Gly Ala Pro Glu Glu Met Pro Val Asp Arg Ile
    290                 295                 300

Leu Glu Ala Glu Leu Ala Val Glu Gln Lys Ser Asp Gln Gly Val Glu
305                 310                 315                 320

Gly Pro Gly Gly Thr Gly Gly Ser Gly Ser Ser Pro Asn Asp Pro Val
                325                 330                 335

Thr Asn Ile Cys Gln Ala Ala Asp Lys Gln Leu Phe Thr Leu Val Glu
            340                 345                 350

Trp Ala Lys Arg Ile Pro His Phe Ser Ser Leu Pro Leu Asp Asp Gln
        355                 360                 365

Val Ile Leu Leu Arg Ala Gly Trp Asn Glu Leu Leu Ile Ala Ser Phe
    370                 375                 380

Ser His Arg Ser Ile Asp Val Arg Asp Gly Ile Leu Leu Ala Thr Gly
385                 390                 395                 400

Leu His Val His Arg Asn Ser Ala His Ser Ala Gly Val Gly Ala Ile
                405                 410                 415

Phe Asp Arg Val Leu Thr Glu Leu Val Ser Lys Met Arg Asp Met Arg
            420                 425                 430

Met Asp Lys Thr Glu Leu Gly Cys Leu Arg Ala Ile Ile Leu Phe Asn
        435                 440                 445

Pro Asp Ala Lys Gly Leu Ser Asn Pro Ser Glu Val Glu Val Leu Arg
    450                 455                 460

Glu Lys Val Tyr Ala Ser Leu Glu Thr Tyr Cys Lys Gln Lys Tyr Pro
465                 470                 475                 480

Glu Gln Gln Gly Arg Phe Ala Lys Leu Leu Leu Arg Leu Pro Ala Leu
                485                 490                 495

Arg Ser Ile Gly Leu Lys Cys Leu Glu His Leu Phe Phe Phe Lys Leu
            500                 505                 510

Ile Gly Asp Thr Pro Ile Asp Thr Phe Leu Met Glu Met Leu Glu Ala
        515                 520                 525

Pro His Gln Leu Ala
    530
```

<210> SEQ ID NO 3
<211> LENGTH: 198
<212> TYPE: DNA
<213> ORGANISM: Choristoneura fumiferana

<400> SEQUENCE: 3
tgtctggtat gcggggacag agcctccgga taccactaca atgcgctcac gtgtgaaggg 60
tgtaaagggt tcttcagacg gagtgttacc aaaaatgcgg tttatatttg taaattcggt 120
cacgcttgcg aaatggacat gtacatgcga cggaaatgcc aggagtgccg cctgaagaag 180
tgcttagctg taggcatg 198

<210> SEQ ID NO 4
<211> LENGTH: 66
<212> TYPE: PRT
<213> ORGANISM: Choristoneura fumiferana

<400> SEQUENCE: 4

Cys Leu Val Cys Gly Asp Arg Ala Ser Gly Tyr His Tyr Asn Ala Leu
1 5 10 15

Thr Cys Glu Gly Cys Lys Gly Phe Phe Arg Arg Ser Val Thr Lys Asn
20 25 30

Ala Val Tyr Ile Cys Lys Phe Gly His Ala Cys Glu Met Asp Met Tyr
35 40 45

Met Arg Arg Lys Cys Gln Glu Cys Arg Leu Lys Lys Cys Leu Ala Val
50 55 60

Gly Met
65

<210> SEQ ID NO 5
<211> LENGTH: 441
<212> TYPE: DNA
<213> ORGANISM: Saccharomyces cerevisiae

<400> SEQUENCE: 5
atgaagctac tgtcttctat cgaacaagca tgcgatattt gccgacttaa aaagctcaag 60
tgctccaaag aaaaaccgaa gtgcgccaag tgtctgaaga acaactggga gtgtcgctac 120
tctcccaaaa ccaaaaggtc tccgctgact agggcacatc tgacagaagt ggaatcaagg 180
ctagaaagac tggaacagct atttctactg atttttcctc gagaagacct tgacatgatt 240
ttgaaaatgg attctttaca ggatataaaa gcattgttaa caggattatt tgtacaagat 300
aatgtgaata aagatgccgt cacagataga ttggcttcag tggagactga tatgcctcta 360
acattgagac agcatagaat aagtgcgaca tcatcatcgg aagagagtag taacaaaggt 420
caaagacagt tgactgtatc g 441

<210> SEQ ID NO 6
<211> LENGTH: 147
<212> TYPE: PRT
<213> ORGANISM: Saccharomyces cerevisiae

<400> SEQUENCE: 6

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

-continued

```
Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145
```

<210> SEQ ID NO 7
<211> LENGTH: 606
<212> TYPE: DNA
<213> ORGANISM: Escherichia coli

<400> SEQUENCE: 7

```
atgaaagcgt taacggccag gcaacaagag gtgtttgatc tcatccgtga tcacatcagc      60

cagacaggta tgccgccgac gcgtgcggaa atcgcgcagc gtttggggtt ccgttcccca     120

aacgcggctg aagaacatct gaaggcgctg gcacgcaaag gcgttattga aattgtttcc     180

ggcgcatcac gcgggattcg tctgttgcag gaagaggaag aagggttgcc gctggtaggt     240

cgtgtggctg ccggtgaacc acttctggcg caacagcata ttgaaggtca ttatcaggtc     300

gatccttcct tattcaagcc gaatgctgat ttcctgctgc gcgtcagcgg gatgtcgatg     360

aaagatatcg gcattatgga tggtgacttg ctggcagtgc ataaaactca ggatgtacgt     420

aacggtcagg tcgttgtcgc acgtattgat gacgaagtta ccgttaagcg cctgaaaaaa     480

cagggcaata aagtcgaact gttgccagaa aatagcgagt ttaaaccaat tgtcgtagat     540

cttcgtcagc agagcttcac cattgaaggg ctggcggttg gggttattcg caacggcgac     600

tggctg                                                                606
```

<210> SEQ ID NO 8
<211> LENGTH: 202
<212> TYPE: PRT
<213> ORGANISM: Escherichia coli

<400> SEQUENCE: 8

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140
```

Val Val Ala Arg Ile Asp Asp Glu Val Thr Val Lys Arg Leu Lys Lys
145 150 155 160

Gln Gly Asn Lys Val Glu Leu Leu Pro Glu Asn Ser Glu Phe Lys Pro
165 170 175

Ile Val Val Asp Leu Arg Gln Gln Ser Phe Thr Ile Glu Gly Leu Ala
180 185 190

Val Gly Val Ile Arg Asn Gly Asp Trp Leu
195 200

<210> SEQ ID NO 9
<211> LENGTH: 420
<212> TYPE: DNA
<213> ORGANISM: Choristoneura fumiferana

<400> SEQUENCE: 9
atgagacgcc gctggtccaa caacgggggc ttccagacgc tgcgaatgct cgaggagagc 60
tcgtccgaag tgacgtcgtc ctcagctctg ggtctgccgg ccgcgatggt tatgtctccg 120
gagtcgctcg cctcgccaga gtacggcggg ctcgagctct ggggatacga cgatgggttg 180
tcatacaaca cggcgcagtc cttgctgggc aatacttgca cgatgcagca gcagcaacag 240
acgcagccgc tgccgtcgat gccgttgcct atgccgccga ccacgccgaa gtctgaaaac 300
gagtctattt cctcaggccg tgaggaactg tcgccagctt caagtataaa tgggtgcagt 360
acagatggcg aggcacgacg tcagaagaag ggccctgcgc cccgtcagca agaggaactg 420

<210> SEQ ID NO 10
<211> LENGTH: 140
<212> TYPE: PRT
<213> ORGANISM: Choristoneura fumiferana

<400> SEQUENCE: 10

Met Arg Arg Arg Trp Ser Asn Asn Gly Gly Phe Gln Thr Leu Arg Met
1 5 10 15

Leu Glu Glu Ser Ser Ser Glu Val Thr Ser Ser Ser Ala Leu Gly Leu
20 25 30

Pro Ala Ala Met Val Met Ser Pro Glu Ser Leu Ala Ser Pro Glu Tyr
35 40 45

Gly Gly Leu Glu Leu Trp Gly Tyr Asp Asp Gly Leu Ser Tyr Asn Thr
50 55 60

Ala Gln Ser Leu Leu Gly Asn Thr Cys Thr Met Gln Gln Gln Gln Gln
65 70 75 80

Thr Gln Pro Leu Pro Ser Met Pro Leu Pro Met Pro Pro Thr Thr Pro
85 90 95

Lys Ser Glu Asn Glu Ser Ile Ser Ser Gly Arg Glu Glu Leu Ser Pro
100 105 110

Ala Ser Ser Ile Asn Gly Cys Ser Thr Asp Gly Glu Ala Arg Arg Gln
115 120 125

Lys Lys Gly Pro Ala Pro Arg Gln Gln Glu Glu Leu
130 135 140

<210> SEQ ID NO 11
<211> LENGTH: 271
<212> TYPE: DNA
<213> ORGANISM: herpes simplex virus 7

<400> SEQUENCE: 11
atgggcccta aaaagaagcg taaagtcgcc cccccgaccg atgtcagcct gggggacgag 60
ctccacttag acggcgagga cgtggcgatg gcgcatgccg acgcgctaga cgatttcgat 120
ctggacatgt tgggggacgg ggattccccg ggccgggat ttacccccca cgactccgcc 180
ccctacggcg ctctggatat ggccgacttc gagtttgagc agatgtttac cgatgccctt 240
ggaattgacg agtacggtgg ggaattcccg g 271

<210> SEQ ID NO 12
<211> LENGTH: 90
<212> TYPE: PRT
<213> ORGANISM: herpes simplex virus 7

<400> SEQUENCE: 12

Met Gly Pro Lys Lys Lys Arg Lys Val Ala Pro Pro Thr Asp Val Ser
1 5 10 15

Leu Gly Asp Glu Leu His Leu Asp Gly Glu Asp Val Ala Met Ala His
20 25 30

Ala Asp Ala Leu Asp Asp Phe Asp Leu Asp Met Leu Gly Asp Gly Asp
35 40 45

Ser Pro Gly Pro Gly Phe Thr Pro His Asp Ser Ala Pro Tyr Gly Ala
50 55 60

Leu Asp Met Ala Asp Phe Glu Phe Glu Gln Met Phe Thr Asp Ala Leu
65 70 75 80

Gly Ile Asp Glu Tyr Gly Gly Glu Phe Pro
85 90

<210> SEQ ID NO 13
<211> LENGTH: 307
<212> TYPE: DNA
<213> ORGANISM: Saccharomyces cerevisiae

<400> SEQUENCE: 13
atgggtgctc ctccaaaaaa gaagagaaag gtagctggta tcaataaaga tatcgaggag 60
tgcaatgcca tcattgagca gtttatcgac tacctgcgca ccggacagga gatgccgatg 120
gaaatggcgg atcaggcgat taacgtggtg ccgggcatga cgccgaaaac cattcttcac 180
gccgggccgc cgatccagcc tgactggctg aaatcgaatg gttttcatga aattgaagcg 240
gatgttaacg ataccagcct cttgctgagt ggagatgcct cctacccttta tgatgtgcca 300 gattatg 307

<210> SEQ ID NO 14
<211> LENGTH: 102
<212> TYPE: PRT
<213> ORGANISM: Saccharomyces cerevisiae

<400> SEQUENCE: 14

Met Gly Ala Pro Pro Lys Lys Lys Arg Lys Val Ala Gly Ile Asn Lys
1 5 10 15

Asp Ile Glu Glu Cys Asn Ala Ile Ile Glu Gln Phe Ile Asp Tyr Leu
20 25 30

Arg Thr Gly Gln Glu Met Pro Met Glu Met Ala Asp Gln Ala Ile Asn
35 40 45

Val Val Pro Gly Met Thr Pro Lys Thr Ile Leu His Ala Gly Pro Pro
50 55 60

```
Ile Gln Pro Asp Trp Leu Lys Ser Asn Gly Phe His Glu Ile Glu Ala
65                  70                  75                  80

Asp Val Asn Asp Thr Ser Leu Leu Leu Ser Gly Asp Ala Ser Tyr Pro
                85                  90                  95

Tyr Asp Val Pro Asp Tyr
            100


<210> SEQ ID NO 15
<211> LENGTH: 807
<212> TYPE: DNA
<213> ORGANISM: Homo sapiens

<400> SEQUENCE: 15

cccatggaat tccagtacct gccagataca gacgatcgtc accggattga ggagaaacgt      60

aaaaggacat atgagacctt caagagcatc atgaagaaga gtcctttcag cggacccacc     120

gacccccggc ctccacctcg acgcattgct gtgccttccc gcagctcagc ttctgtcccc     180

aagccagcac cccagcccta tccctttacg tcatccctga gcaccatcaa ctatgatgag     240

tttcccacca tggtgtttcc ttctgggcag atcagccagg cctcggcctt ggccccggcc     300

cctccccaag tcctgcccca ggctccagcc cctgcccctg ctccagccat ggtatcagct     360

ctggcccagg ccccagcccc tgtcccagtc ctagccccag gccctcctca ggctgtggcc     420

ccacctgccc ccaagcccac ccaggctggg gaaggaacgc tgtcagaggc cctgctgcag     480

ctgcagtttg atgatgaaga cctgggggcc ttgcttggca acagcacaga cccagctgtg     540

ttcacagacc tggcatccgt cgacaactcc gagtttcagc agctgctgaa ccagggcata     600

cctgtggccc cccacacaac tgagcccatg ctgatggagt accctgaggc tataactcgc     660

ctagtgacag ggcccagag gcccccgac ccagctcctg ctccactggg ggccccgggg       720

ctccccaatg gcctcctttc aggagatgaa gacttctcct ccattgcgga catggacttc     780

tcagccctgc tgagtcagat cagctcc                                         807


<210> SEQ ID NO 16
<211> LENGTH: 269
<212> TYPE: PRT
<213> ORGANISM: Homo sapiens

<400> SEQUENCE: 16

Pro Met Glu Phe Gln Tyr Leu Pro Asp Thr Asp Asp Arg His Arg Ile
1               5                   10                  15

Glu Glu Lys Arg Lys Arg Thr Tyr Glu Thr Phe Lys Ser Ile Met Lys
            20                  25                  30

Lys Ser Pro Phe Ser Gly Pro Thr Asp Pro Arg Pro Pro Pro Arg Arg
        35                  40                  45

Ile Ala Val Pro Ser Arg Ser Ser Ala Ser Val Pro Lys Pro Ala Pro
    50                  55                  60

Gln Pro Tyr Pro Phe Thr Ser Ser Leu Ser Thr Ile Asn Tyr Asp Glu
65                  70                  75                  80

Phe Pro Thr Met Val Phe Pro Ser Gly Gln Ile Ser Gln Ala Ser Ala
                85                  90                  95

Leu Ala Pro Ala Pro Pro Gln Val Leu Pro Gln Ala Pro Ala Pro Ala
            100                 105                 110

Pro Ala Pro Ala Met Val Ser Ala Leu Ala Gln Ala Pro Ala Pro Val
        115                 120                 125

Pro Val Leu Ala Pro Gly Pro Pro Gln Ala Val Ala Pro Pro Ala Pro
    130                 135                 140
```

-continued

```
Lys Pro Thr Gln Ala Gly Glu Gly Thr Leu Ser Glu Ala Leu Leu Gln
145                 150                 155                 160

Leu Gln Phe Asp Asp Glu Asp Leu Gly Ala Leu Leu Gly Asn Ser Thr
                165                 170                 175

Asp Pro Ala Val Phe Thr Asp Leu Ala Ser Val Asp Asn Ser Glu Phe
            180                 185                 190

Gln Gln Leu Leu Asn Gln Gly Ile Pro Val Ala Pro His Thr Thr Glu
        195                 200                 205

Pro Met Leu Met Glu Tyr Pro Glu Ala Ile Thr Arg Leu Val Thr Gly
    210                 215                 220

Ala Gln Arg Pro Pro Asp Pro Ala Pro Ala Pro Leu Gly Ala Pro Gly
225                 230                 235                 240

Leu Pro Asn Gly Leu Leu Ser Gly Asp Glu Asp Phe Ser Ser Ile Ala
                245                 250                 255

Asp Met Asp Phe Ser Ala Leu Leu Ser Gln Ile Ser Ser
            260                 265


<210> SEQ ID NO 17
<211> LENGTH: 34
<212> TYPE: DNA
<213> ORGANISM: Artificial Sequence
<220> FEATURE:
<223> OTHER INFORMATION: 1X Ecdysone response element (EcRE)

<400> SEQUENCE: 17

tcgagagaca agggttcaat gcacttgtcc aatg                                34


<210> SEQ ID NO 18
<211> LENGTH: 19
<212> TYPE: DNA
<213> ORGANISM: Artificial Sequence
<220> FEATURE:
<223> OTHER INFORMATION: GAL4 response element

<400> SEQUENCE: 18

ggagtactgt cctccgagc                                                 19


<210> SEQ ID NO 19
<211> LENGTH: 36
<212> TYPE: DNA
<213> ORGANISM: Artificial Sequence
<220> FEATURE:
<223> OTHER INFORMATION: 2xLexAop response element

<400> SEQUENCE: 19

ctgctgtata taaaaccagt ggttatatgt acagta                              36


<210> SEQ ID NO 20
<211> LENGTH: 1054
<212> TYPE: DNA
<213> ORGANISM: Choristoneura fumiferana

<400> SEQUENCE: 20

cctgagtgcg tagtacccga gactcagtgc gccatgaagc ggaaagagaa gaaagcacag     60

aaggagaagg acaaactgcc tgtcagcacg acgacggtgg acgaccacat gccgcccatt    120

atgcagtgtg aacctccacc tcctgaagca gcaaggattc acgaagtggt cccaaggttt    180

ctctccgaca agctgttgga gacaaaccgg cagaaaaaca tcccccagtt gacagccaac    240

cagcagttcc ttatcgccag gctcatctgg taccaggacg ggtacgagca gccttctgat    300

gaagatttga agaggattac gcagacgtgg cagcaagcgg acgatgaaaa cgaagagtct    360
```

gacactccct tccgccagat cacagagatg actatcctca cggtccaact tatcgtggag 420
ttcgcgaagg gattgccagg gttcgccaag atctcgcagc ctgatcaaat tacgctgctt 480
aaggcttgct caagtgaggt aatgatgctc cgagtcgcgc gacgatacga tgcggcctca 540
gacagtgttc tgttcgcgaa caaccaagcg tacactcgcg acaactaccg caaggctggc 600
atggcctacg tcatcgagga tctactgcac ttctgccggt gcatgtactc tatggcgttg 660
gacaacatcc attacgcgct gctcacggct gtcgtcatct ttctgaccg gccagggttg 720 gagcagccgc aactggtgga agaaatccag cggtactacc tgaatacgct ccgcatctat 780
atcctgaacc agctgagcgg gtcggcgcgt tcgtccgtca tatacggcaa gatcctctca 840
atcctctctg agctacgcac gctcggcatg caaaactcca acatgtgcat ctccctcaag 900
ctcaagaaca gaaagctgcc gcctttcctc gaggagatct gggatgtggc ggacatgtcg 960
cacacccaac cgccgcctat cctcgagtcc cccacgaatc tctagcccct gcgcgcacgc 1020
atcgccgatg ccgcgtccgg ccgcgctgct ctga 1054

<210> SEQ ID NO 21
<211> LENGTH: 309
<212> TYPE: DNA
<213> ORGANISM: Simian virus 40

<400> SEQUENCE: 21
ggtgtggaaa gtccccaggc tccccagcag gcagaagtat gcaaagcatg catctcaatt 60
agtcagcaac caggtgtgga aagtccccag gctccccagc aggcagaagt atgcaaagca 120
tgcatctcaa ttagtcagca accatagtcc cgcccctaac tccgcccatc ccgcccctaa 180
ctccgcccag ttccgcccat tctccgcccc atggctgact aattttttt atttatgcag 240 aggccgaggc cgcctcggcc tctgagctat tccagaagta gtgaggaggc ttttttggag 300
gcctaggct 309

<210> SEQ ID NO 22
<211> LENGTH: 635
<212> TYPE: DNA
<213> ORGANISM: Locusta migratoria

<400> SEQUENCE: 22
tgcatacaga catgcctgtt gaacgcatac ttgaagctga aaaacgagtg gagtgcaaag 60
cagaaaacca agtggaatat gagctggtgg agtgggctaa acacatcccg cacttcacat 120
ccctacctct ggaggaccag gttctcctcc tcagagcagg ttggaatgaa ctgctaattg 180
cagcattttc acatcgatct gtagatgtta aagatggcat agtacttgcc actggtctca 240
cagtgcatcg aaattctgcc catcaagctg gagtcggcac aatatttgac agagttttga 300
cagaactggt agcaaagatg agagaaatga aaatggataa aactgaactt ggctgcttgc 360
gatctgttat tcttttcaat ccagaggtga ggggtttgaa atccgcccag gaagttgaac 420
ttctacgtga aaaagtatat gccgctttgg aagaatatac tagaacaaca catcccgatg 480
aaccaggaag atttgcaaaa cttttgcttc gtctgccttc tttacgttcc ataggcctta 540
agtgtttgga gcatttgttt ttctttcgcc ttattggaga tgttccaatt gatacgttcc 600
tgatggagat gcttgaatca ccttctgatt cataa 635

<210> SEQ ID NO 23
<211> LENGTH: 24
<212> TYPE: DNA
<213> ORGANISM: Artificial Sequence
<220> FEATURE:
<223> OTHER INFORMATION: synthetic E1b minimal promoter

<400> SEQUENCE: 23
tatataatgg atccccgggt accg 24

<210> SEQ ID NO 24
<211> LENGTH: 1653
<212> TYPE: DNA
<213> ORGANISM: Photinus pyralis

<400> SEQUENCE: 24
atggaagacg ccaaaaacat aaagaaaggc ccggcgccat tctatcctct agaggatgga 60
accgctggag agcaactgca taaggctatg aagagatacg ccctggttcc tggaacaatt 120
gcttttacag atgcacatat cgaggtgaac atcacgtacg cggaatactt cgaaatgtcc 180
gttcggttgg cagaagctat gaaacgatat gggctgaata caaatcacag aatcgtcgta 240
tgcagtgaaa actctcttca attctttatg ccggtgttgg gcgcgttatt tatcggagtt 300
gcagttgcgc ccgcgaacga catttataat gaacgtgaat tgctcaacag tatgaacatt 360
tcgcagccta ccgtagtgtt tgtttccaaa aaggggttgc aaaaaatttt gaacgtgcaa 420
aaaaaattac caataatcca gaaaattatt atcatggatt ctaaaacgga ttaccaggga 480
tttcagtcga tgtacacgtt cgtcacatct catctacctc ccggttttaa tgaatacgat 540
tttgtaccag agtcctttga tcgtgacaaa acaattgcac tgataatgaa ttcctctgga 600
tctactgggt tacctaaggg tgtggccctt ccgcatagaa ctgcctgcgt cagattctcg 660
catgccagag atcctatttt tggcaatcaa atcattccgg atactgcgat tttaagtgtt 720
gttccattcc atcacggttt tggaatgttt actacactcg gatatttgat atgtggattt 780
cgagtcgtct taatgtatag atttgaagaa gagctgtttt tacgatccct tcaggattac 840
aaaattcaaa gtgcgttgct agtaccaacc ctattttcat tcttcgccaa aagcactctg 900
attgacaaat acgatttatc taatttacac gaaattgctt ctgggggcgc acctctttcg 960
aaagaagtcg gggaagcggt tgcaaaacgc ttccatcttc cagggatacg acaaggatat 1020
gggctcactg agactacatc agctattctg attacacccg agggggatga taaaccgggc 1080
gcggtcggta aagttgttcc atttttttgaa gcgaaggttg tggatctgga taccgggaaa 1140
acgctgggcg ttaatcagag aggcgaatta tgtgtcagag gacctatgat tatgtccggt 1200
tatgtaaaca atccggaagc gaccaacgcc ttgattgaca aggatggatg gctacattct 1260
ggagacatag cttactggga cgaagacgaa cacttcttca tagttgaccg cttgaagtct 1320
ttaattaaat acaaaggata tcaggtggcc cccgctgaat tggaatcgat attgttacaa 1380
caccccaaca tcttcgacgc gggcgtggca ggtcttcccg acgatgacgc cggtgaactt 1440
cccgccgccg ttgttgtttt ggagcacgga aagacgatga cggaaaaaga gatcgtggat 1500
tacgtcgcca gtcaagtaac aaccgcgaaa aagttgcgcg gaggagttgt gtttgtggac 1560
gaagtaccga aaggtcttac cggaaaactc gacgcaagaa aaatcagaga gatcctcata 1620
aaggccaaga agggcggaaa gtccaaattg taa 1653

<210> SEQ ID NO 25
<211> LENGTH: 714
<212> TYPE: DNA
<213> ORGANISM: Mus musculus -continued

<400> SEQUENCE: 25
gccaacgagg acatgcctgt agagaagatt ctggaagccg agcttgctgt cgagcccaag 60
actgagacat acgtggaggc aaacatgggg ctgaacccca gctcaccaaa tgaccctgtt 120
accaacatct gtcaagcagc agacaagcag ctcttcactc ttgtggagtg ggccaagagg 180
atcccacact tttctgagct gcccctagac gaccaggtca tcctgctacg ggcaggctgg 240
aacgagctgc tgatcgcctc cttctcccac cgctccatag ctgtgaaaga tgggattctc 300
ctggccaccg gcctgcacgt acaccggaac agcgctcaca gtgctggggt gggcgccatc 360
tttgacaggg tgctaacaga gctggtgtct aagatgcgtg acatgcagat ggacaagacg 420
gagctgggct gcctgcgagc cattgtcctg ttcaaccctg actctaaggg gctctcaaac 480
cctgctgagg tggaggcgtt gagggagaag gtgtatgcgt cactagaagc gtactgcaaa 540
cacaagtacc ctgagcagcc gggcaggttt gccaagctgc tgctccgcct gcctgcactg 600
cgttccatcg ggctcaagtg cctggagcac ctgttcttct tcaagctcat cggggacacg 660
cccatcgaca ccttcctcat ggagatgctg gaggcaccac atcaagccac ctag 714

<210> SEQ ID NO 26
<211> LENGTH: 711
<212> TYPE: DNA
<213> ORGANISM: Artificial Sequence
<220> FEATURE:
<223> OTHER INFORMATION: MmRXRalpha helices 1-7-LmUSP helices 8-12-
chimeric EF domains

<400> SEQUENCE: 26
gccaacgagg acatgcctgt agagaagatt ctggaagccg agcttgctgt cgagcccaag 60
actgagacat acgtggaggc aaacatgggg ctgaacccca gctcaccaaa tgaccctgtt 120
accaacatct gtcaagcagc agacaagcag ctcttcactc ttgtggagtg ggccaagagg 180
atcccacact tttctgagct gcccctagac gaccaggtca tcctgctacg ggcaggctgg 240
aacgagctgc tgatcgcctc cttctcccac cgctccatag ctgtgaaaga tgggattctc 300
ctggccaccg gcctgcacgt acaccggaac agcgctcaca gtgctggggt gggcgccatc 360
tttgacaggg tgctaacaga gctggtgtct aagatgcgtg acatgcagat ggacaagact 420
gaacttggct gcttgcgatc tgttattctt ttcaatccag aggtgagggg tttgaaatcc 480
gcccaggaag ttgaacttct acgtgaaaaa gtatatgccg ctttggaaga atatactaga 540
acaacacatc ccgatgaacc aggaagattt gcaaaacttt tgcttcgtct gccttcttta 600
cgttccatag gccttaagtg tttggagcat ttgtttttct ttcgccttat tggagatgtt 660
ccaattgata cgttcctgat ggagatgctt gaatcacctt ctgattcata a 711

<210> SEQ ID NO 27
<211> LENGTH: 720
<212> TYPE: DNA
<213> ORGANISM: Homo sapiens

<400> SEQUENCE: 27
gcccccgagg agatgcctgt ggacaggatc ctggaggcag agcttgctgt ggaacagaag 60
agtgaccagg gcgttgaggg tcctggggga accgggggta gcggcagcag cccaaatgac 120
cctgtgacta acatctgtca ggcagctgac aaacagctat tcacgcttgt tgagtgggcg 180
aagaggatcc cacacttttc ctccttgcct ctggatgatc aggtcatatt gctgcgggca 240
ggctggaatg aactcctcat tgcctccttt tcacaccgat ccattgatgt tcgagatggc 300

-continued atcctccttg ccacaggtct tcacgtgcac cgcaactcag cccattcagc aggagtagga 360
gccatctttg atcgggtgct gacagagcta gtgtccaaaa tgcgtgacat gaggatggac 420
aagacagagc ttggctgcct gagggcaatc attctgttta atccagatgc caagggcctc 480
tccaacccta gtgaggtgga ggtcctgcgg gagaaagtgt atgcatcact ggagacctac 540
tgcaaacaga agtaccctga gcagcaggga cggtttgcca agctgctgct acgtcttcct 600
gccctccggt ccattggcct taagtgtcta gagcatctgt ttttcttcaa gctcattggt 660 gacacccca tcgacacctt cctcatggag atgcttgagg ctccccatca actggcctga 720

<210> SEQ ID NO 28
<211> LENGTH: 33
<212> TYPE: DNA
<213> ORGANISM: Artificial Sequence
<220> FEATURE:
<223> OTHER INFORMATION: PCR primer

<400> SEQUENCE: 28
gtgtatgcgt cactagatgc gtactgcaaa cac 33

<210> SEQ ID NO 29
<211> LENGTH: 33
<212> TYPE: DNA
<213> ORGANISM: Artificial Sequence
<220> FEATURE:
<223> OTHER INFORMATION: PCR primer

<400> SEQUENCE: 29
gtgtttgcag tacgcatcta gtgacgcata cac 33

<210> SEQ ID NO 30
<211> LENGTH: 33
<212> TYPE: DNA
<213> ORGANISM: Artificial Sequence
<220> FEATURE:
<223> OTHER INFORMATION: PCR primer

<400> SEQUENCE: 30
gcactgcgtt ccatcagcct caagtgcctg gag 33

<210> SEQ ID NO 31
<211> LENGTH: 33
<212> TYPE: DNA
<213> ORGANISM: Artificial Sequence
<220> FEATURE:
<223> OTHER INFORMATION: PCR primer

<400> SEQUENCE: 31
ctccaggcac ttgaggctga tggaacgcag tgc 33

<210> SEQ ID NO 32
<211> LENGTH: 39
<212> TYPE: DNA
<213> ORGANISM: Artificial Sequence
<220> FEATURE:
<223> OTHER INFORMATION: PCR primer

<400> SEQUENCE: 32
gaccagggcg ttgagcgtcg tgtgggaacc gggggtagc 39

<210> SEQ ID NO 33
<211> LENGTH: 39
<212> TYPE: DNA
<213> ORGANISM: Artificial Sequence
<220> FEATURE:
<223> OTHER INFORMATION: PCR primer

<400> SEQUENCE: 33
gctacccccg gttcccacac gacgctcaac gccctggtc 39

<210> SEQ ID NO 34
<211> LENGTH: 32
<212> TYPE: DNA
<213> ORGANISM: Artificial Sequence
<220> FEATURE:
<223> OTHER INFORMATION: PCR primer

<400> SEQUENCE: 34
ccaaatgacc ctgtgtctaa catctgtcag gc 32

<210> SEQ ID NO 35
<211> LENGTH: 32
<212> TYPE: DNA
<213> ORGANISM: Artificial Sequence
<220> FEATURE:
<223> OTHER INFORMATION: PCR primer

<400> SEQUENCE: 35
gcctgacaga tgttagacac agggtcattt gg 32

<210> SEQ ID NO 36
<211> LENGTH: 33
<212> TYPE: DNA
<213> ORGANISM: Artificial Sequence
<220> FEATURE:
<223> OTHER INFORMATION: PCR primer

<400> SEQUENCE: 36
atctgtcagg cagctaacaa acagctattc acg 33

<210> SEQ ID NO 37
<211> LENGTH: 33
<212> TYPE: DNA
<213> ORGANISM: Artificial Sequence
<220> FEATURE:
<223> OTHER INFORMATION: PCR primer

<400> SEQUENCE: 37
cgtgaatagc tgtttgttag ctgcctgaca gat 33

<210> SEQ ID NO 38
<211> LENGTH: 35
<212> TYPE: DNA
<213> ORGANISM: Artificial Sequence
<220> FEATURE:
<223> OTHER INFORMATION: PCR primer

<400> SEQUENCE: 38
cttgttgagt gggcgaggag gatcccacac ttttc 35

<210> SEQ ID NO 39
<211> LENGTH: 35
<212> TYPE: DNA
<213> ORGANISM: Artificial Sequence
<220> FEATURE:
<223> OTHER INFORMATION: PCR primer

<400> SEQUENCE: 39
gaaaagtgtg ggatcctcct cgcccactca acaag 35

-continued

<210> SEQ ID NO 40
<211> LENGTH: 34
<212> TYPE: DNA
<213> ORGANISM: Artificial Sequence
<220> FEATURE:
<223> OTHER INFORMATION: PCR primer

<400> SEQUENCE: 40
ctcattgcct cctttgcaca ccgatccatt gatg 34

<210> SEQ ID NO 41
<211> LENGTH: 34
<212> TYPE: DNA
<213> ORGANISM: Artificial Sequence
<220> FEATURE:
<223> OTHER INFORMATION: PCR primer

<400> SEQUENCE: 41
catcaatgga tcggtgtgca aaggaggcaa tgag 34

<210> SEQ ID NO 42
<211> LENGTH: 32
<212> TYPE: DNA
<213> ORGANISM: Artificial Sequence
<220> FEATURE:
<223> OTHER INFORMATION: PCR primer

<400> SEQUENCE: 42
tccaaaatgc gtgacctgag gatggacaag ac 32

<210> SEQ ID NO 43
<211> LENGTH: 32
<212> TYPE: DNA
<213> ORGANISM: Artificial Sequence
<220> FEATURE:
<223> OTHER INFORMATION: PCR primer

<400> SEQUENCE: 43
gtcttgtcca tcctcaggtc acgcattttg ga 32

<210> SEQ ID NO 44
<211> LENGTH: 37
<212> TYPE: DNA
<213> ORGANISM: Artificial Sequence
<220> FEATURE:
<223> OTHER INFORMATION: PCR primer

<400> SEQUENCE: 44
gagcttggct gcctgaaggc aatcattctg tttaatc 37

<210> SEQ ID NO 45
<211> LENGTH: 37
<212> TYPE: DNA
<213> ORGANISM: Artificial Sequence
<220> FEATURE:
<223> OTHER INFORMATION: PCR primer

<400> SEQUENCE: 45
gattaaacag aatgattgcc ttcaggcagc caagctc 37

<210> SEQ ID NO 46
<211> LENGTH: 39
<212> TYPE: DNA
<213> ORGANISM: Artificial Sequence
<220> FEATURE:
<223> OTHER INFORMATION: PCR primer

<400> SEQUENCE: 46
cattctgttt aatccagagg tcaggggcct ctccaaccc 39

<210> SEQ ID NO 47
<211> LENGTH: 39
<212> TYPE: DNA
<213> ORGANISM: Artificial Sequence
<220> FEATURE:
<223> OTHER INFORMATION: PCR primer

<400> SEQUENCE: 47
gggttggaga ggcccctgac ctctggatta aacagaatg 39

<210> SEQ ID NO 48
<211> LENGTH: 42
<212> TYPE: DNA
<213> ORGANISM: Artificial Sequence
<220> FEATURE:
<223> OTHER INFORMATION: PCR primer

<400> SEQUENCE: 48
gatgccaagg gcctcaagtc cgcgcaggag gtggaggtcc tg 42

<210> SEQ ID NO 49
<211> LENGTH: 42
<212> TYPE: DNA
<213> ORGANISM: Artificial Sequence
<220> FEATURE:
<223> OTHER INFORMATION: PCR primer

<400> SEQUENCE: 49
caggacctcc acctcctgcg cggacttgag gcccttggca tc 42

<210> SEQ ID NO 50
<211> LENGTH: 37
<212> TYPE: DNA
<213> ORGANISM: Artificial Sequence
<220> FEATURE:
<223> OTHER INFORMATION: PCR primer

<400> SEQUENCE: 50
cctagtgagg tggagctcct gcgggagaaa gtgtatg 37

<210> SEQ ID NO 51
<211> LENGTH: 37
<212> TYPE: DNA
<213> ORGANISM: Artificial Sequence
<220> FEATURE:
<223> OTHER INFORMATION: PCR primer

<400> SEQUENCE: 51
catacacttt ctcccgcagg agctccacct cactagg 37

<210> SEQ ID NO 52
<211> LENGTH: 33
<212> TYPE: DNA
<213> ORGANISM: Artificial Sequence
<220> FEATURE:
<223> OTHER INFORMATION: PCR primer

<400> SEQUENCE: 52
gagaaagtgt atgcagcact ggagacctac tgc 33

-continued

<210> SEQ ID NO 53
<211> LENGTH: 33
<212> TYPE: DNA
<213> ORGANISM: Artificial Sequence
<220> FEATURE:
<223> OTHER INFORMATION: PCR primer

<400> SEQUENCE: 53
gcagtaggtc tccagtgctg catacacttt ctc 33

<210> SEQ ID NO 54
<211> LENGTH: 33
<212> TYPE: DNA
<213> ORGANISM: Artificial Sequence
<220> FEATURE:
<223> OTHER INFORMATION: PCR primer

<400> SEQUENCE: 54
gtgtatgcat cactggatac ctactgcaaa cag 33

<210> SEQ ID NO 55
<211> LENGTH: 33
<212> TYPE: DNA
<213> ORGANISM: Artificial Sequence
<220> FEATURE:
<223> OTHER INFORMATION: PCR primer

<400> SEQUENCE: 55
ctgtttgcag taggtatcca gtgatgcata cac 33

<210> SEQ ID NO 56
<211> LENGTH: 34
<212> TYPE: DNA
<213> ORGANISM: Artificial Sequence
<220> FEATURE:
<223> OTHER INFORMATION: PCR primer

<400> SEQUENCE: 56
gtatgcatca ctggaggagt actgcaaaca gaag 34

<210> SEQ ID NO 57
<211> LENGTH: 34
<212> TYPE: DNA
<213> ORGANISM: Artificial Sequence
<220> FEATURE:
<223> OTHER INFORMATION: PCR primer

<400> SEQUENCE: 57
cttctgtttg cagtactcct ccagtgatgc atac 34

<210> SEQ ID NO 58
<211> LENGTH: 42
<212> TYPE: DNA
<213> ORGANISM: Artificial Sequence
<220> FEATURE:
<223> OTHER INFORMATION: PCR primer

<400> SEQUENCE: 58
gagaaagtgt atgcagcact ggatgagtac tgcaaacaga ag 42

<210> SEQ ID NO 59
<211> LENGTH: 42
<212> TYPE: DNA
<213> ORGANISM: Artificial Sequence
<220> FEATURE:
<223> OTHER INFORMATION: PCR primer

<400> SEQUENCE: 59
cttctgtttg cagtactcat ccagtgctgc atacactttc tc 42

<210> SEQ ID NO 60
<211> LENGTH: 48
<212> TYPE: DNA
<213> ORGANISM: Artificial Sequence
<220> FEATURE:
<223> OTHER INFORMATION: PCR primer

<400> SEQUENCE: 60
catcactgga gacctacacc agaacgacgc accctgagca gcagggac 48

<210> SEQ ID NO 61
<211> LENGTH: 48
<212> TYPE: DNA
<213> ORGANISM: Artificial Sequence
<220> FEATURE:
<223> OTHER INFORMATION: PCR primer

<400> SEQUENCE: 61
gtccctgctg ctcagggtgc gtcgttctgg tgtaggtctc cagtgatg 48

<210> SEQ ID NO 62
<211> LENGTH: 40
<212> TYPE: DNA
<213> ORGANISM: Artificial Sequence
<220> FEATURE:
<223> OTHER INFORMATION: PCR primer

<400> SEQUENCE: 62
caaacagaag taccctgacg agccgggacg gtttgccaag 40

<210> SEQ ID NO 63
<211> LENGTH: 40
<212> TYPE: DNA
<213> ORGANISM: Artificial Sequence
<220> FEATURE:
<223> OTHER INFORMATION: PCR primer

<400> SEQUENCE: 63
cttggcaaac cgtcccggct cgtcagggta cttctgtttg 40

<210> SEQ ID NO 64
<211> LENGTH: 33
<212> TYPE: DNA
<213> ORGANISM: Artificial Sequence
<220> FEATURE:
<223> OTHER INFORMATION: PCR primer

<400> SEQUENCE: 64
ctgctacgtc ttccttccct ccggtccatt ggc 33

<210> SEQ ID NO 65
<211> LENGTH: 33
<212> TYPE: DNA
<213> ORGANISM: Artificial Sequence
<220> FEATURE:
<223> OTHER INFORMATION: PCR primer

<400> SEQUENCE: 65
gccaatggac cggagggaag gaagacgtag cag 33

<210> SEQ ID NO 66
<211> LENGTH: 33
<212> TYPE: DNA
<213> ORGANISM: Artificial Sequence
<220> FEATURE:
<223> OTHER INFORMATION: PCR primer

<400> SEQUENCE: 66
gccctccggt ccattagcct taagtgtcta gag 33

<210> SEQ ID NO 67
<211> LENGTH: 33
<212> TYPE: DNA
<213> ORGANISM: Artificial Sequence
<220> FEATURE:
<223> OTHER INFORMATION: PCR primer

<400> SEQUENCE: 67
ctctagacac ttaaggctaa tggaccggag ggc 33

<210> SEQ ID NO 68
<211> LENGTH: 33
<212> TYPE: DNA
<213> ORGANISM: Artificial Sequence
<220> FEATURE:
<223> OTHER INFORMATION: PCR primer

<400> SEQUENCE: 68
catctgtttt tcttcaggct cattggtgac acc 33

<210> SEQ ID NO 69
<211> LENGTH: 33
<212> TYPE: DNA
<213> ORGANISM: Artificial Sequence
<220> FEATURE:
<223> OTHER INFORMATION: PCR primer

<400> SEQUENCE: 69
ggtgtcacca atgagcctga agaaaaacag atg 33

<210> SEQ ID NO 70
<211> LENGTH: 33
<212> TYPE: DNA
<213> ORGANISM: Artificial Sequence
<220> FEATURE:
<223> OTHER INFORMATION: PCR primer

<400> SEQUENCE: 70
agctcattgg tgacgtcccc atcgacacct tcc 33

<210> SEQ ID NO 71
<211> LENGTH: 33
<212> TYPE: DNA
<213> ORGANISM: Artificial Sequence
<220> FEATURE:
<223> OTHER INFORMATION: PCR primer

<400> SEQUENCE: 71
ggaaggtgtc gatggggacg tcaccaatga gct 33

<210> SEQ ID NO 72
<211> LENGTH: 33
<212> TYPE: DNA
<213> ORGANISM: Artificial Sequence
<220> FEATURE:
<223> OTHER INFORMATION: PCR primer

<400> SEQUENCE: 72
atggagatgc ttgagtctcc ccatcaactg gcc 33

<210> SEQ ID NO 73
<211> LENGTH: 33
<212> TYPE: DNA
<213> ORGANISM: Artificial Sequence
<220> FEATURE:
<223> OTHER INFORMATION: PCR primer

<400> SEQUENCE: 73
ggccagttga tggggagact caagcatctc cat 33

<210> SEQ ID NO 74
<211> LENGTH: 1586
<212> TYPE: DNA
<213> ORGANISM: Bamecia argentifoli

<400> SEQUENCE: 74
gaattcgcgg ccgctcgcaa acttccgtac ctctcacccc ctcgccagga ccccccgcca 60
accagttcac cgtcatctcc tccaatggat actcatcccc catgtcttcg ggcagctacg 120
acccttatag tcccaccaat ggaagaatag ggaaagaaga gctttcgccg gcgaatagtc 180
tgaacgggta caacgtggat agctgcgatg cgtcgcggaa gaagaaggga ggaacgggtc 240
ggcagcagga ggagctgtgt ctcgtctgcg gggaccgcgc ctccggctac cactacaacg 300
ccctcacctg cgaaggctgc aagggcttct tccgtcggag catcaccaag aatgccgtct 360
accagtgtaa atatggaaat aattgtgaaa ttgacatgta catgaggcga aaatgccaag 420
agtgtcgtct caagaagtgt ctcagcgttg gcatgaggcc agaatgtgta gttcccgaat 480
tccagtgtgc tgtgaagcga aaagagaaaa aagcgcaaaa ggacaaagat aaacctaact 540
caacgacgag ttgttctcca gatggaatca aacaagagat agatcctcaa aggctggata 600
cagattcgca gctattgtct gtaaatggag ttaaacccat tactccagag caagaagagc 660
tcatccatag gctagtttat tttcaaaatg aatatgaaca tccatcccca gaggatatca 720
aaaggatagt taatgctgca ccagaagaag aaaatgtagc tgaagaaagg tttaggcata 780
ttacagaaat tacaattctc actgtacagt taattgtgga attttctaag cgattacctg 840
gttttgacaa actaattcgt gaagatcaaa tagctttatt aaaggcatgt agtagtgaag 900
taatgatgtt tagaatggca aggaggtatg atgctgaaac agattcgata ttgtttgcaa 960
ctaaccagcc gtatacgaga gaatcataca ctgtagctgg catgggtgat actgtggagg 1020
atctgctccg attttgtcga catatgtgtg ccatgaaagt cgataacgca gaatatgctc 1080
ttctcactgc cattgtaatt ttttcagaac gaccatctct aagtgaaggc tggaaggttg 1140
agaagattca agaaatttac atagaagcat taaaagcata tgttgaaaat cgaaggaaac 1200
catatgcaac aaccattttt gctaagttac tatctgtttt aactgaacta cgaacattag 1260
ggaatatgaa ttcagaaaca tgcttctcat tgaagctgaa gaatagaaag gtgccatcct 1320
tcctcgagga gatttgggat gttgtttcat aaacagtctt acctcaattc catgttactt 1380
ttcatatttg atttatctca gcaggtggct cagtacttat cctcacatta ctgagctcac 1440
ggtatgctca tacaattata acttgtaata tcatatcggt gatgacaaat ttgttacaat 1500
attctttgtt accttaacac aatgttgatc tcataatgat gtatgaattt ttctgttttt 1560
gcaaaaaaaa aagcggccgc gaattc 1586

-continued

<210> SEQ ID NO 75
<211> LENGTH: 1109
<212> TYPE: DNA
<213> ORGANISM: Nephotetix cincticeps

<400> SEQUENCE: 75
caggaggagc tctgcctgtt gtgcggagac cgagcgtcgg gataccacta caacgctctc 60
acctgcgaag gatgcaaggg cttctttcgg aggagtatca ccaaaaacgc agtgtaccag 120
tccaaatacg gcaccaattg tgaaatagac atgtatatgc ggcgcaagtg ccaggagtgc 180
cgactcaaga agtgcctcag tgtagggatg aggccagaat gtgtagtacc tgagtatcaa 240
tgtgccgtaa aaaggaaaga gaaaaaagct caaaaggaca aagataaacc tgtctcttca 300
accaatggct cgcctgaaat gagaatagac caggacaacc gttgtgtggt gttgcagagt 360
gaagacaaca ggtacaactc gagtacgccc agtttcggag tcaaacccct cagtccagaa 420
caagaggagc tcatccacag gctcgtctac ttccagaacg agtacgaaca ccctgccgag 480
gaggatctca agcggatcga gaacctcccc tgtgacgacg atgacccgtg tgatgttcgc 540
tacaaacaca ttacggagat cacaatactc acagtccagc tcatcgtgga gtttgcgaaa 600
aaactgcctg gtttcgacaa actactgaga gaggaccaga tcgtgttgct caaggcgtgt 660
tcgagcgagg tgatgatgct gcggatggcg cggaggtacg acgtccagac agactcgatc 720
ctgttcgcca acaaccagcc gtacacgcga gagtcgtaca cgatggcagg cgtgggggaa 780
gtcatcgaag atctgctgcg gttcggccga ctcatgtgct ccatgaaggt ggacaatgcc 840
gagtatgctc tgctcacggc catcgtcatc ttctccgagc ggccgaacct ggcggaagga 900
tggaaggttg agaagatcca ggagatctac ctggaggcgc tcaagtccta cgtggacaac 960
cgagtgaaac ctcgcagtcc gaccatcttc gccaaactgc tctccgttct caccgagctg 1020
cgaacactcg gcaaccagaa ctccgagatg tgcttctcgt taaactacgc aaccgcaaac 1080
atgccaccgt tcctcgaaga aatctggga 1109